United States Patent
Kas et al.

(10) Patent No.: US 8,501,418 B2
(45) Date of Patent: Aug. 6, 2013

(54) METHOD OF TREATING RENAL DYSFUNCTION BASED ON PERLECAN AS A BIOMARKER

(75) Inventors: Koen Kas, Schilde (BE); Griet Vanpoucke, Merelbeke (BE); Piet Moerman, Deurle (BE)

(73) Assignee: Pronata N.V., Zwijnaarde (BE)

( * ) Notice: Subject to any disclaimer, the term of this patent is extended or adjusted under 35 U.S.C. 154(b) by 0 days.

(21) Appl. No.: 13/204,443

(22) Filed: Aug. 5, 2011

(65) Prior Publication Data

US 2012/0034240 A1 Feb. 9, 2012

Related U.S. Application Data

(60) Provisional application No. 61/371,334, filed on Aug. 6, 2010.

(30) Foreign Application Priority Data

Aug. 6, 2010 (EP) ..................................... 10172170

(51) Int. Cl.
*G01N 33/53* (2006.01)
*G01N 33/567* (2006.01)
*G01N 24/00* (2006.01)

(52) U.S. Cl.
USPC ........................................... 435/7.1; 436/173

(58) Field of Classification Search
None
See application file for complete search history.

(56) References Cited

U.S. PATENT DOCUMENTS

| | | | | |
|---|---|---|---|---|
| 7,141,551 | B1 * | 11/2006 | DeCarlo et al. | 514/44 R |
| 7,238,488 | B2 * | 7/2007 | Maresh et al. | 435/7.1 |
| 2003/0104999 | A1 | 6/2003 | Iozzo | |

FOREIGN PATENT DOCUMENTS

WO WO 88/06620 9/1988

OTHER PUBLICATIONS

Chen, et al. "A Protective Role for Kidney Apolipoprotein E," *The Journal of Biological Chemistry*, vol. 276, No. 52, pp. 49142-49147, Dec. 2001.
Jia, et al. "Expression of Angiopoietin-Like 3 Associated with Puromycin-Induced Podocyte Damage," *Nephron Experimental Nephrology*, vol. 115, No. 3, pp. E38-E45, Jul. 1, 2010.
Miner, et al., "Molecular and Functional Defects in Kidneys of Mice Lacking Collagen α3(IV): Implications of Alport Syndrome," *The Journal of Cell Biology*, vol. 135, No. 5, pp. 1403-1413, Dec. 1996.
O'Riordan, et al. "Urinary Proteomic Analysis of Chronic Allograft Nephropathy,"*Proteomics Clinical Applications*, vol. 2, Nos. 7-8, pp. 1025-1035, Jul. 1, 2008.
Oda, et al. "Purification and Characterization of Perlecan Fragment in Urine of End-stage Renal Failure Patients," *Clinica Chimica Acta*, vol. 244, No. 2, pp. 119-132, 1996.

* cited by examiner

*Primary Examiner* — Robert Landsman
(74) *Attorney, Agent, or Firm* — Knobbe, Martens, Olson & Bear LLP

(57) ABSTRACT

The application discloses PERLECAN as a new biomarker for renal dysfunction; methods for predicting, diagnosing, prognosticating and/or monitoring said dysfunction based on measuring said biomarker; and kits and devices for measuring said biomarker and/or performing said methods.

8 Claims, 11 Drawing Sheets

FIG. 1A

```
   1  mgwraagall lalllhgrll avthglrayd glslpediet vtasqmrwth sylsddedml
  61  adsisgddlg sgdlgsgdfq mvyfralvnf trsieyspql edagsrefre vseavvdtle
 121  seylkipgdq vvsvvfikel dgwvfveldv gsegnadgaq iqemllrvis sgsvasyvts
 181  pqgfqfrrlg tvpqfpract eaefachsyn ecvaleyrcd rrpdcrdmsd elnceepvlg
 241  isptfsllve ttslpprpet timrqppvth apqpllpgsv rplpcgpqea acrnghcipr
 301  dylcdgqedc edgsdeldcg ppppcepnef pcgnghcalk lwrcdgdfdc edrtdeancp
 361  tkrpeevcgp tqfrcvstnm cipasfhcde esdcpdrsde fgcmppqvvt ppresiqasr
 421  gqtvtftcva igvptpiinw rlnwghipsh prvtvtsegg rgtliirdvk esdqgaytce
 481  amnargmvfg ipdgvlclvp qrgpcpdghf ylchsaaclp cfcfgitsvc qstrrfrdqi
 541  rlrfdqpddf kgvnvtmpaq pgtpplsstq lqidpslhcf qlvdlsrrfl vhdsfwalpc
 601  qflgnkvdsy ggslrynvry clargmlcpv qrpdvvlvga gyrllsrght ptqpgalnqr
 661  qvqfseehwv hesgrpvqra ellqvlqsle avliqtvynt kmasvglsdi amdttvthat
 721  shgrahsvee crcpigysgl scescdahft rvpggpylgt csgcncngha sscdpvyghc
 781  lncqhntegp qcnkckagff gdamkatats crpcpcpyid asrrfsdtcf ldtdgqatcd
 841  acapgytgrr cescapgyeg npiqpggkcr pvnqeivrcd ergsmgtsge acrcknnvvg
 901  rlcnecadgs fhlstrnpdg clkcfcmgvs rhctssswsr aqlhgaseep ghfsltnaas
 961  thttnegifs ptpgelgfss fhrllsgpyf wslpsrflgd kvtsyggelr ftvtqrsqpg
1021  stplhgqplv vlqgnniile hhvaqepspg qpstfivpfr eqawqrpdgq patrehllma
1081  lagidtllir asyaqqpaes rvsgismdva vpeetgqdpa leveqcscpp gyrgpscqdc
1141  dtgytrtpsg lylgtcercs chghseacep etgacqgcqh htegprceqc qpgyygdaqr
1201  gtpqdcqlcp cygdpaagqa ahtcfldtdg hptcdacspg hsgrhcerca pgyygnpsqg
1261  qpcqrdsqvp gpigcncdpq gsvssqcdaa gqcqckaqve gltcshcrph hfhlsasnpd
1321  gclpcfcmgi tqqcassayt rhlisthfap gdfqgfalvn pqrnsrltge ftvepvpega
1381  qlsfgnfaql ghesfywqlp etyqgdkvaa yggklrytls ytagpqgspl sdpdvqitgn
1441  nimlvasqpa lqgperrsye imfreefwrr pdgqpatreh llmaladlde lliratfssv
```

FIG. 1A continued

```
1501 plaaslsavs leveqpgpsn rpraleveec rcppgyigls cqdcapgytr tgsglylghc
1561 elcecnghsd lchpetgacs qcqhnaagef celcapgyyg datagtpedc qpcacpltnp
1621 enmfsrtces lgaggyrcta cepgytgqyc eqcgpgyvgn psvqggqclp etnqaplvve
1681 vhparsivpq ggshslrcqv sgspphyfyw sredgrpvps gtqqrhqgse lhfpsvqpsd
1741 agvyictcrn lhqsntsrae llvteapskp itvtveeqrs qsvrpgadvt fictaksksp
1801 aytlvwtrlh ngklptramd fngiltirnv qlsdagtyvc tgsnmfamdq gtatlhvqas
1861 gtlsapvvsi hppqltvqpg qlacfrcsat gsptptlcwt ggpggqlpak aqihggilrl
1921 paveptdqaq ylcrahssag qqvaravlhv hgggprvqv spertqvhag rtvrlycraa
1981 gvpsatitwr keggslppqa rsertdiatl lipaittada gfylcvatsp agtaqariqv
2041 vvlsasdasp ppvkiesssp svtegqtldl ncvvagsaha qvtwyrrggs lpphtqvhgs
2101 rlrlpqvspa dsgeyvcrve ngsgpkeasi tvsvlhgths gpsytpvpgs trpiriepss
2161 shvaegqtld lncvvpgqah aqvtwhkrgg slparhqthg sllrlhqvtp adsgeyvchv
2221 vgtsgpleas vlvtieasvi pgpippvrie ssssstvaegq tldlscvvag qahaqvtwyk
2281 rggslparhq vrgsrlyifq aspadagqyv crasngmeas itvtvtgtqg anlaypagst
2341 qpiricpsss qvacgqtldl ncvvpgqsha qvtwhkrggs lpvrhqthgs llrlyqaspa
2401 dsgeyvcrvl gssvpleasv lvtiepagsv palgvtptvr iessssqvae gqtldlnclv
2461 agqahaqvtw hkrggslpar hqvhgsrlrl lqvtpadsge yvcrvvgssq tqeasvlvti
2521 qqrlsgshsq gvaypvries ssaslanght ldlnclvasq aphtitwykr ggslpsrhqi
2581 vgsrlripqv tpadsgeyvc hvsngagsre tslivtiqgs gsshvpsvsp piriessspt
2641 vvegqtldln cvvarqpqai itwykrggsl psrhqthgsh lrlhqmsvad sgeyvcrann
2701 nidaleasiv isvspsagsp sapgssmpir iesssshvae getldlncvv pgqahaqvtw
2761 hkrggslpsh hqtrgsrlrl hhvspadsge yvcrvmgssg pleasvlvti easgssavhv
2821 papggappir iepsssrvae gqtldlkcvv pgqahaqvtw hkrggnlpar hqvhgpllrl
2881 nqvspadsge yscqvtgssq tleasvlvti epsspgpipa pglaqpiyie assshvtegq
2941 tldlncvvpg qahaqvtwyk rggslparhq thgsqlrlhl vspadsgeyv craasgpgpe
3001 qeasftvtvp psegssyrlr spvisidpps stvqqgqdas fkclihdgaa pislewktrn
3061 qelednvhis pngsiitivg trpsnhgtyr cvasnaygva qsvvnlsvhg pptvsvlpeg
3121 pvwvkvgkav tlecvsagep rssarwtris stpakleqrt yglmdshavl qissakpsda
3181 gtyvclaqna lgtaqkqvev ivdtgamapg apqvqaeeae ltveaghtat lrcsatgspa
```

FIG. 1A continued

```
3241 ptihwsklrs plpwqhrleg dtliiprvaq qdsgqyicna tspaghaeat iilhvesppy
3301 attvpehasv qagetvqlqc lahgtppltf qwsrvgsslp gratarnell hferaapeds
3361 gryrcrvtnk vgsaeafaql lvqgppgslp atsipagstp tvqvtpqlet ksigasvefh
3421 cavpsdrgtq lrwfkeggql ppghsvqdgv lriqnldqsc qgtyicqahg pwgkaqasaq
3481 lviqalpsvl inirtsvqtv vvghavefec lalgdpkpqv twskvgghlr pgivqsggvv
3541 riahvelada gqyrctatna agttqshvll lvqalpqism pqevrvpags aavfpciasg
3601 yptpdiswsk ldgslppdsr lennmlmlps vrpqdagtyv ctatnrqgkv kafahlqvpe
3661 rvvpyftqtp ysflplptik dayrkfeiki tfrpdsadgm llyngqkrvp gsptnlanrq
3721 pdfisfglvg grpefrfdag sgmatirhpt plalghfhtv tllrsltqgs livgdlapvn
3781 gtsqgkfqgl dlneelylgg ypdygaipka glssgfigcv relriqgeei vfhdlnltah
3841 gishcptcrd rpcqnggqch dscsssyvcv cpagftgsrc chsqalhchp cacgpdatcv
3901 nrpdgrgytc rchlgrsglr ceegvtvttp slsgagsyla lpaltnthhe lrldvefkpl
3961 apdgvllfsg gksgpvedfv slamvgghle fryelgsgla vlrsaeplal grwhrvsaer
4021 lnkdgslrvn ggrpvlrssp gksqglnlht llylggveps vplspatnms ahfrgcvgev
4081 svngkrldlt ysflgsqgig qcydsspcer qpcqhgatcm pageyefqcl crdgfkgdlc
4141 eheenpcqlr epclhggtcq gtrclclpgf sgprcqqgsq hgiaesdwhl egsggndapg
4201 qygayfhddg flafpghvfs rslpevpeti elevrtstas glllwqgvev geagqgkdfi
4261 slglqdghlv fryqlgsgea rlvsedpind gewhrvtalr egrrGSIQVD GEELVSGRsp
4321 gpnvavnakg svyiggapdv atltggrfss gitgcvknlv lhsarPGAPP PQPLDLQHRa
4381 qagantrpcp s      (SEQ ID NO: 1)
```

FIG. 1B

```
  1 eikitfrpds adgmllyngq krvpgsptnl anrqpdfisf glvggrpefr fdagsgmati
 61 rhptplalgh fhtvtllrsl tqgslivgdl apvngtsqgk fqgldlneel ylggypdyga
121 ipkaglssgf igcvrelriq geeivfhdln ltahgishcp tcrdrpcqng gqchdsesss
181 yvcvcpagft gsrcehsqal hchpeacgpd atcvnrpdgr gytcrchlgr sglrceegvt
241 vttpslsgag sylalpaltn thhelrldve fkplapdgvl lfsggksgpv edfvslamvg
301 ghlefryelg sglavlrsae plalgrwhrv saerlnkdgs lrvnggrpvl rsspgksqgl
361 nlhtllylgg vepsvplspa tnmsahfrgc vgevsvngkr ldltysflgs qgigqcydss
421 pccrqpcqhg atcmpagcyc fqclcrdgfk gdlcchccnp cqlrcpclhg gtcqgtrclc
481 lpgfsgprcq qgsghgiacs dwhlcgsggn dapgqygayf hddgflafpg hvfsrslpcv
541 petielevrt stasglllwq gvevgeagqg kdfislglqd ghlvfryqlg sgearlvsed
601 pindgewhrv talregrrgs iqvdgeelvs grspgpnvav nakgsvyigg apdvatltgg
661 rfssgitgcv knlvlhsarp gapppqpldl qhraqagant rpcps    (SEQ ID NO: 2)
```

FIG. 1C

```
  1 dapgqygayf hddgflafpg hvfsrslpcv petielevrt stasglllwq gvevgcagqg
 61 kdfislglqd ghlvfryqlg sgearlvsed pindgewhrv talregrrgs iqvdgeelvs
121 grspgpnvav nakgsvyigg apdvatltgg rfssgitgcv knlvlhsarp gapppqpldl
181 qhraqagant rpcps    (SEQ ID NO: 3)
```

FIG. 1D  GSIQVDGEELVSGR    (SEQ ID NO: 4)

FIG. 1E  PGAPPPQPLDLQHR    (SEQ ID NO: 5)

FIG. 1F  SLPEVPETIELEVR    (SEQ ID NO: 6)

FIG. 1G  LEGDTLIIPR    (SEQ ID NO: 7)

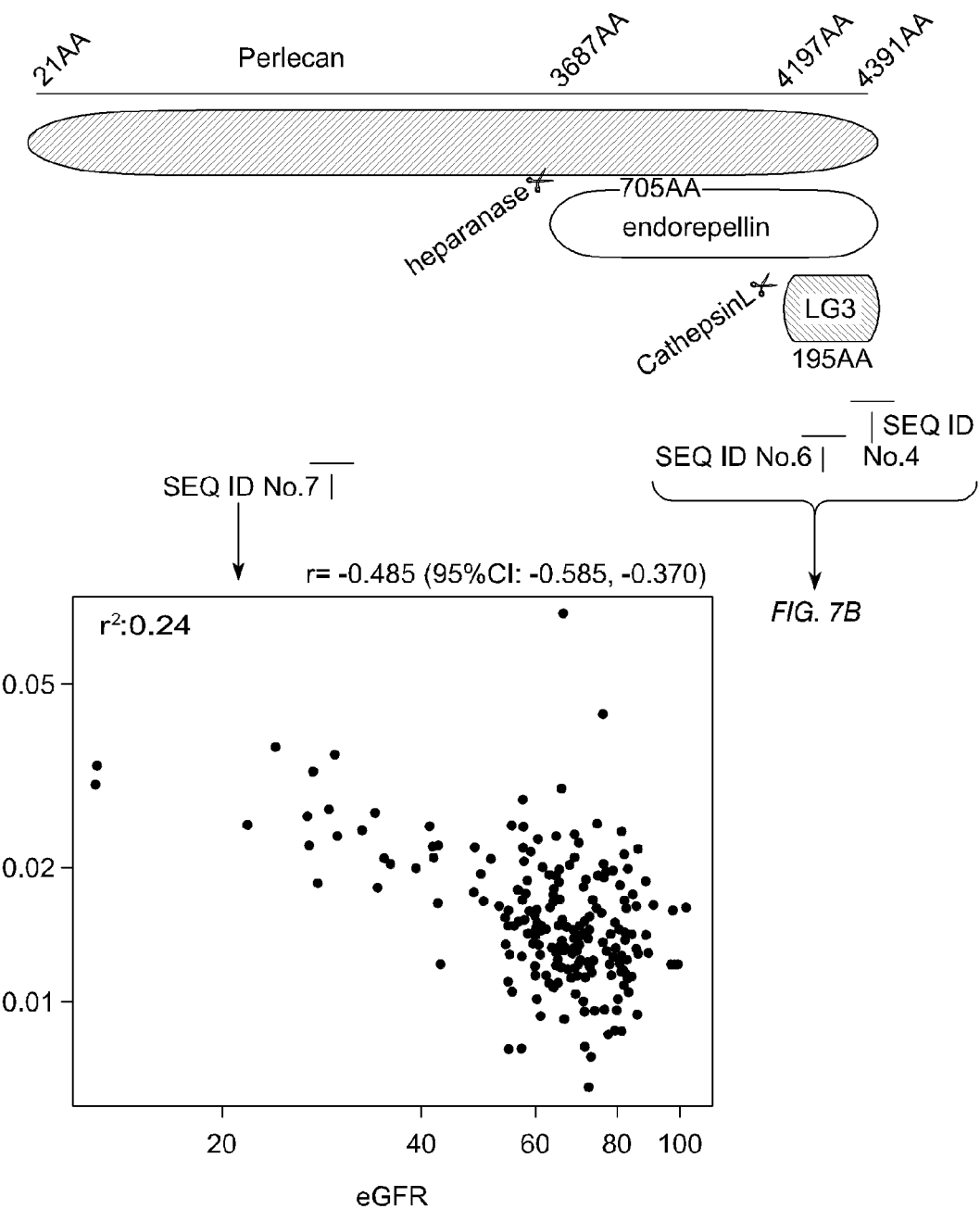

SEQUENCE LISTING

<160> NUMBER OF SEQ ID NOS: 7

<210> SEQ ID NO 1
<211> LENGTH: 4391
<212> TYPE: PRT
<213> ORGANISM: Homo sapiens

<400> SEQUENCE: 1

```
Met Gly Trp Arg Ala Ala Gly Ala Leu Leu Leu Ala Leu Leu Leu His
1               5                   10                  15

Gly Arg Leu Leu Ala Val Thr His Gly Leu Arg Ala Tyr Asp Gly Leu
            20                  25                  30

Ser Leu Pro Glu Asp Ile Glu Thr Val Thr Ala Ser Gln Met Arg Trp
            35                  40                  45

Thr His Ser Tyr Leu Ser Asp Asp Glu Asp Met Leu Ala Asp Ser Ile
        50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
            100                 105                 110

Glu Ala Val Val Asp Thr Leu Glu Ser Glu Tyr Leu Lys Ile Pro Gly
            115                 120                 125

Asp Gln Val Val Ser Val Val Phe Ile Lys Glu Leu Asp Gly Trp Val
130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190

Pro Gln Phe Pro Arg Ala Cys Thr Glu Ala Glu Phe Ala Cys His Ser
            195                 200                 205

Tyr Asn Glu Cys Val Ala Leu Glu Tyr Arg Cys Asp Arg Arg Pro Asp
    210                 215                 220

Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
            245                 250                 255

Arg Pro Glu Thr Thr Ile Met Arg Gln Pro Pro Val Thr His Ala Pro
            260                 265                 270

Gln Pro Leu Leu Pro Gly Ser Val Arg Pro Leu Pro Cys Gly Pro Gln
            275                 280                 285

Glu Ala Ala Cys Arg Asn Gly His Cys Ile Pro Arg Asp Tyr Leu Cys
            290                 295                 300

Asp Gly Gln Glu Asp Cys Glu Asp Gly Ser Asp Glu Leu Asp Cys Gly
305                 310                 315                 320

Pro Pro Pro Pro Cys Glu Pro Asn Glu Phe Pro Cys Gly Asn Gly His
            325                 330                 335

Cys Ala Leu Lys Leu Trp Arg Cys Asp Gly Asp Phe Asp Cys Glu Asp
            340                 345                 350

Arg Thr Asp Glu Ala Asn Cys Pro Thr Lys Arg Pro Glu Glu Val Cys
            355                 360                 365

Gly Pro Thr Gln Phe Arg Cys Val Ser Thr Asn Met Cys Ile Pro Ala
            370                 375                 380

Ser Phe His Cys Asp Glu Glu Ser Asp Cys Pro Asp Arg Ser Asp Glu
385                 390                 395                 400

Phe Gly Cys Met Pro Pro Gln Val Val Thr Pro Pro Arg Glu Ser Ile
            405                 410                 415

Gln Ala Ser Arg Gly Gln Thr Val Thr Phe Thr Cys Val Ala Ile Gly
```

```
                420              425              430
    Val Pro Thr Pro Ile Ile Asn Trp Arg Leu Asn Trp Gly His Ile Pro
                    435              440              445
    Ser His Pro Arg Val Thr Val Thr Ser Glu Gly Gly Arg Gly Thr Leu
        450              455              460
    Ile Ile Arg Asp Val Lys Glu Ser Asp Gln Gly Ala Tyr Thr Cys Glu
    465              470              475              480
    Ala Met Asn Ala Arg Gly Met Val Phe Gly Ile Pro Asp Gly Val Leu
                    485              490              495
    Glu Leu Val Pro Gln Arg Gly Pro Cys Pro Asp Gly His Phe Tyr Leu
        500              505              510
    Glu His Ser Ala Ala Cys Leu Pro Cys Phe Cys Phe Gly Ile Thr Ser
        515              520              525
    Val Cys Gln Ser Thr Arg Arg Phe Arg Asp Gln Ile Arg Leu Arg Phe
        530              535              540
    Asp Gln Pro Asp Asp Phe Lys Gly Val Asn Val Thr Met Pro Ala Gln
    545              550              555              560
    Pro Gly Thr Pro Pro Leu Ser Ser Thr Gln Leu Gln Ile Asp Pro Ser
                    565              570              575
    Leu His Glu Phe Gln Leu Val Asp Leu Ser Arg Arg Phe Leu Val His
                    580              585              590
    Asp Ser Phe Trp Ala Leu Pro Glu Gln Phe Leu Gly Asn Lys Val Asp
                    595              600              605
    Ser Tyr Gly Gly Ser Leu Arg Tyr Asn Val Arg Tyr Glu Leu Ala Arg
        610              615              620
    Gly Met Leu Glu Pro Val Gln Arg Pro Asp Val Val Leu Val Gly Ala
    625              630              635              640
    Gly Tyr Arg Leu Leu Ser Arg Gly His Thr Pro Thr Gln Pro Gly Ala
                    645              650              655
    Leu Asn Gln Arg Gln Val Gln Phe Ser Glu Glu His Trp Val His Glu
                    660              665              670
    Ser Gly Arg Pro Val Gln Arg Ala Glu Leu Leu Gln Val Leu Gln Ser
        675              680              685
    Leu Glu Ala Val Leu Ile Gln Thr Val Tyr Asn Thr Lys Met Ala Ser
        690              695              700
    Val Gly Leu Ser Asp Ile Ala Met Asp Thr Thr Val Thr His Ala Thr
    705              710              715              720
    Ser His Gly Arg Ala His Ser Val Glu Glu Cys Arg Cys Pro Ile Gly
                    725              730              735
    Tyr Ser Gly Leu Ser Cys Glu Ser Cys Asp Ala His Phe Thr Arg Val
                    740              745              750
    Pro Gly Gly Pro Tyr Leu Gly Thr Cys Ser Gly Cys Asn Cys Asn Gly
        755              760              765
    His Ala Ser Ser Cys Asp Pro Val Tyr Gly His Cys Leu Asn Cys Gln
        770              775              780
    His Asn Thr Glu Gly Pro Gln Cys Asn Lys Cys Lys Ala Gly Phe Phe
    785              790              795              800
    Gly Asp Ala Met Lys Ala Thr Ala Thr Ser Cys Arg Pro Cys Pro Cys
                    805              810              815
    Pro Tyr Ile Asp Ala Ser Arg Arg Phe Ser Asp Thr Cys Phe Leu Asp
                    820              825              830
    Thr Asp Gly Gln Ala Thr Cys Asp Ala Cys Ala Pro Gly Tyr Thr Gly
                    835              840              845
```

-continued

Arg Arg Cys Glu Ser Cys Ala Pro Gly Tyr Glu Gly Asn Pro Ile Gln
850             855             860

Pro Gly Gly Lys Cys Arg Pro Val Asn Gln Glu Ile Val Arg Cys Asp
865             870             875             880

Glu Arg Gly Ser Met Gly Thr Ser Gly Glu Ala Cys Arg Cys Lys Asn
                885             890             895

Asn Val Val Gly Arg Leu Cys Asn Glu Cys Ala Asp Gly Ser Phe His
            900             905             910

Leu Ser Thr Arg Asn Pro Asp Gly Cys Leu Lys Cys Phe Cys Met Gly
        915             920             925

Val Ser Arg His Cys Thr Ser Ser Trp Ser Arg Ala Gln Leu His
    930             935             940

Gly Ala Ser Glu Glu Pro Gly His Phe Ser Leu Thr Asn Ala Ala Ser
945             950             955             960

Thr His Thr Thr Asn Glu Gly Ile Phe Ser Pro Thr Pro Gly Glu Leu
            965             970             975

Gly Phe Ser Ser Phe His Arg Leu Leu Ser Gly Pro Tyr Phe Trp Ser
        980             985             990

Leu Pro Ser Arg Phe Leu Gly Asp Lys Val Thr Ser Tyr Gly Gly Glu
    995             1000            1005

Leu Arg Phe Thr Val Thr Gln Arg Ser Gln Pro Gly Ser Thr Pro
    1010            1015            1020

Leu His Gly Gln Pro Leu Val Val Leu Gln Gly Asn Asn Ile Ile
    1025            1030            1035

Leu Glu His His Val Ala Gln Glu Pro Ser Pro Gly Gln Pro Ser
    1040            1045            1050

Thr Phe Ile Val Pro Phe Arg Glu Gln Ala Trp Gln Arg Pro Asp
    1055            1060            1065

Gly Gln Pro Ala Thr Arg Glu His Leu Leu Met Ala Leu Ala Gly
    1070            1075            1080

Ile Asp Thr Leu Leu Ile Arg Ala Ser Tyr Ala Gln Gln Pro Ala
    1085            1090            1095

Glu Ser Arg Val Ser Gly Ile Ser Met Asp Val Ala Val Pro Glu
    1100            1105            1110

Glu Thr Gly Gln Asp Pro Ala Leu Glu Val Glu Gln Cys Ser Cys
    1115            1120            1125

Pro Pro Gly Tyr Arg Gly Pro Ser Cys Gln Asp Cys Asp Thr Gly
    1130            1135            1140

Tyr Thr Arg Thr Pro Ser Gly Leu Tyr Leu Gly Thr Cys Glu Arg
    1145            1150            1155

Cys Ser Cys His Gly His Ser Glu Ala Cys Glu Pro Glu Thr Gly
    1160            1165            1170

Ala Cys Gln Gly Cys Gln His His Thr Glu Gly Pro Arg Cys Glu
    1175            1180            1185

Gln Cys Gln Pro Gly Tyr Tyr Gly Asp Ala Gln Arg Gly Thr Pro
    1190            1195            1200

Gln Asp Cys Gln Leu Cys Pro Cys Tyr Gly Asp Pro Ala Ala Gly
    1205            1210            1215

Gln Ala Ala His Thr Cys Phe Leu Asp Thr Asp Gly His Pro Thr
    1220            1225            1230

Cys Asp Ala Cys Ser Pro Gly His Ser Gly Arg His Cys Glu Arg
    1235            1240            1245

Cys Ala Pro Gly Tyr Tyr Gly Asn Pro Ser Gln Gly Gln Pro Cys
    1250            1255            1260

```
Gln Arg Asp Ser Gln Val Pro Gly Pro Ile Gly Cys Asn Cys Asp
1265                1270                1275

Pro Gln Gly Ser Val Ser Gln Cys Asp Ala Ala Gly Gln Cys
    1280            1285                1290

Gln Cys Lys Ala Gln Val Glu Gly Leu Thr Cys Ser His Cys Arg
1295                1300                1305

Pro His His Phe His Leu Ser Ala Ser Asn Pro Asp Gly Cys Leu
    1310            1315                1320

Pro Cys Phe Cys Met Gly Ile Thr Gln Gln Cys Ala Ser Ser Ala
    1325            1330                1335

Tyr Thr Arg His Leu Ile Ser Thr His Phe Ala Pro Gly Asp Phe
    1340            1345                1350

Gln Gly Phe Ala Leu Val Asn Pro Gln Arg Asn Ser Arg Leu Thr
    1355            1360                1365

Gly Glu Phe Thr Val Glu Pro Val Pro Glu Gly Ala Gln Leu Ser
    1370            1375                1380

Phe Gly Asn Phe Ala Gln Leu Gly His Glu Ser Phe Tyr Trp Gln
    1385            1390                1395

Leu Pro Glu Thr Tyr Gln Gly Asp Lys Val Ala Ala Tyr Gly Gly
    1400            1405                1410

Lys Leu Arg Tyr Thr Leu Ser Tyr Thr Ala Gly Pro Gln Gly Ser
    1415            1420                1425

Pro Leu Ser Asp Pro Asp Val Gln Ile Thr Gly Asn Asn Ile Met
    1430            1435                1440

Leu Val Ala Ser Gln Pro Ala Leu Gln Gly Pro Glu Arg Arg Ser
    1445            1450                1455

Tyr Glu Ile Met Phe Arg Glu Phe Trp Arg Arg Pro Asp Gly
    1460            1465                1470

Gln Pro Ala Thr Arg Glu His Leu Leu Met Ala Leu Ala Asp Leu
    1475            1480                1485

Asp Glu Leu Leu Ile Arg Ala Thr Phe Ser Ser Val Pro Leu Ala
    1490            1495                1500

Ala Ser Ile Ser Ala Val Ser Leu Glu Val Ala Gln Pro Gly Pro
    1505            1510                1515

Ser Asn Arg Pro Arg Ala Leu Glu Val Glu Glu Cys Arg Cys Pro
    1520            1525                1530

Pro Gly Tyr Ile Gly Leu Ser Cys Gln Asp Cys Ala Pro Gly Tyr
    1535            1540                1545

Thr Arg Thr Gly Ser Gly Leu Tyr Leu Gly His Cys Glu Leu Cys
    1550            1555                1560

Glu Cys Asn Gly His Ser Asp Leu Cys His Pro Glu Thr Gly Ala
    1565            1570                1575

Cys Ser Gln Cys Gln His Asn Ala Ala Gly Glu Phe Cys Glu Leu
    1580            1585                1590

Cys Ala Pro Gly Tyr Tyr Gly Asp Ala Thr Ala Gly Thr Pro Glu
    1595            1600                1605

Asp Cys Gln Pro Cys Ala Cys Pro Leu Thr Asn Pro Glu Asn Met
    1610            1615                1620

Phe Ser Arg Thr Cys Glu Ser Leu Gly Ala Gly Gly Tyr Arg Cys
    1625            1630                1635

Thr Ala Cys Glu Pro Gly Tyr Thr Gly Gln Tyr Cys Glu Gln Cys
    1640            1645                1650

Gly Pro Gly Tyr Val Gly Asn Pro Ser Val Gln Gly Gly Gln Cys
```

```
              1655                1660                1665

Leu Pro Glu Thr Asn Gln Ala Pro Leu Val Val Glu Val His Pro
    1670                1675                1680

Ala Arg Ser Ile Val Pro Gln Gly Gly Ser His Ser Leu Arg Cys
    1685                1690                1695

Gln Val Ser Gly Ser Pro Pro His Tyr Phe Tyr Trp Ser Arg Glu
    1700                1705                1710

Asp Gly Arg Pro Val Pro Ser Gly Thr Gln Gln Arg His Gln Gly
    1715                1720                1725

Ser Glu Leu His Phe Pro Ser Val Gln Pro Ser Asp Ala Gly Val
    1730                1735                1740

Tyr Ile Cys Thr Cys Arg Asn Leu His Gln Ser Asn Thr Ser Arg
    1745                1750                1755

Ala Glu Leu Leu Val Thr Glu Ala Pro Ser Lys Pro Ile Thr Val
    1760                1765                1770

Thr Val Glu Glu Gln Arg Ser Gln Ser Val Arg Pro Gly Ala Asp
    1775                1780                1785

Val Thr Phe Ile Cys Thr Ala Lys Ser Lys Ser Pro Ala Tyr Thr
    1790                1795                1800

Leu Val Trp Thr Arg Leu His Asn Gly Lys Leu Pro Thr Arg Ala
    1805                1810                1815

Met Asp Phe Asn Gly Ile Leu Thr Ile Arg Asn Val Gln Leu Ser
    1820                1825                1830

Asp Ala Gly Thr Tyr Val Cys Thr Gly Ser Asn Met Phe Ala Met
    1835                1840                1845

Asp Gln Gly Thr Ala Thr Leu His Val Gln Ala Ser Gly Thr Leu
    1850                1855                1860

Ser Ala Pro Val Val Ser Ile His Pro Pro Gln Leu Thr Val Gln
    1865                1870                1875

Pro Gly Gln Leu Ala Glu Phe Arg Cys Ser Ala Thr Gly Ser Pro
    1880                1885                1890

Thr Pro Thr Leu Glu Trp Thr Gly Gly Pro Gly Gly Gln Leu Pro
    1895                1900                1905

Ala Lys Ala Gln Ile His Gly Gly Ile Leu Arg Leu Pro Ala Val
    1910                1915                1920

Glu Pro Thr Asp Gln Ala Gln Tyr Leu Cys Arg Ala His Ser Ser
    1925                1930                1935

Ala Gly Gln Gln Val Ala Arg Ala Val Leu His Val His Gly Gly
    1940                1945                1950

Gly Gly Pro Arg Val Gln Val Ser Pro Glu Arg Thr Gln Val His
    1955                1960                1965

Ala Gly Arg Thr Val Arg Leu Tyr Cys Arg Ala Ala Gly Val Pro
    1970                1975                1980

Ser Ala Thr Ile Thr Trp Arg Lys Glu Gly Gly Ser Leu Pro Pro
    1985                1990                1995

Gln Ala Arg Ser Glu Arg Thr Asp Ile Ala Thr Leu Leu Ile Pro
    2000                2005                2010

Ala Ile Thr Thr Ala Asp Ala Gly Phe Tyr Leu Cys Val Ala Thr
    2015                2020                2025

Ser Pro Ala Gly Thr Ala Gln Ala Arg Ile Gln Val Val Val Leu
    2030                2035                2040

Ser Ala Ser Asp Ala Ser Pro Pro Val Lys Ile Glu Ser Ser
    2045                2050                2055
```

```
Ser Pro Ser Val Thr Glu Gly Gln Thr Leu Asp Leu Asn Cys Val
2060                 2065                 2070

Val Ala Gly Ser Ala His Ala Gln Val Thr Trp Tyr Arg Arg Gly
2075                 2080                 2085

Gly Ser Leu Pro Pro His Thr Gln Val His Gly Ser Arg Leu Arg
2090                 2095                 2100

Leu Pro Gln Val Ser Pro Ala Asp Ser Gly Glu Tyr Val Cys Arg
2105                 2110                 2115

Val Glu Asn Gly Ser Gly Pro Lys Glu Ala Ser Ile Thr Val Ser
2120                 2125                 2130

Val Leu His Gly Thr His Ser Gly Pro Ser Tyr Thr Pro Val Pro
2135                 2140                 2145

Gly Ser Thr Arg Pro Ile Arg Ile Glu Pro Ser Ser Ser His Val
2150                 2155                 2160

Ala Glu Gly Gln Thr Leu Asp Leu Asn Cys Val Val Pro Gly Gln
2165                 2170                 2175

Ala His Ala Gln Val Thr Trp His Lys Arg Gly Gly Ser Leu Pro
2180                 2185                 2190

Ala Arg His Gln Thr His Gly Ser Leu Leu Arg Leu His Gln Val
2195                 2200                 2205

Thr Pro Ala Asp Ser Gly Glu Tyr Val Cys His Val Val Gly Thr
2210                 2215                 2220

Ser Gly Pro Leu Glu Ala Ser Val Leu Val Thr Ile Glu Ala Ser
2225                 2230                 2235

Val Ile Pro Gly Pro Ile Pro Pro Val Arg Ile Glu Ser Ser Ser
2240                 2245                 2250

Ser Thr Val Ala Glu Gly Gln Thr Leu Asp Leu Ser Cys Val Val
2255                 2260                 2265

Ala Gly Gln Ala His Ala Gln Val Thr Trp Tyr Lys Arg Gly Gly
2270                 2275                 2280

Ser Leu Pro Ala Arg His Gln Val Arg Gly Ser Arg Leu Tyr Ile
2285                 2290                 2295

Phe Gln Ala Ser Pro Ala Asp Ala Gly Gln Tyr Val Cys Arg Ala
2300                 2305                 2310

Ser Asn Gly Met Glu Ala Ser Ile Thr Val Thr Val Thr Gly Thr
2315                 2320                 2325

Gln Gly Ala Asn Leu Ala Tyr Pro Ala Gly Ser Thr Gln Pro Ile
2330                 2335                 2340

Arg Ile Glu Pro Ser Ser Ser Gln Val Ala Glu Gly Gln Thr Leu
2345                 2350                 2355

Asp Leu Asn Cys Val Val Pro Gly Gln Ser His Ala Gln Val Thr
2360                 2365                 2370

Trp His Lys Arg Gly Gly Ser Leu Pro Val Arg His Gln Thr His
2375                 2380                 2385

Gly Ser Leu Leu Arg Leu Tyr Gln Ala Ser Pro Ala Asp Ser Gly
2390                 2395                 2400

Glu Tyr Val Cys Arg Val Leu Gly Ser Ser Val Pro Leu Glu Ala
2405                 2410                 2415

Ser Val Leu Val Thr Ile Glu Pro Ala Gly Ser Val Pro Ala Leu
2420                 2425                 2430

Gly Val Thr Pro Thr Val Arg Ile Glu Ser Ser Ser Ser Gln Val
2435                 2440                 2445

Ala Glu Gly Gln Thr Leu Asp Leu Asn Cys Leu Val Ala Gly Gln
2450                 2455                 2460
```

```
Ala His Ala Gln Val Thr Trp His Lys Arg Gly Gly Ser Leu Pro
    2465                2470                2475

Ala Arg His Gln Val His Gly Ser Arg Leu Arg Leu Leu Gln Val
    2480                2485                2490

Thr Pro Ala Asp Ser Gly Glu Tyr Val Cys Arg Val Val Gly Ser
    2495                2500                2505

Ser Gly Thr Gln Glu Ala Ser Val Leu Val Thr Ile Gln Gln Arg
    2510                2515                2520

Leu Ser Gly Ser His Ser Gln Gly Val Ala Tyr Pro Val Arg Ile
    2525                2530                2535

Glu Ser Ser Ser Ala Ser Leu Ala Asn Gly His Thr Leu Asp Leu
    2540                2545                2550

Asn Cys Leu Val Ala Ser Gln Ala Pro His Thr Ile Thr Trp Tyr
    2555                2560                2565

Lys Arg Gly Gly Ser Leu Pro Ser Arg His Gln Ile Val Gly Ser
    2570                2575                2580

Arg Leu Arg Ile Pro Gln Val Thr Pro Ala Asp Ser Gly Glu Tyr
    2585                2590                2595

Val Cys His Val Ser Asn Gly Ala Gly Ser Arg Glu Thr Ser Leu
    2600                2605                2610

Ile Val Thr Ile Gln Gly Ser Gly Ser Ser His Val Pro Ser Val
    2615                2620                2625

Ser Pro Pro Ile Arg Ile Glu Ser Ser Ser Pro Thr Val Val Glu
    2630                2635                2640

Gly Gln Thr Leu Asp Leu Asn Cys Val Val Ala Arg Gln Pro Gln
    2645                2650                2655

Ala Ile Ile Thr Trp Tyr Lys Arg Gly Gly Ser Leu Pro Ser Arg
    2660                2665                2670

His Gln Thr His Gly Ser His Leu Arg Leu His Gln Met Ser Val
    2675                2680                2685

Ala Asp Ser Gly Glu Tyr Val Cys Arg Ala Asn Asn Asn Ile Asp
    2690                2695                2700

Ala Leu Glu Ala Ser Ile Val Ile Ser Val Ser Pro Ser Ala Gly
    2705                2710                2715

Ser Pro Ser Ala Pro Gly Ser Ser Met Pro Ile Arg Ile Glu Ser
    2720                2725                2730

Ser Ser Ser His Val Ala Glu Gly Glu Thr Leu Asp Leu Asn Cys
    2735                2740                2745

Val Val Pro Gly Gln Ala His Ala Gln Val Thr Trp His Lys Arg
    2750                2755                2760

Gly Gly Ser Leu Pro Ser His His Gln Thr Arg Gly Ser Arg Leu
    2765                2770                2775

Arg Leu His His Val Ser Pro Ala Asp Ser Gly Glu Tyr Val Cys
    2780                2785                2790

Arg Val Met Gly Ser Ser Gly Pro Leu Glu Ala Ser Val Leu Val
    2795                2800                2805

Thr Ile Glu Ala Ser Gly Ser Ser Ala Val His Val Pro Ala Pro
    2810                2815                2820

Gly Gly Ala Pro Pro Ile Arg Ile Glu Pro Ser Ser Ser Arg Val
    2825                2830                2835

Ala Glu Gly Gln Thr Leu Asp Leu Lys Cys Val Val Pro Gly Gln
    2840                2845                2850

Ala His Ala Gln Val Thr Trp His Lys Arg Gly Gly Asn Leu Pro
```

```
                    2855                2860                2865

Ala Arg His Gln Val His Gly Pro Leu Arg Leu Asn Gln Val
        2870                2875                2880

Ser Pro Ala Asp Ser Gly Glu Tyr Ser Cys Gln Val Thr Gly Ser
        2885                2890                2895

Ser Gly Thr Leu Glu Ala Ser Val Leu Val Thr Ile Glu Pro Ser
        2900                2905                2910

Ser Pro Gly Pro Ile Pro Ala Pro Gly Leu Ala Gln Pro Ile Tyr
        2915                2920                2925

Ile Glu Ala Ser Ser His Val Thr Glu Gly Gln Thr Leu Asp
        2930                2935                2940

Leu Asn Cys Val Val Pro Gly Gln Ala His Ala Gln Val Thr Trp
        2945                2950                2955

Tyr Lys Arg Gly Gly Ser Leu Pro Ala Arg His Gln Thr His Gly
        2960                2965                2970

Ser Gln Leu Arg Leu His Leu Val Ser Pro Ala Asp Ser Gly Glu
        2975                2980                2985

Tyr Val Cys Arg Ala Ala Ser Gly Pro Gly Pro Glu Gln Glu Ala
        2990                2995                3000

Ser Phe Thr Val Thr Val Pro Pro Ser Glu Gly Ser Ser Tyr Arg
        3005                3010                3015

Leu Arg Ser Pro Val Ile Ser Ile Asp Pro Pro Ser Ser Thr Val
        3020                3025                3030

Gln Gln Gly Gln Asp Ala Ser Phe Lys Cys Leu Ile His Asp Gly
        3035                3040                3045

Ala Ala Pro Ile Ser Leu Glu Trp Lys Thr Arg Asn Gln Glu Leu
        3050                3055                3060

Glu Asp Asn Val His Ile Ser Pro Asn Gly Ser Ile Ile Thr Ile
        3065                3070                3075

Val Gly Thr Arg Pro Ser Asn His Gly Thr Tyr Arg Cys Val Ala
        3080                3085                3090

Ser Asn Ala Tyr Gly Val Ala Gln Ser Val Val Asn Leu Ser Val
        3095                3100                3105

His Gly Pro Pro Thr Val Ser Val Leu Pro Glu Gly Pro Val Trp
        3110                3115                3120

Val Lys Val Gly Lys Ala Val Thr Leu Glu Cys Val Ser Ala Gly
        3125                3130                3135

Glu Pro Arg Ser Ser Ala Arg Trp Thr Arg Ile Ser Ser Thr Pro
        3140                3145                3150

Ala Lys Leu Glu Gln Arg Thr Tyr Gly Leu Met Asp Ser His Ala
        3155                3160                3165

Val Leu Gln Ile Ser Ser Ala Lys Pro Ser Asp Ala Gly Thr Tyr
        3170                3175                3180

Val Cys Leu Ala Gln Asn Ala Leu Gly Thr Ala Gln Lys Gln Val
        3185                3190                3195

Glu Val Ile Val Asp Thr Gly Ala Met Ala Pro Gly Ala Pro Gln
        3200                3205                3210

Val Gln Ala Glu Glu Ala Glu Leu Thr Val Glu Ala Gly His Thr
        3215                3220                3225

Ala Thr Leu Arg Cys Ser Ala Thr Gly Ser Pro Ala Pro Thr Ile
        3230                3235                3240

His Trp Ser Lys Leu Arg Ser Pro Leu Pro Trp Gln His Arg Leu
        3245                3250                3255
```

```
Glu Gly Asp Thr Leu Ile Ile Pro Arg Val Ala Gln Gln Asp Ser
    3260            3265            3270

Gly Gln Tyr Ile Cys Asn Ala Thr Ser Pro Ala Gly His Ala Glu
    3275            3280            3285

Ala Thr Ile Ile Leu His Val Glu Ser Pro Pro Tyr Ala Thr Thr
    3290            3295            3300

Val Pro Glu His Ala Ser Val Gln Ala Gly Glu Thr Val Gln Leu
    3305            3310            3315

Gln Cys Leu Ala His Gly Thr Pro Pro Leu Thr Phe Gln Trp Ser
    3320            3325            3330

Arg Val Gly Ser Ser Leu Pro Gly Arg Ala Thr Ala Arg Asn Glu
    3335            3340            3345

Leu Leu His Phe Glu Arg Ala Ala Pro Glu Asp Ser Gly Arg Tyr
    3350            3355            3360

Arg Cys Arg Val Thr Asn Lys Val Gly Ser Ala Glu Ala Phe Ala
    3365            3370            3375

Gln Leu Leu Val Gln Gly Pro Pro Gly Ser Leu Pro Ala Thr Ser
    3380            3385            3390

Ile Pro Ala Gly Ser Thr Pro Thr Val Gln Val Thr Pro Gln Leu
    3395            3400            3405

Glu Thr Lys Ser Ile Gly Ala Ser Val Glu Phe His Cys Ala Val
    3410            3415            3420

Pro Ser Asp Arg Gly Thr Gln Leu Arg Trp Phe Lys Glu Gly Gly
    3425            3430            3435

Gln Leu Pro Pro Gly His Ser Val Gln Asp Gly Val Leu Arg Ile
    3440            3445            3450

Gln Asn Leu Asp Gln Ser Cys Gln Gly Thr Tyr Ile Cys Gln Ala
    3455            3460            3465

His Gly Pro Trp Gly Lys Ala Gln Ala Ser Ala Gln Leu Val Ile
    3470            3475            3480

Gln Ala Leu Pro Ser Val Leu Ile Asn Ile Arg Thr Ser Val Gln
    3485            3490            3495

Thr Val Val Val Gly His Ala Val Glu Phe Glu Cys Leu Ala Leu
    3500            3505            3510

Gly Asp Pro Lys Pro Gln Val Thr Trp Ser Lys Val Gly Gly His
    3515            3520            3525

Leu Arg Pro Gly Ile Val Gln Ser Gly Gly Val Val Arg Ile Ala
    3530            3535            3540

His Val Glu Leu Ala Asp Ala Gly Gln Tyr Arg Cys Thr Ala Thr
    3545            3550            3555

Asn Ala Ala Gly Thr Thr Gln Ser His Val Leu Leu Leu Val Gln
    3560            3565            3570

Ala Leu Pro Gln Ile Ser Met Pro Gln Glu Val Arg Val Pro Ala
    3575            3580            3585

Gly Ser Ala Ala Val Phe Pro Cys Ile Ala Ser Gly Tyr Pro Thr
    3590            3595            3600

Pro Asp Ile Ser Trp Ser Lys Leu Asp Gly Ser Leu Pro Pro Asp
    3605            3610            3615

Ser Arg Leu Glu Asn Asn Met Leu Met Leu Pro Ser Val Arg Pro
    3620            3625            3630

Gln Asp Ala Gly Thr Tyr Val Cys Thr Ala Thr Asn Arg Gln Gly
    3635            3640            3645

Lys Val Lys Ala Phe Ala His Leu Gln Val Pro Glu Arg Val Val
    3650            3655            3660
```

```
Pro Tyr Phe Thr Gln Thr Pro Tyr Ser Phe Leu Pro Leu Pro Thr
3665                3670                3675

Ile Lys Asp Ala Tyr Arg Lys Phe Glu Ile Lys Ile Thr Phe Arg
3680                3685                3690

Pro Asp Ser Ala Asp Gly Met Leu Leu Tyr Asn Gly Gln Lys Arg
3695                3700                3705

Val Pro Gly Ser Pro Thr Asn Leu Ala Asn Arg Gln Pro Asp Phe
3710                3715                3720

Ile Ser Phe Gly Leu Val Gly Gly Arg Pro Glu Phe Arg Phe Asp
3725                3730                3735

Ala Gly Ser Gly Met Ala Thr Ile Arg His Pro Thr Pro Leu Ala
3740                3745                3750

Leu Gly His Phe His Thr Val Thr Leu Leu Arg Ser Leu Thr Gln
3755                3760                3765

Gly Ser Leu Ile Val Gly Asp Leu Ala Pro Val Asn Gly Thr Ser
3770                3775                3780

Gln Gly Lys Phe Gln Gly Leu Asp Leu Asn Glu Glu Leu Tyr Leu
3785                3790                3795

Gly Gly Tyr Pro Asp Tyr Gly Ala Ile Pro Lys Ala Gly Leu Ser
3800                3805                3810

Ser Gly Phe Ile Gly Cys Val Arg Glu Leu Arg Ile Gln Gly Glu
3815                3820                3825

Glu Ile Val Phe His Asp Leu Asn Leu Thr Ala His Gly Ile Ser
3830                3835                3840

His Cys Pro Thr Cys Arg Asp Arg Pro Cys Gln Asn Gly Gly Gln
3845                3850                3855

Cys His Asp Ser Glu Ser Ser Tyr Val Cys Val Cys Pro Ala
3860                3865                3870

Gly Phe Thr Gly Ser Arg Cys Glu His Ser Gln Ala Leu His Cys
3875                3880                3885

His Pro Glu Ala Cys Gly Pro Asp Ala Thr Cys Val Asn Arg Pro
3890                3895                3900

Asp Gly Arg Gly Tyr Thr Cys Arg Cys His Leu Gly Arg Ser Gly
3905                3910                3915

Leu Arg Cys Glu Glu Gly Val Thr Val Thr Thr Pro Ser Leu Ser
3920                3925                3930

Gly Ala Gly Ser Tyr Leu Ala Leu Pro Ala Leu Thr Asn Thr His
3935                3940                3945

His Glu Leu Arg Leu Asp Val Glu Phe Lys Pro Leu Ala Pro Asp
3950                3955                3960

Gly Val Leu Leu Phe Ser Gly Gly Lys Ser Gly Pro Val Glu Asp
3965                3970                3975

Phe Val Ser Leu Ala Met Val Gly Gly His Leu Glu Phe Arg Tyr
3980                3985                3990

Glu Leu Gly Ser Gly Leu Ala Val Leu Arg Ser Ala Glu Pro Leu
3995                4000                4005

Ala Leu Gly Arg Trp His Arg Val Ser Ala Glu Arg Leu Asn Lys
4010                4015                4020

Asp Gly Ser Leu Arg Val Asn Gly Gly Arg Pro Val Leu Arg Ser
4025                4030                4035

Ser Pro Gly Lys Ser Gln Gly Leu Asn Leu His Thr Leu Leu Tyr
4040                4045                4050

Leu Gly Gly Val Glu Pro Ser Val Pro Leu Ser Pro Ala Thr Asn
```

```
                 4055                4060                4065

Met Ser Ala His Phe Arg Gly Cys Val Gly Glu Val Ser Val Asn
    4070                4075                4080

Gly Lys Arg Leu Asp Leu Thr Tyr Ser Phe Leu Gly Ser Gln Gly
    4085                4090                4095

Ile Gly Gln Cys Tyr Asp Ser Ser Pro Cys Glu Arg Gln Pro Cys
    4100                4105                4110

Gln His Gly Ala Thr Cys Met Pro Ala Gly Glu Tyr Glu Phe Gln
    4115                4120                4125

Cys Leu Cys Arg Asp Gly Phe Lys Gly Asp Leu Cys Glu His Glu
    4130                4135                4140

Glu Asn Pro Cys Gln Leu Arg Glu Pro Cys Leu His Gly Gly Thr
    4145                4150                4155

Cys Gln Gly Thr Arg Cys Leu Cys Leu Pro Gly Phe Ser Gly Pro
    4160                4165                4170

Arg Cys Gln Gln Gly Ser Gly His Gly Ile Ala Glu Ser Asp Trp
    4175                4180                4185

His Leu Glu Gly Ser Gly Gly Asn Asp Ala Pro Gly Gln Tyr Gly
    4190                4195                4200

Ala Tyr Phe His Asp Asp Gly Phe Leu Ala Phe Pro Gly His Val
    4205                4210                4215

Phe Ser Arg Ser Leu Pro Glu Val Pro Glu Thr Ile Glu Leu Glu
    4220                4225                4230

Val Arg Thr Ser Thr Ala Ser Gly Leu Leu Leu Trp Gln Gly Val
    4235                4240                4245

Glu Val Gly Glu Ala Gly Gln Gly Lys Asp Phe Ile Ser Leu Gly
    4250                4255                4260

Leu Gln Asp Gly His Leu Val Phe Arg Tyr Gln Leu Gly Ser Gly
    4265                4270                4275

Glu Ala Arg Leu Val Ser Glu Asp Pro Ile Asn Asp Gly Glu Trp
    4280                4285                4290

His Arg Val Thr Ala Leu Arg Glu Gly Arg Arg Gly Ser Ile Gln
    4295                4300                4305

Val Asp Gly Glu Glu Leu Val Ser Gly Arg Ser Pro Gly Pro Asn
    4310                4315                4320

Val Ala Val Asn Ala Lys Gly Ser Val Tyr Ile Gly Gly Ala Pro
    4325                4330                4335

Asp Val Ala Thr Leu Thr Gly Gly Arg Phe Ser Ser Gly Ile Thr
    4340                4345                4350

Gly Cys Val Lys Asn Leu Val Leu His Ser Ala Arg Pro Gly Ala
    4355                4360                4365

Pro Pro Pro Gln Pro Leu Asp Leu Gln His Arg Ala Gln Ala Gly
    4370                4375                4380

Ala Asn Thr Arg Pro Cys Pro Ser
    4385                4390

<210> SEQ ID NO 2
<211> LENGTH: 705
<212> TYPE: PRT
<213> ORGANISM: Homo sapiens

<400> SEQUENCE: 2

Glu Ile Lys Ile Thr Phe Arg Pro Asp Ser Ala Asp Gly Met Leu Leu
1               5                   10                  15

Tyr Asn Gly Gln Lys Arg Val Pro Gly Ser Pro Thr Asn Leu Ala Asn
```

```
                    20                  25                  30
Arg Gln Pro Asp Phe Ile Ser Phe Gly Leu Val Gly Arg Pro Glu
            35                  40                  45

Phe Arg Phe Asp Ala Gly Ser Gly Met Ala Thr Ile Arg His Pro Thr
        50                  55                  60

Pro Leu Ala Leu Gly His Phe His Thr Val Thr Leu Leu Arg Ser Leu
65                  70                  75                  80

Thr Gln Gly Ser Leu Ile Val Gly Asp Leu Ala Pro Val Asn Gly Thr
                85                  90                  95

Ser Gln Gly Lys Phe Gln Gly Leu Asp Leu Asn Glu Glu Leu Tyr Leu
            100                 105                 110

Gly Gly Tyr Pro Asp Tyr Gly Ala Ile Pro Lys Ala Gly Leu Ser Ser
        115                 120                 125

Gly Phe Ile Gly Cys Val Arg Glu Leu Arg Ile Gln Gly Glu Glu Ile
    130                 135                 140

Val Phe His Asp Leu Asn Leu Thr Ala His Gly Ile Ser His Cys Pro
145                 150                 155                 160

Thr Cys Arg Asp Arg Pro Cys Gln Asn Gly Gly Gln Cys His Asp Ser
                165                 170                 175

Glu Ser Ser Ser Tyr Val Cys Val Cys Pro Ala Gly Phe Thr Gly Ser
            180                 185                 190

Arg Cys Glu His Ser Gln Ala Leu His Cys His Pro Glu Ala Cys Gly
        195                 200                 205

Pro Asp Ala Thr Cys Val Asn Arg Pro Asp Gly Arg Gly Tyr Thr Cys
    210                 215                 220

Arg Cys His Leu Gly Arg Ser Gly Leu Arg Cys Glu Glu Gly Val Thr
225                 230                 235                 240

Val Thr Thr Pro Ser Leu Ser Gly Ala Gly Ser Tyr Leu Ala Leu Pro
                245                 250                 255

Ala Leu Thr Asn Thr His His Glu Leu Arg Leu Asp Val Glu Phe Lys
            260                 265                 270

Pro Leu Ala Pro Asp Gly Val Leu Leu Phe Ser Gly Gly Lys Ser Gly
        275                 280                 285

Pro Val Glu Asp Phe Val Ser Leu Ala Met Val Gly Gly His Leu Glu
    290                 295                 300

Phe Arg Tyr Glu Leu Gly Ser Gly Leu Ala Val Leu Arg Ser Ala Glu
305                 310                 315                 320

Pro Leu Ala Leu Gly Arg Trp His Arg Val Ser Ala Glu Arg Leu Asn
                325                 330                 335

Lys Asp Gly Ser Leu Arg Val Asn Gly Gly Arg Pro Val Leu Arg Ser
            340                 345                 350

Ser Pro Gly Lys Ser Gln Gly Leu Asn Leu His Thr Leu Leu Tyr Leu
        355                 360                 365

Gly Gly Val Glu Pro Ser Val Pro Leu Ser Pro Ala Thr Asn Met Ser
    370                 375                 380

Ala His Phe Arg Gly Cys Val Gly Glu Val Ser Val Asn Gly Lys Arg
385                 390                 395                 400

Leu Asp Leu Thr Tyr Ser Phe Leu Gly Ser Gln Gly Ile Gly Gln Cys
                405                 410                 415

Tyr Asp Ser Ser Pro Cys Glu Arg Gln Pro Cys Gln His Gly Ala Thr
            420                 425                 430

Cys Met Pro Ala Gly Glu Tyr Glu Phe Gln Cys Leu Cys Arg Asp Gly
        435                 440                 445
```

Phe Lys Gly Asp Leu Cys Glu His Glu Glu Asn Pro Cys Gln Leu Arg
    450                 455                 460

Glu Pro Cys Leu His Gly Thr Cys Gln Gly Thr Arg Cys Leu Cys
465                 470                 475                 480

Leu Pro Gly Phe Ser Gly Pro Arg Cys Gln Gln Gly Ser Gly His Gly
                485                 490                 495

Ile Ala Glu Ser Asp Trp His Leu Gly Ser Gly Gly Asn Asp Ala
            500                 505                 510

Pro Gly Gln Tyr Gly Ala Tyr Phe His Asp Asp Gly Phe Leu Ala Phe
        515                 520                 525

Pro Gly His Val Phe Ser Arg Ser Leu Pro Glu Val Pro Glu Thr Ile
    530                 535                 540

Glu Leu Glu Val Arg Thr Ser Thr Ala Ser Gly Leu Leu Leu Trp Gln
545                 550                 555                 560

Gly Val Glu Val Gly Glu Ala Gly Gln Gly Lys Asp Phe Ile Ser Leu
                565                 570                 575

Gly Leu Gln Asp Gly His Leu Val Phe Arg Tyr Gln Leu Gly Ser Gly
            580                 585                 590

Glu Ala Arg Leu Val Ser Glu Asp Pro Ile Asn Asp Gly Glu Trp His
        595                 600                 605

Arg Val Thr Ala Leu Arg Glu Gly Arg Arg Gly Ser Ile Gln Val Asp
    610                 615                 620

Gly Glu Glu Leu Val Ser Gly Arg Ser Pro Gly Pro Asn Val Ala Val
625                 630                 635                 640

Asn Ala Lys Gly Ser Val Tyr Ile Gly Gly Ala Pro Asp Val Ala Thr
                645                 650                 655

Leu Thr Gly Gly Arg Phe Ser Ser Gly Ile Thr Gly Cys Val Lys Asn
            660                 665                 670

Leu Val Leu His Ser Ala Arg Pro Gly Ala Pro Pro Gln Pro Leu
        675                 680                 685

Asp Leu Gln His Arg Ala Gln Ala Gly Ala Asn Thr Arg Pro Cys Pro
    690                 695                 700

Ser
705

<210> SEQ ID NO 3
<211> LENGTH: 195
<212> TYPE: PRT
<213> ORGANISM: Homo sapiens

<400> SEQUENCE: 3

Asp Ala Pro Gly Gln Tyr Gly Ala Tyr Phe His Asp Asp Gly Phe Leu
1               5                   10                  15

Ala Phe Pro Gly His Val Phe Ser Arg Ser Leu Pro Glu Val Pro Glu
            20                  25                  30

Thr Ile Glu Leu Glu Val Arg Thr Ser Thr Ala Ser Gly Leu Leu Leu
        35                  40                  45

Trp Gln Gly Val Glu Val Gly Glu Ala Gly Gln Gly Lys Asp Phe Ile
    50                  55                  60

Ser Leu Gly Leu Gln Asp Gly His Leu Val Phe Arg Tyr Gln Leu Gly
65                  70                  75                  80

Ser Gly Glu Ala Arg Leu Val Ser Glu Asp Pro Ile Asn Asp Gly Glu
                85                  90                  95

Trp His Arg Val Thr Ala Leu Arg Glu Gly Arg Arg Gly Ser Ile Gln
            100                 105                 110

-continued

```
Val Asp Gly Glu Glu Leu Val Ser Gly Arg Ser Pro Gly Pro Asn Val
            115                 120                 125

Ala Val Asn Ala Lys Gly Ser Val Tyr Ile Gly Gly Ala Pro Asp Val
        130                 135                 140

Ala Thr Leu Thr Gly Gly Arg Phe Ser Ser Gly Ile Thr Gly Cys Val
145                 150                 155                 160

Lys Asn Leu Val Leu His Ser Ala Arg Pro Gly Ala Pro Pro Gln
                165                 170                 175

Pro Leu Asp Leu Gln His Arg Ala Gln Ala Gly Ala Asn Thr Arg Pro
            180                 185                 190

Cys Pro Ser
        195

<210> SEQ ID NO 4
<211> LENGTH: 14
<212> TYPE: PRT
<213> ORGANISM: Homo sapiens

<400> SEQUENCE: 4

Gly Ser Ile Gln Val Asp Gly Glu Glu Leu Val Ser Gly Arg
1               5                   10

<210> SEQ ID NO 5
<211> LENGTH: 14
<212> TYPE: PRT
<213> ORGANISM: Homo sapiens

<400> SEQUENCE: 5

Pro Gly Ala Pro Pro Gln Pro Leu Asp Leu Gln His Arg
1               5                   10

<210> SEQ ID NO 6
<211> LENGTH: 14
<212> TYPE: PRT
<213> ORGANISM: Homo sapiens

<400> SEQUENCE: 6

Ser Leu Pro Glu Val Pro Glu Thr Ile Glu Leu Glu Val Arg
1               5                   10

<210> SEQ ID NO 7
<211> LENGTH: 10
<212> TYPE: PRT
<213> ORGANISM: Homo sapiens

<400> SEQUENCE: 7

Leu Glu Gly Asp Thr Leu Ile Ile Pro Arg
1               5                   10
```

METHOD OF TREATING RENAL DYSFUNCTION BASED ON PERLECAN AS A BIOMARKER

CROSS-REFERENCE TO RELATED APPLICATIONS

This application claims priority to U.S. Provisional application No. 61/371,334, filed Aug. 6, 2010 and to EP Application No. 10172170.2, filed Aug. 6, 2010. The disclosures of both applications are incorporated herein by reference.

STATEMENT REGARDING FEDERALLY SPONSORED R&D

Not applicable.

PARTIES OF JOINT RESEARCH AGREEMENT

Not applicable.

REFERENCE TO SEQUENCE LISTING, TABLE, OR COMPUTER PROGRAM LISTING

This application contains a sequence listing which is incorporated by reference.

BACKGROUND OF THE INVENTION

1. Field of the Invention

The invention relates to protein- and/or peptide-based biomarkers useful for predicting, diagnosing, prognosticating and/or monitoring diseases and conditions in subjects, in particular renal dysfunction; and to related methods, kits and devices.

2. Background of the Invention

In many diseases and conditions, a favourable outcome of prophylactic and/or therapeutic treatments is strongly correlated with early and/or accurate prediction, diagnosis, prognosis and/or monitoring of a disease or condition. Therefore, there exists a continuous need for additional and preferably improved manners for early and/or accurate prediction, diagnosis, prognosis and/or monitoring of diseases and conditions to guide the treatment choices.

The mammalian renal system plays central roles inter alia in the removal of catabolic waste products from the bloodstream and in the maintenance of fluid and electrolyte balances in the body.

Renal dysfunction encompasses diseases and conditions in which kidney function is inadequate, such as for example diseases and conditions characterised by an acute or chronic deterioration of kidney function, more particularly characterised by an acute or chronic decline in kidney excretory function, as evidenced for example by reduced glomerular filtration rate. Renal dysfunction may develop into a life-threatening condition in which the (systemic) build-up of catabolic waste products and other harmful or toxic substances and/or the development of significant imbalances in bodily fluids or electrolytes may lead to, contribute to or exacerbate the failure of other major organ systems and death.

Signs and symptoms of renal dysfunction may include inter alia increased levels of urea in the blood, volume overload and swelling, abnormal acid levels, abnormal levels of potassium, calcium and/or phosphate, changes in urination, fatigue, skin rash or itching, nausea, dyspnea, reduced kidney size, haematuria and anaemia. However, renal dysfunction is frequently insidious and may progress to an advanced stage before the patient notices problems and decides to seek a physician. Therefore, renal dysfunction is commonly diagnosed late, and the patient may already be in need of radical and non-trivial treatments such as dialysis or kidney transplantation.

To aid diagnosis of renal dysfunction, some methods have been developed previously. For example, one way is to determine the glomerular filtration rate (GFR). However, GFR measurements rely on invasive, time-consuming and expensive procedures involving the injection of exogenous and potentially harmful diagnostic substances and measuring their excretion at specified time period(s). Another method is to measure serum creatinine clearance. Creatinine originates from muscle tissue and is increasingly secreted by renal tubules concomitant with decreasing renal function. However, serum creatinine levels depend on age, sex, diet, muscle mass, ethnic background, physical activity, disease, other manners of secretion, etc., which factors may impair the reliability of creatinine clearance for diagnosis of renal dysfunction. A further endogenous biomarker for diagnosing renal dysfunction is Cystatin C. Advantageously, compared to creatinine the expression of Cystatin C is comparably steady. Nevertheless, Cystatin C does show some limitations: for example, its levels are affected by immunosuppressive therapeutics and are dependent on thyroid function. Cystatin C also does not react rapidly enough to acute changes in GFR and is thus not a satisfactory marker for acute kidney injury (AKI). Another endogenous marker is neutrophil gelatinase-associated lipocalin (NGAL) which appears to detect early stages of acute renal injury. However, the use of NGAL is confounded by its anti-inflammatory role, which may lead to substandard specificity in complicated patient populations.

Furthermore, the timely (i.e. early) discovery of the need of renal replacement therapy (RRT) in postoperative or critically ill patients prone to develop kidney related problems is fundamental to reduce mortality. To date however there is no objective early measure for the need of RRT initiation and a biomarker that can specifically identify those patients that will benefit from early RRT is highly anticipated.

Dependable and preferably early detection and intervention is critical to effective treatment of renal dysfunction. Consequently, provision of further, alternative and preferably improved markers and tools for diagnosis, prediction, prognosis and/or monitoring of renal dysfunction continues to be of prime importance.

The present invention addresses the above needs in the art by identifying biomarkers for renal dysfunction and related diseases and conditions and providing uses therefore.

SUMMARY OF THE INVENTION

Having conducted extensive experiments and tests, the inventors have found that levels of the protein PERLECAN, more precisely the ENDOREPELLIN part thereof and even more precisely the LG-3 domain thereof (called generally "perlecan" hereinafter) in blood samples are closely indicative of kidney function. In particular, in clinical samples from 299 patients PERLECAN showed a significant association with several tested clinical parameters related to kidney function, among others estimated glomerular filtration rate (eGFR), creatinine levels, blood urea nitrogen (BUN) levels, history of kidney failure and Cystatin C levels.

Further, for discriminating subjects with decreased GFR ($<60$ ml/min/1.73 m$^2$) from subjects with normal GFR, the median AUC value (area under the ROC curve; "ROC" stands for receiver operating characteristic) is at least comparable between PERLECAN (0.91) and Cystatin C (0.92). The AUC value is a combined measure of sensitivity and specificity and a higher AUC value (i.e., approaching 1) in general indicates an improved performance of the test.

As mentioned, throughout the specification the term "PERLECAN" may encompass PERLECAN and fragments of PERLECAN, such as the Endorepellin or LG3 domain of PERLECAN. Hence, reference to "PERLECAN" as used herein may also be read as "PERLECAN or a fragment thereof". Preferably, said fragment may be the Endorepellin domain of PERLECAN. Further preferably, said fragment may be the LG3 domain of PERLECAN.

Accordingly, the inventors have realised PERLECAN as a new biomarker advantageous for evaluating renal function.

Further provided is a method for determining renal function in a subject comprising measuring the quantity of PERLECAN in a sample from said subject. Particularly provided is a method for predicting, diagnosing, prognosticating and/or monitoring renal dysfunction in a subject comprising measuring PERLECAN levels in a sample from said subject. As used throughout this specification, measuring the levels of PERLECAN and/or other biomarker(s) in a sample from a subject may particularly denote that the examination phase of a method comprises measuring the quantity of PERLECAN and/or other biomarker(s) in the sample from the subject. One understands that methods of prediction, diagnosis, prognosis and/or monitoring of diseases and conditions generally comprise an examination phase in which data is collected from and/or about the subject.

In an embodiment, a method for predicting, diagnosing and/or prognosticating renal dysfunction comprises the steps of: (i) measuring the quantity of PERLECAN in a sample from the subject; (ii) comparing the quantity of PERLECAN measured in (i) with a reference value of the quantity of PERLECAN, said reference value representing a known prediction, diagnosis and/or prognosis of renal dysfunction or normal renal function; (iii) finding a deviation or no deviation of the quantity of PERLECAN measured in (i) from the reference value; and (iv) attributing said finding of deviation or no deviation to a particular prediction, diagnosis and/or prognosis of renal dysfunction or normal renal function in the subject.

The method for predicting, diagnosing and/or prognosticating renal dysfunction, and in particular such method comprising steps (i) to (iv) as set forth in the previous paragraph, may be performed for a subject at two or more successive time points and the respective outcomes at said successive time points may be compared, whereby the presence or absence of a change between the prediction, diagnosis and/or prognosis of renal dysfunction at said successive time points is determined. The method thus allows to monitor a change in the prediction, diagnosis and/or prognosis of renal dysfunction in a subject over time.

In an embodiment, a method for monitoring renal dysfunction comprises the steps of: (i) measuring the quantity of PERLECAN in samples from a subject from two or more successive time points; (ii) comparing the quantity of PERLECAN between the samples as measured in (i); (iii) finding a deviation or no deviation of the quantity of PERLECAN between the samples as compared in (ii); and (iv) attributing said finding of deviation or no deviation to a change in renal function or renal dysfunction in the subject between the two or more successive time points. The method thus allows to monitor renal dysfunction or renal function in a subject over time. This monitoring can be important to determine the start, type and/or continuation or change in treatment of the renal dysfunction.

Throughout the present disclosure, methods suitable for monitoring any one condition or disease as taught herein can inter alia allow to predict the occurrence of the condition or disease, or to monitor the progression, aggravation, alleviation or recurrence of the condition or disease, or response to treatment or to other external or internal factors, situations or stressors, etc. Advantageously, monitoring methods as taught herein may be applied in the course of a medical treatment of the subject, preferably medical treatment aimed at alleviating the so-monitored condition or disease. Such monitoring may be comprised, e.g., in decision making whether a patient may be discharged, needs a change in treatment or needs further hospitalisation or requires Renal Replacement Therapy (RRT) to be initiated.

Similarly, throughout the present disclosure, methods suitable for prognosticating any one condition or disease as taught herein can inter alia allow to prognosticate the occurrence of the condition or disease, or to prognosticate the progression, aggravation, alleviation or recurrence of the condition or disease, or response to treatment or to other external or internal factors, situations or stressors, etc. may allow to prognosticate As shown in the experimental section, clinical parameters typifying kidney dysfunction, such as for example reduced eGFR and elevated Cystatin C levels, associate with elevated levels of PERLECAN. Consequently, prediction or diagnosis of renal dysfunction or a poor prognosis of renal dysfunction can in particular be associated with an elevated level of PERLECAN.

For example but without limitation, an elevated quantity (i.e., a deviation) of PERLECAN in a sample from a subject compared to a reference value representing the prediction or diagnosis of no renal dysfunction (i.e., normal renal function) or representing a good prognosis for renal dysfunction respectively indicates that the subject has or is at risk of having renal dysfunction or indicates a poor prognosis for renal dysfunction in the subject (such as, e.g., a prognosis that a chronic renal dysfunction patient will progress towards end-stage kidney disease).

Renal dysfunction may be characterised by reduced GFR or eGFR. (Estimated) glomerular filtration rate may be said to be reduced compared to normal, if the GFR or eGFR is below normal by any extent. For example but without limitation: normal GFR or eGFR indicative of normal kidney function may denote values greater than 90 ml/min/1.73 m$^2$; intermediate GFR or eGFR indicative of slightly impaired kidney function may denote values between 60 and 90 ml/min/1.73 m$^2$; and reduced GFR or eGFR indicative of seriously impaired kidney function may denote values lower than 60 ml/min/1.73 m$^2$.

In an exemplary but non-limiting experiment PERLECAN levels provided satisfactory discrimination between normal and reduced GFR when the threshold between normal and reduced GFR was set at 60 ml/min/1.73 m$^2$. Hence, in embodiments a threshold for normal vs. reduced GFR or eGFR may be set at a value between about 50 and about 70 ml/min/1.73 m$^2$, e.g., between about 55 and about 65 ml/min/1.73 m$^2$, e.g., at 55, 56, 57, 58, 59, 60, 61, 62, 63, 64 or 65 ml/min/1.73 m$^2$, and preferably at 60 ml/min/1.73 m$^2$ wherein a value above said threshold reflects normal GFR or eGFR and a value below said threshold denotes reduced GFR or eGFR.

In other embodiments a threshold for normal vs. reduced GFR or eGFR may be set at a value between about 80 and about 100 ml/min/1.73 m$^2$, e.g., between about 85 and about 95 ml/min/1.73 m$^2$, e.g., at 85, 86, 87, 88, 89, 90, 91, 92, 93, 94 or 95 ml/min/1.73 m$^2$, and preferably at 90 ml/min/1.73

$m^2$ wherein a value above said threshold reflects normal GFR or eGFR and a value below said threshold denotes reduced GFR or eGFR.

In an exemplary but non-limiting experiment PERLECAN levels provided satisfactory discrimination between normal, intermediate and reduced GFR when the threshold between normal and intermediate GFR was set at 90 ml/min/1.73 $m^2$ and the threshold between intermediate and reduced GFR was set at 60 ml/min/1.73 $m^2$ Hence, in yet other embodiments, a threshold for intermediate vs. reduced GFR or eGFR may be set at a value between about 50 and about 70 ml/min/1.73 $m^2$, e.g., between about 55 and about 65 ml/min/1.73 $m^2$, e.g., at 55, 56, 57, 58, 59, 60, 61, 62, 63, 64 or 65 ml/min/1.73 $m^2$, and preferably at 60 ml/min/1.73 $m^2$ wherein a value above said threshold reflects intermediate GFR or eGFR and a value below said threshold denotes reduced GFR or eGFR; and a further threshold for normal vs. intermediate GFR or eGFR may be set at a value between about 80 and about 100 ml/min/1.73 $m^2$, e.g., between about 85 and about 95 ml/min/1.73 $m^2$, e.g., at 85, 86, 87, 88, 89, 90, 91, 92, 93, 94 or 95 ml/min/1.73 $m^2$, and preferably at 90 ml/min/1.73 $m^2$ wherein a value above said threshold reflects normal GFR or eGFR and a value below said threshold denotes intermediate GFR or eGFR.

As taught herein, the level of PERLECAN, such as for example the PERLECAN concentration in plasma and for urine, correlates with glomerular filtration rate (GFR). Consequently, the quantity of PERLECAN as measured in a subject can be converted to a GFR value in order to determine or estimate the latter. A suitable conversion formula for such purpose may also include additional factors such as clinical parameters (without limitation, height, age, sex, race, muscle mass, etc.) and/or clinical variables (e.g., blood-measured variables such as without limitation hematocrite, albumin concentration, thyroid hormones, etc.).

Consequently, an aspect provides a method for determining glomerular filtration rate (GFR) of a subject comprising measuring the quantity of PERLECAN in a sample from said subject and converting said measured quantity of PERLECAN to GFR of said subject.

The quantity of PERLECAN as measured in a subject may be converted to a GFR value as a part or step of the herein disclosed diagnosis, prediction, prognosis and/or monitoring methods. So-calculated GFR values may be compared with known GFR values representing various stages of GFR and kidney function impairment. The quantity of PERLECAN may thus be used to determine the degree of GFR reduction in a subject.

Accordingly, in an embodiment of the herein disclosed diagnosis, prediction, prognosis and/or monitoring methods the renal dysfunction may encompass, denote or correspond to GFR reduction.

Also disclosed is a method to determine whether a subject is or will be or is not or will not be (such as, for example, still is, or is no longer) in need of a therapy to treat renal dysfunction, comprising: (i) measuring the quantity of PERLECAN in the sample from the subject; (ii) comparing the quantity of PERLECAN measured in (i) with a reference value of the quantity of PERLECAN, said reference value representing a known diagnosis, prediction and/or prognosis of renal dysfunction or normal renal function; (iii) finding a deviation or no deviation of the quantity of PERLECAN measured in (i) from said reference value; (iv) inferring from said finding the presence or absence of a need for a therapy to treat renal dysfunction. A therapy may be particularly indicated where steps (i) to (iii) allow for a conclusion that the subject has or is at risk of having renal dysfunction or has a poor prognosis for renal dysfunction, such as for example but without limitation, where the quantity of PERLECAN in the sample from the subject is elevated (i.e., a deviation) compared to a reference value representing the prediction or diagnosis of no renal dysfunction (i.e., normal renal function). Without limitation, a patient having renal dysfunction upon admission to or during stay in a medical care centre may be tested as taught herein for the necessity of continuing a treatment of said renal dysfunction, and may be discharged when such treatment is no longer needed or is needed only to a given limited extent.

Particularly, the method may allow to determine whether a subject is or will be or is not or will not be in need of early initiation of said therapy. For example, such determination using PERLECAN may be made earlier and/or may allow for earlier initiation of the therapy compared to currently available markers such as creatinin and urea (blood urea nitrogen).

Exemplary therapies for renal dysfunction encompass without limitation low-potassium and/or low phosphorus diets, phosphorus-lowering medications (e.g., calcium carbonate, calcitriol, sevelamer), red blood cell production stimulating agents (e.g., erythropoietin, darbepoietin), iron supplements, blood pressure medications, vitamin supplements, haemodialysis, ultrafiltration, peritoneal dialysis, and kidney transplantation. The need for RRT (such as haemodialysis, ultrafiltration or peritoneal dialysis) is typically important to test in post-operative or critically ill patients. PERLECAN is shown herein to be a good early marker of the need for RRT and can hence help to decrease mortality in said patients by timely taking over the fluid filtration function of the kidneys.

Hence, in an embodiment, the therapy to treat renal dysfunction may be haemodialysis, ultrafiltration or peritoneal dialysis in postoperative and/or critically ill patients.

In an embodiment, the timing or scheduling of dialysis in a chronic dialysis patient may be informed by alterations in the quantity of PERLECAN measured in said patient over time. For example, dialysis may be scheduled if a predetermined change in PERLECAN quantity is detected in such patient over time.

In embodiments, renal dysfunction as used herein may refer to acute renal failure (acute kidney injury). In other embodiments, renal dysfunction as used herein may refer to chronic renal failure (chronic kidney disease). In further embodiments, renal dysfunction as used herein may be associated or caused by fibrosis of the kidney tissue (renal fibrosis), particularly but without limitation in chronic kidney disease patients or heart failure patients.

Particularly advantageously, renal dysfunction as intended herein may involve acute renal dysfunction or AKI. As demonstrated by the inventors, PERLECAN can detect abrupt changes in renal function. Since AKI commonly entails sudden drops in GFR, the measurement of PERLECAN—as a marker rapidly reacting to such abrupt GFR changes—may be particularly suitable for diagnosing, predicting, prognosticating and/or monitoring AKI.

Using PERLECAN as a marker for AKI may be particularly useful in patients known or expected to be at risk of developing AKI. Without limitation, such PERLECAN testing or screening may be effected in the general population of intensive care unit (ICU) patients (i.e., testing a subject at ICU), such as, e.g., in patients having undergone surgery and more particularly cardiac surgery, in whom the incidence of acute kidney injury can be as high as 30-50%. Also without limitation, PERLECAN testing or screening may be employed in patients undergoing or having undergone coronary or peripheral angiography, in whom the incidence of developing contrast fluid-induced nephropathy may be as high as 5-10%. By means of example, in such situations PERLECAN may be used as a diagnostic marker (e.g., PERLECAN may be measured within a given time, e.g., within 24 hours, following the procedure) or as a predictive marker to identify patients sensitive or prone to AKI development.

As demonstrated in the examples, PERLECAN can identify subjects having renal dysfunction in a subject population presenting with (acute) dyspnea. Dyspnea (dyspnoea or shortness of breath) is a common and distressing symptom which may be connected to a range of underlying pathologies, such as, e.g., lung cancer, chronic obstructive pulmonary disease (COPD), congestive or acute heart failure, and renal dysfunction. To treat a patient manifesting with dyspnea adequately, the underlying problem needs to be established.

Accordingly, in methods of diagnosing, predicting, prognosticating and/or monitoring renal dysfunction as taught herein, the subject may present with (manifest with) dyspnea. Preferably, the dyspnea may be acute dyspnea. Said methods may particularly allow to discriminate between (subjects having) dyspnea associated with or caused by renal dysfunction and (subjects having) dyspnea associated with or caused by other conditions (such as without limitation COPD or pneumonia).

As stated in the examples, the correlations between PERLECAN levels and Cystatin C levels or eGFR persist even following a correction for the presence of acute decompensated heart failure (AHF) in the subject population. Hence, PERLECAN can detect abrupt changes in renal function (eGFR) due to acute decompensation of the heart (i.e., reduced cardiac output).

Accordingly, in methods of diagnosing, predicting, prognosticating and/or monitoring renal dysfunction as taught herein, the subject may have or may be at risk of having heart failure, preferably acute decompensated heart failure (AHF). Such methods may inter alia allow to diagnose acute worsening of renal function associated with or caused by reduced cardiac output, or monitor renal function in the course of treatment of AHF.

As also shown in the examples, the inventors have found that PERLECAN levels upon admission in subjects manifesting with acute dyspnea were significantly higher in those subjects who will have died within one year post-admission compared to those subjects who will have remained alive at one year. This distinction was also observed when the patient population was divided based on the presence or absence of acute heart failure (AHF), or based on renal (dys)function as measured by GFR. Consequently, the inventors have realised PERLECAN as a new biomarker advantageous for predicting or prognosticating mortality in patients with dyspnea, particularly acute dyspnea, in patients with AHF and/or in patients with renal dysfunction, particularly chronic renal dysfunction.

Hence, provided is also a method for predicting or prognosticating mortality in a subject having dyspnea and/or acute heart failure and/or renal dysfunction, comprising measuring the quantity of PERLECAN in a sample from said subject. Preferably, the dyspnea may be acute dyspnea. Preferably, the renal dysfunction may be chronic renal dysfunction, particularly chronic kidney disease. Without limitation, the dyspnea may be associated with or caused by AHF and/or by renal dysfunction; or the dyspnea may be associated with our caused by conditions other than AHF and renal dysfunction; or the subject may have AHF and/or renal dysfunction without dyspnea symptoms.

In an embodiment, the method for predicting or prognosticating mortality in a subject having dyspnea and/or acute heart failure and/or renal dysfunction comprises the steps of: (i) measuring the quantity of PERLECAN in a sample from the subject; (ii) comparing the quantity of PERLECAN measured in (i) with a reference value of the quantity of PERLECAN, said reference value representing a known prediction or prognosis of mortality; (iii) finding a deviation or no deviation of the quantity of PERLECAN measured in (i) from the reference value; and (iv) attributing said finding of deviation or no deviation to a particular prediction or prognosis of mortality in the subject.

The present methods for predicting or prognosticating mortality may be preferably performed for a subject once the subject presents with or is diagnosed with dyspnea and/or acute heart failure and/or renal dysfunction, more preferably upon the initial (first) presentation or diagnosis of said diseases and conditions.

As shown in the experimental section, increased mortality rate in populations of dyspneic and/or AHF and/or renal failure subjects is associated with elevated levels of PERLECAN.

Consequently, prediction or prognostication of increased mortality (increased risk or chance of death within a predetermined time interval) can in particular be associated with an elevated level of PERLECAN.

For example but without limitation, an elevated quantity (i.e., a deviation) of PERLECAN in a sample from a subject compared to a reference value representing the prediction prognosis of a given mortality (i.e., a given, such as a normal, risk or chance of death within a predetermined time interval) indicates that the subject has a comparably greater risk of deceasing within said time interval.

Without limitation, mortality may be suitably expressed as the chance of a subject to decease within an interval of for example several months or several years from the time of performing a prediction or prognostication method, e.g., within about 6 months or within about 1 year or within about 2, about 3, about 4, about 5, about 6, about 7, about 8, about 9 or about 10 years from the time of performing the prediction or prognostication method.

In an exemplary but non-limiting experiment PERLECAN levels provided satisfactory discrimination between normal and increased mortality in dyspnea, in AHF, and in renal dysfunction subjects when the time interval for considering the alive vs. dead status was set at 1 year from the time of performing the prediction or prognostication method. Hence, in embodiments mortality may be suitably expressed as the chance of a subject to decease within an interval of between 6 months and 2 years and preferably within 1 year from performing the prediction or prognostication method.

It shall be appreciated that finding of increased chance of death in a subject can guide therapeutic decisions to treat the subject's diseases or conditions.

The inventors have further found that levels of PERLECAN protein are increased in hypertrophied left ventricles of thoracic aortic constriction (TAC) animals compared to controls. Accordingly, the inventors have realised PERLECAN as a new biomarker advantageous for evaluating left ventricular hypertrophy and cardiac fibrosis. WO 2008/046509 studies the expression of PERLECAN on mRNA level in the DOCA rat model of left ventricular hypertrophy, without a conclusive result.

Another aspect provides PERLECAN as a new biomarker advantageous for evaluating preeclampsia (PE). A further aspect provides PERLECAN as a new biomarker advantageous for evaluating proteinuria, e.g. associated with pregnancy (PAP), or associated with Metabolic syndrome or Type II diabetes.

Hence, provided are methods for predicting, diagnosing, prognosticating and/or monitoring any one of left ventricular hypertrophy (LVH), cardiac fibrosis (CF), PE or PAP in a subject comprising measuring PERLECAN levels in a sample from said subject.

In an embodiment, a method for predicting, diagnosing and/or prognosticating any one of LVH, CF, PE or PAP comprises the steps of: (i) measuring the quantity of PERLECAN in a sample from the subject; (ii) comparing the quantity of PERLECAN measured in (i) with a reference value of the quantity of PERLECAN, said reference value representing a known prediction, diagnosis and/or prognosis of LVH, CF, PE or PAP; (iii) finding a deviation or no deviation of the quantity of PERLECAN measured in (i) from the reference value; and (iv) attributing said finding of deviation or no deviation to a particular prediction, diagnosis and/or prognosis of LVH, CF, PE or PAP in the subject.

The method for predicting, diagnosing and/or prognosticating any one of LVH, CF, PE or PAP, and in particular such method comprising steps (i) to (iv) as set forth in the previous paragraph, may be performed for a subject at two or more successive time points and the respective outcomes at said successive time points may be compared, whereby the presence or absence of a change between the prediction, diagnosis and/or prognosis of LVH, CF, PE or PAP at said successive time points is determined. The method thus allows to monitor a change in the prediction, diagnosis and/or prognosis of any one of LVH, CF, PE or PAP in a subject over time.

In an embodiment, a method for monitoring any one of LVH, CF, PE or PAP comprises the steps of: (i) measuring the quantity of PERLECAN in samples from a subject from two or more successive time points; (ii) comparing the quantity of PERLECAN between the samples as measured in (i); (iii) finding a deviation or no deviation of the quantity of PERLECAN between the samples as compared in (ii); and (iv) attributing said finding of deviation or no deviation to a change in LVH, CF, PE or PAP in the subject between the two or more successive time points. The method thus allows to monitor any one of LVH, CF, PE or PAP in a subject over time.

Prediction or diagnosis of any one of LVH, CF, PE or PAP or a poor prognosis of LVH, CF, PE or PAP can in particular be associated with an elevated level of PERLECAN.

For example but without limitation, an elevated quantity (i.e., a deviation) of PERLECAN in a sample from a subject compared to a reference value representing the prediction or diagnosis of no LVH, CF, PE or PAP (i.e., healthy state) or representing a good prognosis for LVH, CF, PE or PAP respectively indicates that the subject has or is at risk of having LVH, CF, PE or PAP or indicates a poor prognosis for LVH, CF, PE or PAP in the subject.

Also disclosed is a method to determine whether a subject is or will be or is not or will not be (such as, for example, still is, or is no longer) in need of a therapy to treat any one of LVH, CF, PE or PAP, comprising: (i) measuring the quantity of PERLECAN in the sample from the subject; (ii) comparing the quantity of PERLECAN measured in (i) with a reference value of the quantity of PERLECAN, said reference value representing a known diagnosis, prediction and/or prognosis of LVH, CF, PE or PAP; (iii) finding a deviation or no deviation of the quantity of PERLECAN measured in (i) from said reference value; (iv) inferring from said finding the presence or absence of a need for a therapy to treat LVH, CF, PE or PAP.

A therapy may be particularly indicated where steps (i) to (iii) allow for a conclusion that the subject has or is at risk of having LVH, CF, PE or PAP or has a poor prognosis for LVH, CF, PE or PAP, such as for example but without limitation, where the quantity of PERLECAN in the sample from the subject is elevated (i.e., a deviation) compared to a reference value representing the prediction or diagnosis of no LVH, CF, PE or PAP (i.e., healthy state). Without limitation, a patient having LVH, CF, PE or PAP upon admission to or during stay in a medical care centre may be tested as taught herein for the necessity of continuing a treatment of said LVH, CF, PE or PAP, and may be discharged when such treatment is no longer needed or is needed only to a given limited extent.

Any one prediction, diagnosis, prognosis and/or monitoring method as taught herein may preferably allow for sensitivity and/or specificity (preferably, sensitivity and specificity) of at least 50%, at least 60%, at least 70% or at least 80%, e.g., $\geq 85\%$ or $\geq 90\%$ or $\geq 95\%$, e.g., between about 80% and 100% or between about 85% and 95%.

Reference throughout this specification to "diseases and/or conditions" encompasses any such diseases and conditions as disclosed herein insofar consistent with the context of such a recitation, in particular but without limitation including renal dysfunction, dyspnea associated with or caused by renal failure, increased mortality of subjects having dyspnea and/or acute heart failure and/or renal dysfunction, left ventricular hypertrophy, cardiac fibrosis, PE and PAP.

The present methods for predicting, diagnosing, prognosticating and/or monitoring the diseases or conditions may be used in individuals who have not yet been diagnosed as having such (for example, preventative screening), or who have been diagnosed as having such, or who are suspected of having such (for example, display one or more characteristic symptoms), or who are at risk of developing such (for example, genetic predisposition; presence of one or more developmental, environmental or behavioural risk factors). The methods may also be used to detect various stages of progression or severity of the diseases or conditions. The methods may also be used to detect response of the diseases or conditions to prophylactic or therapeutic treatments or other interventions. The methods can furthermore be used to help the medical practitioner in deciding upon worsening, status-quo, partial recovery, or complete recovery of the patient from the diseases or conditions, resulting in either further treatment or observation or in discharge of the patient from medical care centre.

Any one of the herein described methods for predicting, diagnosing, prognosticating and/or monitoring the diseases or conditions may be employed for population screening (such as, e.g., screening in a general population or in a population stratified based on one or more criteria, e.g., age, gender, ancestry, occupation, presence or absence of risk factors of AHF, etc.). In any one the methods, the subject may form part of a patient population showing symptoms of dyspnea.

Diabetes and hypertension represent major risk factors for developing renal dysfunction, more particularly (chronic) kidney failure. Hence, the present diagnosis, prediction, prognosis and/or monitoring methods may be preferably employed in such patients and patient populations, i.e., in subjects having or being at risk of having diabetes and/or hypertension (such as, e.g., in a screening setup).

The present methods enable the medical practitioner to monitor the disease progress by measuring the level of PERLECAN in a sample of the patient. For example, a decrease in PERLECAN level as compared to a prior PERLECAN level (e.g., at the time of the admission to ED) indicates the disease or condition in the subject is improving or has improved, while an increase of the PERLECAN level as compared to a prior PERLECAN level (e.g., at the time of the admission to ED) indicates the disease or condition in the subject has worsened or is worsening. Such worsening could possibly result in the recurrence of the disease or conditions.

In view of the present disclosure, also provided are:
the use of PERLECAN as a marker (biomarker);
the use of PERLECAN as a marker (biomarker) for any one disease or condition as taught herein;
the use of PERLECAN for diagnosis, prediction, prognosis and/or monitoring;
the use of PERLECAN for diagnosis, prediction, prognosis and/or monitoring of any one disease or condition as taught herein;
particularly wherein said condition or disease may be chosen from renal dysfunction, dyspnea associated with or caused by renal failure, increased mortality of subjects having dyspnea and/or acute heart failure and/or renal dysfunction, left ventricular hypertrophy, cardiac fibrosis, PE and PAP.

In the present prediction, diagnosis, prognosis and/or monitoring methods the measurement of PERLECAN may also be combined with the assessment of one or more further biomarkers or clinical parameters relevant for the respective diseases and conditions.

Consequently, also disclosed herein are methods, wherein the examination phase of the methods further comprises measuring the presence or absence and/or quantity of one or more such other markers in the sample from the subject. In this respect, any known or yet unknown suitable marker could be used.

A reference throughout this specification to biomarkers "other than PERLECAN" or "other biomarkers" generally encompasses such other biomarkers which are useful for predicting, diagnosing, prognosticating and/or monitoring the diseases and conditions as disclosed herein. By means of example and not limitation, biomarkers useful in evaluating renal dysfunction include creatinine (i.e., serum creatinine clearance), Cystatin C and neutrophil gelatinase-associated lipocalin (NGAL), beta-trace protein, kidney injury molecule 1 (KIM-1), interleukin-18 (IL-18), and LTBP2. Further biomarkers useful in the present disclosure include inter alia B-type natriuretic peptide (BNP), pro-B-type natriuretic peptide (proBNP), amino terminal pro-B-type natriuretic peptide (NTproBNP) and C-reactive peptide, and fragments or precursors of any one thereof.

Hence, disclosed is a method for predicting, diagnosing and/or prognosticating the diseases or conditions as taught herein in a subject comprising the steps: (i) measuring the quantity of PERLECAN and the presence or absence and/or quantity of said one or more other biomarkers in the sample from the subject; (ii) using the measurements of (i) to establish a subject profile of the quantity of PERLECAN and the presence or absence and/or quantity of said one or more other biomarkers; (iii) comparing said subject profile of (ii) to a reference profile of the quantity of PERLECAN and the presence or absence and/or quantity of said one or more other biomarkers, said reference profile representing a known prediction, diagnosis and/or prognosis of the conditions, symptoms and/or parameter values according to the invention; (iv) finding a deviation or no deviation of the subject profile of (ii) from the reference profile; (v) attributing said finding of deviation or no deviation to a particular prediction, diagnosis and/or prognosis of the respective diseases or conditions in the subject.

Applying said method at two or more successive time points allows for monitoring the desired diseases or conditions.

The present methods may employ reference values for the quantity of PERLECAN, which may be established according to known procedures previously employed for other biomarkers. Such reference values may be established either within (i.e., constituting a step of) or external to (i.e., not constituting a step of) the methods of the present invention as defined herein. Accordingly, any one of the methods taught herein may comprise a step of establishing a reference value for the quantity of PERLECAN, said reference value representing either (a) a prediction or diagnosis of the absence of the diseases or as taught herein or a good prognosis thereof, or (b) a prediction or diagnosis of the diseases or conditions as taught herein or a poor prognosis thereof.

A further aspect provides a method for establishing a reference value for the quantity of PERLECAN, said reference value representing:
(a) a prediction or diagnosis of the absence of the diseases or conditions as taught herein or a good prognosis thereof, or
(b) a prediction or diagnosis of the diseases or conditions as taught herein or a poor prognosis thereof,
comprising:
(i) measuring the quantity of PERLECAN in:
 (i a) one or more samples from one or more subjects not having the respective diseases or conditions or not being at risk of having such or having a good prognosis for such, or
 (i b) one or more samples from one or more subjects having the respective diseases or conditions or being at risk of having such or having a poor prognosis for such, and
(ii) storing the quantity of PERLECAN
 (ii a) as measured in (i a) as the reference value representing the prediction or diagnosis of the absence of the respective diseases or conditions or representing the good prognosis therefore, or
 (ii b) as measured in (i b) as the reference value representing the prediction or diagnosis of the respective diseases or conditions or representing the poor prognosis therefore.

The present methods may otherwise employ reference profiles for the quantity of PERLECAN and the presence or absence and/or quantity of one or more other biomarkers, which may be established according to known procedures previously employed for other biomarkers. Such reference profiles may be established either within (i.e., constituting a step of) or external to (i.e., not constituting a step of) the present methods. Accordingly, the methods taught herein may comprise a step of establishing a reference profile for the quantity of PERLECAN and the presence or absence and/or quantity of said one or more other biomarkers, said reference profile representing either (a) a prediction or diagnosis of the absence of the diseases or conditions as taught herein or a good prognosis therefore, or (b) a prediction or diagnosis of the diseases or conditions as taught herein or a poor prognosis therefore.

A further aspect provides a method for establishing a reference profile for the quantity of PERLECAN and the presence or absence and/or quantity of one or more other biomarkers useful for predicting, diagnosing, prognosticating and/or monitoring the diseases or conditions as taught herein, said reference profile representing:
(a) a prediction or diagnosis of the absence of the respective diseases or conditions or a good prognosis therefore, or
(b) a prediction or diagnosis of the respective diseases or conditions or a poor prognosis therefore,
comprising:
(i) measuring the quantity of PERLECAN and the presence or absence and/or quantity of said one or more other biomarkers in:
 (i a) one or more samples from one or more subjects not having the respective diseases or conditions or not being at risk of having such or having a good prognosis for such; or (i b) one or more samples from one or more subjects having the respective diseases or conditions or being at risk of having such or having a poor prognosis for such;

(ii)
- (ii a) using the measurements of (i a) to create a profile of the quantity of PERLECAN and the presence or absence and/or quantity of said one or more other biomarkers; or
- (ii b) using the measurements of (i b) to create a profile of the quantity of PERLECAN and the presence or absence and/or quantity of said one or more other biomarkers;

(iii)
- (iii a) storing the profile of (ii a) as the reference profile representing the prediction or diagnosis of the absence of the respective diseases or conditions or representing the good prognosis therefore; or
- (iii b) storing the profile of (ii b) as the reference profile representing the prediction or diagnosis of the respective diseases conditions or representing the poor prognosis therefore.

Further provided is a method for establishing a PERLECAN base-line or reference value in a subject, comprising: (i) measuring the quantity of PERLECAN in the sample from the subject at different time points wherein the subject is not suffering from the diseases or conditions as taught herein, and (ii) calculating the range or mean value of the subject, which is the PERLECAN base-line or reference value for said subject.

Preferably, the subject as intended in any one of the present methods may be human.

The quantity of PERLECAN and/or the presence or absence and/or quantity of the one or more other biomarkers may be measured by any suitable technique such as may be known in the art. For example, the quantity of PERLECAN and/or the presence or absence and/or quantity of the one or more other biomarkers may be measured using, respectively, a binding agent capable of specifically binding to PERLECAN and/or to fragments thereof, and a binding agent capable of specifically binding to said one or more other biomarkers. For example, the binding agent may be an antibody, aptamer, photoaptamer, protein, peptide, peptidomimetic or a small molecule. For example, the quantity of PERLECAN and/or the presence or absence and/or quantity of the one or more other biomarkers may be measured using an immunoassay technology or a mass spectrometry analysis method or a chromatography method, or a combination of said methods.

Further disclosed is a kit for predicting, diagnosing, prognosticating and/or monitoring the diseases or conditions as taught herein in a subject, the kit comprising (i) means for measuring the quantity of PERLECAN in a sample from the subject, and optionally and preferably (ii) a reference value of the quantity of PERLECAN or means for establishing said reference value, wherein said reference value represents a known prediction, diagnosis and/or prognosis of the respective diseases or conditions. The kit thus allows one to: measure the quantity of PERLECAN in the sample from the subject by means (i); compare the quantity of PERLECAN measured by means (i) with the reference value of (ii) or established by means (ii); find a deviation or no deviation of the quantity of PERLECAN measured by means (i) from the reference value of (ii); and consequently attribute said finding of deviation or no deviation to a particular prediction, diagnosis and/or prognosis of the respective diseases or conditions in the subject.

A further embodiment provides a kit for predicting, diagnosing, prognosticating and/or monitoring the diseases or conditions as taught herein in a subject, the kit comprising (i) means for measuring the quantity of PERLECAN in a sample from the subject and (ii) means for measuring the presence or absence and/or quantity of one or more other biomarkers in the sample from the subject, and optionally and preferably (iii) means for establishing a subject profile of the quantity of PERLECAN and the presence or absence and/or quantity of said one or more other biomarkers, and optionally and preferably (iv) a reference profile of the quantity of PERLECAN and the presence or absence and/or quantity of said one or more other biomarkers, or means for establishing said reference profile, said reference profile representing a known prediction, diagnosis and/or prognosis of the conditions, symptoms and/or parameter values according to the invention. Such kit thus allows one to: measure the quantity of PERLECAN and the presence or absence and/or quantity of said one or more other biomarkers in the sample from the subject by respectively means (i) and (ii); establish (e.g., using means included in the kit or using suitable external means) a subject profile of the quantity of PERLECAN and the presence or absence and/or quantity of said one or more other biomarkers based on said measurements; compare the subject profile with the reference profile of (iv) or established by means (iv); find a deviation or no deviation of said subject profile from said reference profile; and consequently attribute said finding of deviation or no deviation to a particular prediction, diagnosis and/or prognosis of the respective diseases or conditions in the subject.

The means for measuring the quantity of PERLECAN and/or the presence or absence and/or quantity of the one or more other biomarkers in the present kits may comprise, respectively, one or more binding agents capable of specifically binding to PERLECAN and/or to fragments thereof, and one or more binding agents capable of specifically binding to said one or more other biomarkers. For example, any one of said one or more binding agents may be an antibody, aptamer, photoaptamer, protein, peptide, peptidomimetic or a small molecule. For example, any one of said one or more binding agents may be advantageously immobilised on a solid phase or support. The means for measuring the quantity of PERLECAN and/or the presence or absence and/or quantity of the one or more other biomarkers in the present kits may employ an immunoassay technology or mass spectrometry analysis technology or chromatography technology, or a combination of said technologies.

Disclosed is thus also a kit for predicting, diagnosing, prognosticating and/or monitoring the diseases or conditions as taught herein comprising: (a) one or more binding agents capable of specifically binding to PERLECAN and/or to fragments thereof; (b) preferably, a known quantity or concentration of PERLECAN and/or a fragment thereof (e.g., for use as controls, standards and/or calibrators); (c) preferably, a reference value of the quantity of PERLECAN, or means for establishing said reference value. Said components under (a) and/or (c) may be suitably labelled as taught elsewhere in this specification.

Also disclosed is a kit for predicting, diagnosing and/or prognosticating the diseases or conditions as taught herein comprising: (a) one or more binding agents capable of specifically binding to PERLECAN and/or to fragments thereof; (b) one or more binding agents capable of specifically binding to one or more other biomarkers; (c) preferably, a known quantity or concentration of PERLECAN and/or a fragment thereof and a known quantity or concentration of said one or more other biomarkers (e.g., for use as controls, standards and/or calibrators); (d) preferably, a reference profile of the quantity of PERLECAN and the presence or absence and/or quantity of said one or more other biomarkers, or means for establishing said reference profiles. Said components under (a), (b) and/or (c) may be suitably labelled as taught elsewhere in this specification.

Further disclosed is the use of the kit as described herein for diagnosing, predicting, prognosticating and/or monitoring the diseases or conditions as taught herein.

Also disclosed are reagents and tools useful for measuring PERLECAN and optionally the one or more other biomarkers concerned herein.

Hence, disclosed is a protein, polypeptide or peptide array or microarray comprising (a) PERLECAN and/or a fragment thereof, preferably a known quantity or concentration of said PERLECAN and/or fragment thereof; and (b) optionally and preferably, one or more other biomarkers, preferably a known quantity or concentration of said one or more other biomarkers.

Also disclosed is a binding agent array or microarray comprising: (a) one or more binding agents capable of specifically binding to PERLECAN and/or to fragments thereof, preferably a known quantity or concentration of said binding agents; and (b) optionally and preferably, one or more binding agents capable of specifically binding to one or more other biomarkers, preferably a known quantity or concentration of said binding agents.

Also disclosed are kits as taught here above configured as portable devices, such as, for example, bed-side devices, for use at home or in clinical settings.

A related aspect thus provides a portable testing device capable of measuring the quantity of PERLECAN in a sample from a subject comprising: (i) means for obtaining a sample from the subject, (ii) means for measuring the quantity of PERLECAN in said sample, and (iii) means for visualising the quantity of PERLECAN measured in the sample.

In an embodiment, the means of parts (ii) and (iii) may be the same, thus providing a portable testing device capable of measuring the quantity of PERLECAN in a sample from a subject comprising (i) means for obtaining a sample from the subject; and (ii) means for measuring the quantity of PERLECAN in said sample and visualising the quantity of PERLECAN measured in the sample.

In an embodiment, said visualising means is capable of indicating whether the quantity of PERLECAN in the sample is above or below a certain threshold level and/or whether the quantity of PERLECAN in the sample deviates or not from a reference value of the quantity of PERLECAN, said reference value representing a known prediction, diagnosis and/or prognosis of the diseases or conditions as taught herein. Hence, the portable testing device may suitably also comprise said reference value or means for establishing the reference value.

In an embodiment, the threshold level is chosen such that the quantity of PERLECAN in the sample above said threshold level indicates that the subject has or is at risk of having the respective disease or condition or indicates a poor prognosis for such in the subject, and the quantity of PERLECAN in the sample below said threshold level indicates that the subject does not have or is not at risk of having the diseases or conditions as taught herein or indicates a good prognosis for such in the subject.

In an embodiment, the portable testing device comprises a reference value representing the prediction or diagnosis of the absence of the diseases or conditions as taught herein or representing a good prognosis for such, or comprises means for establishing said reference value, and an elevated quantity of PERLECAN in the sample from the subject compared to said reference value indicates that the subject has or is at risk of having the respective disease or condition or indicates a poor prognosis for such in the subject. In another embodiment, the portable testing device comprises a reference value representing the prediction or diagnosis of the diseases or conditions as taught herein or representing a poor prognosis for such, or comprises means for establishing said reference value, and a comparable quantity of PERLECAN in the sample from the subject compared to said reference value indicates that the subject has or is at risk of having the respective disease or condition or indicates a poor prognosis for such in the subject.

In a further embodiment, the measuring (and optionally visualisation) means of the portable testing device may comprise a solid support having a proximal and distal end, comprising:—a sample application zone in the vicinity of the proximal end;—a reaction zone distal to the sample application zone; and—a detection zone distal to the reaction zone;—optionally control standards comprising PERLECAN protein or peptide fragments, whereby said support has a capillary property that directs a flow of fluid sample applied in the application zone in a direction from the proximal end to the distal end; and—optionally comprising a fluid source improving the capillary flow of a more viscous sample.

The reaction zone may comprise one or more bands of a PERLECAN-specific binding molecules conjugated to a detection agent, which PERLECAN specific binding molecule conjugate is disposed on the solid support such that it can migrate with the capillary flow of fluid; and wherein the detection zone comprises one or more capture bands comprising a population of PERLECAN specific molecule immobilised on the solid support.

The reaction zone may additionally comprise one or more bands of capture PERLECAN-specific binding molecules in an amount sufficient to prevent a threshold quantity of PERLECAN specific binding molecule conjugates to migrate to the detection zone. Alternatively, said device additionally comprises means for comparing the amount of captured PERLECAN specific binding molecule conjugate with a threshold value.

Other aspects relate to the realisation that PERLECAN may be a valuable target for therapeutic and/or prophylactic interventions in diseases and conditions as taught herein, in particular but without limitation including renal dysfunction, dyspnea associated with or caused by renal failure, increased mortality of subjects having dyspnea and/or acute heart failure and/or renal dysfunction, left ventricular hypertrophy, cardiac fibrosis, PE and PAP.

Hence, also disclosed herein are any one and all of the following:

(1) an agent that is able to modulate the level and/or the activity of PERLECAN for use as a medicament, preferably for use in the treatment of any one disease or condition as taught herein;

(2) use of an agent that is able to modulate the level and/or the activity of PERLECAN for the manufacture of a medicament for the treatment of any one disease or condition as taught herein; or use of an agent that is able to modulate the level and/or the activity of PERLECAN for the treatment of any one disease or condition as taught herein;

(3) a method for treating any one disease or condition as taught herein in a subject in need of such treatment, comprising administering to said subject a therapeutically or prophylactically effective amount of an agent that is able to modulate the level and/or the activity of PERLECAN;

(4) The subject matter as set forth in any one of (1) to (3) above, wherein the agent is able to reduce or increase the level and/or the activity of PERLECAN, preferably to reduce the level and/or the activity of PERLECAN.

(5) The subject matter as set forth in any one of (1) to (4) above, wherein said agent is able to specifically bind to PERLECAN.

(6) The subject matter as set forth in any one of (1) to (5) above, wherein said agent is an antibody or a fragment or derivative thereof; a polypeptide; a peptide; a peptidomimetic; an aptamer; a photoaptamer; or a chemical substance, preferably an organic molecule, more preferably a small organic molecule.

(7) The subject matter as set forth in any one of (1) to (4) above, wherein the agent is able to reduce or inhibit the expression of PERLECAN, preferably wherein said agent is an antisense agent; a ribozyme; or an agent capable of causing RNA interference.

(8) The subject matter as set forth in any one of (1) to (4) above, wherein said agent is able to reduce or inhibit the level and/or activity of PERLECAN, preferably wherein said agent is a recombinant or isolated deletion construct of the PERLECAN polypeptide having a dominant negative activity over the native PERLECAN.

(9) An assay to select, from a group of test agents, a candidate agent potentially useful in the treatment of any one disease or condition as taught herein, said assay comprising determining whether a tested agent can modulate, such as increase or reduce and preferably reduce, the level and/or activity of PERLECAN.

(10) The assay as set forth in (9) above, further comprising use of the selected candidate agent for the preparation of a composition for administration to and monitoring the prophylactic and/or therapeutic effect thereof in a non-human animal model, preferably a non-human mammal model, of any one disease or condition as taught herein.

(11) The agent isolated by the assay as set forth in (10) above.

(12) A pharmaceutical composition or formulation comprising a prophylactically and/or therapeutically effective amount of one or more agents as set forth in any one of (1) to (8) or (10) above, or a pharmaceutically acceptable N-oxide form, addition salt, prodrug or solvate thereof, and further comprising one or more of pharmaceutically acceptable carriers.

(13) A method for producing the pharmaceutical composition or formulation as set forth in (12) above, comprising admixing said one or more agents with said one or more pharmaceutically acceptable carriers.

Said condition or disease as set forth in any one of (1) to (13) above may be particularly chosen from renal dysfunction, dyspnea associated with or caused by renal failure, increased mortality of subjects having dyspnea and/or acute heart failure and/or renal dysfunction, left ventricular hypertrophy, cardiac fibrosis, PE and PAP.

Also contemplated is thus a method (a screening assay) for selecting an agent capable of specifically binding to PERLECAN (e.g., gene or protein) comprising: (a) providing one or more, preferably a plurality of, test PERLECAN-binding agents; (b) selecting from the test PERLECAN-binding agents of (a) those which bind to PERLECAN; and (c) counter-selecting (i.e., removing) from the test PERLECAN-binding agents selected in (b) those which bind to any one or more other, unintended or undesired, targets.

Alternatively, one could envisage an inhibitor of the molecules responsible for the processing of the PERLECAN molecule or fragment thereof such as inhibitors of the Cathepsin L enzyme, which has been shown to cleave the LG3 fragment from the endorepellin fragment of PERLECAN. Some CathL inhibitors are commercially available. Non-limiting examples are: ZFF-FMK (Calbiochem) and ZFA-FMK (MP Biomedicals), which are irreversible and cell-permeable CathL inhibitors.

Binding between test PERLECAN-binding agents and PERLECAN may be advantageously tested by contacting (i.e., combining, exposing or incubating) said PERLECAN with the test PERLECAN-binding agents under conditions generally conducive for such binding. For example and without limitation, binding between test PERLECAN-binding agents and the PERLECAN may be suitably tested in vitro; or may be tested in host cells or host organisms comprising the PERLECAN and exposed to or configured to express the test PERLECAN-binding agents.

Without limitation, the PERLECAN-binding or PERLECAN-modulating agents may be capable of binding PERLECAN or modulating the activity and/or level of the PERLECAN in vitro, in a cell, in an organ and/or in an organism.

In the screening assays as set forth in any one of (9) and (10) above, modulation of the activity and/or level of the PERLECAN by test PERLECAN-modulating agents may be advantageously tested by contacting (i.e., combining, exposing or incubating) said PERLECAN (e.g., gene or protein) with the test PERLECAN-modulating agents under conditions generally conducive for such modulation. By means of example and not limitation, where modulation of the activity and/or level of the PERLECAN results from binding of the test PERLECAN-modulating agents to the PERLECAN, said conditions may be generally conducive for such binding. For example and without limitation, modulation of the activity and/or level of the PERLECAN by test PERLECAN-modulating agents may be suitably tested in vitro; or may be tested in host cells or host organisms comprising the LPBT2 and exposed to or configured to express the test PERLECAN-modulating agents.

As well contemplated are:
PERLECAN for use as a medicament, preferably for use in the treatment of any one disease or condition as taught herein;
use of PERLECAN for the manufacture of a medicament for the treatment of any one disease or condition as taught herein;
use of PERLECAN for the treatment of any one disease or condition as taught herein;
a method for treating any one disease or condition as taught herein in a subject in need of such treatment, comprising administering to said subject a therapeutically or prophylactically effective amount of PERLECAN;
particularly wherein said condition or disease may be chosen from renal dysfunction, dyspnea associated with or caused by renal failure, increased mortality of subjects having dyspnea and/or acute heart failure and/or renal dysfunction, left ventricular hypertrophy, cardiac fibrosis, PE and PAP.

These and further aspects and preferred embodiments are described in the following sections and in the appended claims.

BRIEF DESCRIPTION OF THE DRAWINGS

FIGS. 1A-1G illustrate PERLECAN sequences. FIG. 1A shows the sequences of full length PERLECAN (SEQ ID NO.1). The underlined part depicts the endorepellin domain (SEQ ID NO. 2; FIG. 1B) and the bold underlined part depicts the LG-3 domain (SEQ ID NO.3; FIG. 1C). The peptides detected by the MASSterclass™ or MASStermind™ technology are double underligned (SEQ ID No's 4 and 5 respectively shown as FIGS. 1D and 1E).

FIGS. 2A and 2B illustrate correlation of PERLECAN levels with estimated glomerular filtration rate (eGFR) (FIG. 2A) and Cystatin C levels (FIG. 2B) in all 154 patients.

FIG. 3A illustrates box and whisker plots of relative amounts of perlecan as measured by MASSterclass in a patient group with kidney failure versus a control group with no kidney failure. FIG. 3B shows that PERLECAN shows comparable performance to Cystatin C in discriminating patients with reduced eGFR (herein <60 ml/min/1.73m$^2$) from patients with normal eGFR. Receiver operating characteristic curve of Cystatin C (solid line) compared to PERLECAN (hatched line). Calculated median area under the curve (AUC) and 95% confidence intervals are for Cystatin C: 0.94 (0.90-0.96) and for PERLECAN: 0.91 (0.83-0.97).

FIGS. 7A and 7B: FIG. 7A illustrates a schematic overview of PERLECAN and its derived active peptides endorepellin and LG3 as well as the different peptides used for MASSterclass quantitation. Further the correlation of MASSterclass read-outs based on Seq ID No: 7 (FIG. 7A) and Seq ID No: 4 and 6 (FIG. 7B) with eGfr are shown.

DETAILED DESCRIPTION

Figure 2A:
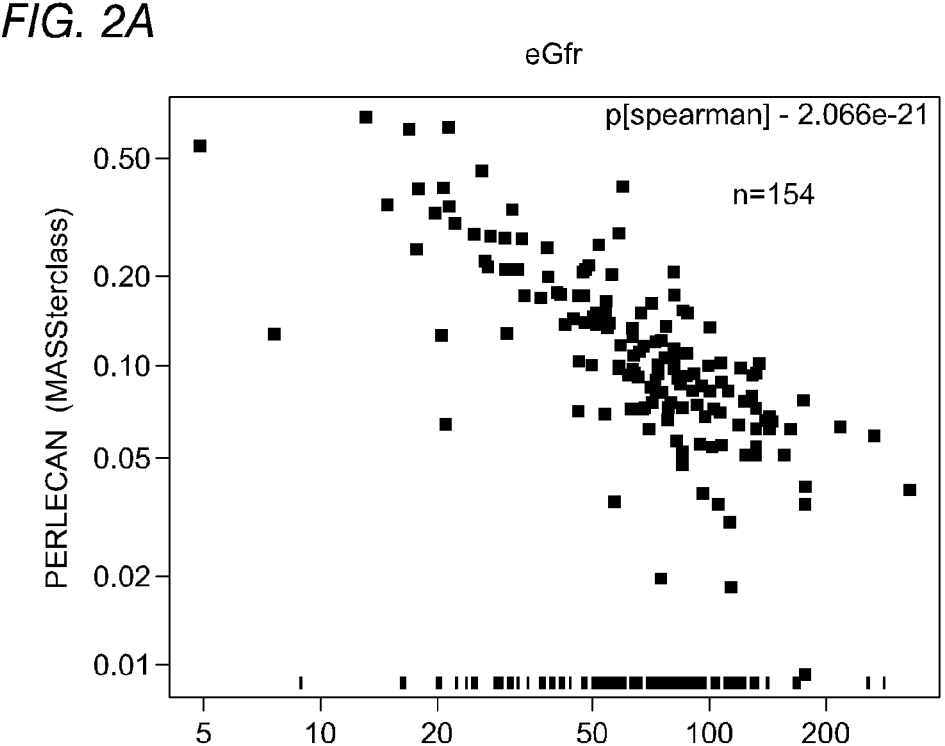
FIGS. 2A and 2B.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

The inventors show that PERLECAN is a valuable biomarker particularly for renal (dys)function and mortality in subjects having dyspnea and/or acute heart failure and/or renal dysfunction, and further for left ventricular hypertrophy, cardiac fibrosis, preeclampsia (PE) and pregnancy-associated proteinuria (PAP).

The term "biomarker" is widespread in the art and may broadly denote a biological molecule and/or a detectable portion thereof whose qualitative and/or quantitative evaluation in a subject is predictive or informative (e.g., predictive, diagnostic and/or prognostic) with respect to one or more aspects of the subject's phenotype and/or genotype, such as, for example, with respect to the status of the subject as to a given disease or condition.

Reference herein to "disease(s) and/or condition(s) as taught herein" or a similar reference encompasses any such diseases and conditions as disclosed herein insofar consistent with the context of such a recitation, in particular but without limitation including renal dysfunction, dyspnea associated with or caused by renal failure, increased mortality of subjects having dyspnea and/or acute heart failure and/or renal dysfunction, left ventricular hypertrophy, cardiac fibrosis, PE, proteinuria, e.g. proteinuria associated with pregnancy (PAP), or with metabolic syndrome or with Type II diabetes.

Renal or kidney dysfunction, which may also be interchangeably known as renal or kidney failure or insufficiency, generally encompasses states, diseases and conditions in which the functioning of renal tissue is inadequate, particularly wherein kidney excretory function is compromised.

Signs and symptoms of renal dysfunction may include without limitation any one or more of increased levels of urea and/or nitrogen in the blood; lower than normal creatinine clearance and higher than normal creatinine levels in blood; lower than normal free water clearance; volume overload and swelling; abnormal acid levels; higher than normal levels of potassium, calcium and/or phosphate in blood; changes in urination (e.g., volume, osmolarity); microalbuminuria or macroalbuminuria; altered activity of kidney enzymes such as gamma glutamyl synthetase; fatigue; skin rash or itching; nausea; dyspnea; reduced kidney size; haematuria and anaemia.

Conventionally, renal dysfunction is deemed as comprising major classes denoted as acute renal or kidney failure (acute renal or kidney disease or injury, e.g., acute kidney injury or "AKI") or chronic renal or kidney failure (chronic renal or kidney disease). Whereas progression is typically fast (e.g., days to weeks) in acute renal failure, renal failure may be traditionally regarded as chronic if it persists for at least 3 months and its progression may take in the range of years.

Acute renal dysfunction or failure may be staged (classified, graded) into 5 distinct stages using the "RIFLE" (Risk, Injury, Failure, Loss, end-stage renal disease) staging system as set out here below (based on Lameire et al. 2005, Lancet 365: 417-430):

| Stage | GFR (based on serum creatinine) criteria GFR = glomerular filtration rate | Urine output criteria |
| --- | --- | --- |
| "Risk" | Serum creatinine increased 1.5 times | <0.5 mL/kg/h for 6 h |
| "Injury" | Serum creatinine increased 2.0 times | <0.5 mL/kg/h for 12 h |
| "Failure" | Serum creatinine increased 3.0 times, or creatinine >355 mM/L when there was an acute rise of >44 mM/L | <0.3 mL/kg/h for 24 h or anuria for 12 h |
| "Loss" | Persistent acute renal failure >4 weeks | — |
| "End-stage" | End-stage renal disease >3 months | — |

Chronic renal dysfunction or failure may be staged (classified, graded) based on GFR as set out here below (based on Levey et al. 2005, Kidney Int 67: 2089-2100):
Stage 1: GFR≧90 mL/min (normal or elevated GFR)
Stage 2: GFR=60-89 mL/min (mild GFR reduction)
Stage 3: GFR=30-59 mL/min (moderate GFR reduction)
Stage 4: GFR=15-29 mL/min (severe GFR reduction)
Stage 5: GFR<15 mL/min (renal failure)

Other staging methods for renal failure resulting in similar or comparable classifications of different stages of renal failure may be used herein.

The present diagnosis, prediction, prognosis and/or monitoring methods may allow to determine that a subject has or is at risk of having acute or chronic renal failure, such as in particular determine any one of the above-described or comparable stages of acute or chronic renal failure in the subject, and/or may allow to discriminate between said stages in the subject.

The causes of acute renal deterioration may be pre-renal, post-renal and/or intra-renal. Pre-renal causes include lack of sufficient blood supply to the kidneys (i.e., renal hypoperfusion), which in turn may be caused by inter alia haemorrhage, massive blood loss, congestive heart failure, decompensated liver cirrhosis (liver cirrhosis with complications such as bleedings, ascites), damaged kidney blood vessels, sepsis or systemic inflammation due to infection. Patients that underwent a surgical or operative treatment sometimes suffer from acute kidney injury (AKI), resulting in a temporary loss or reduction of the function of the kidneys. Post-renal causes include obstructions of urine collection systems or extra-renal drainage (i.e., obstructive uropathy), which in turn may be caused by inter alia medication interfering with normal bladder emptying, prostate diseases, kidney stones, abdominal malignancy (such as ovarian cancer or colorectal cancer), or obstructed urinary catheter. Intra-renal causes include renal tissue-destroying conditions, such as vasculitis, malignant hypertension, acute glomerulonephritis, acute interstitial nephritis and acute tubular necrosis. They can be caused without limitation by ischemic events (such as, e.g., haemoglobinuria, myoglobinuria and myoloma) or by nephrotoxic substances (such as, e.g., antibiotics, radio contrast agents, uric acid, oxalate and drug induced renal toxicity). Subjects having or being at risk of having the above states, conditions or diseases may have or may be at risk of developing acute renal failure. Hence, the present diagnosis, prediction, prognosis and/or monitoring methods may be preferably employed in such patients.

Causes of chronic renal deterioration may include inter alia vascular diseases, such as, e.g., bilateral renal artery stenosis, ischemic nephropathy, haemolytic-uremic syndrome and vasculitis, and further focal segmental nephrosclerosis, glomerulosclerosis, glomerulonephritis, IgA nephritis, diabetic nephropathy, lupus nephritis, polycystic kidney disease, chronic tubulointerstitial nephritis (e.g., drug and/or toxin-induced), renal fibrosis, kidney stones, and prostate diseases. Subjects having or being at risk of having the above states, conditions or diseases may have or may be at risk of developing chronic renal failure. Proteinuria, essentially the abnormal presence of proteins in the urine of a subject, can be a sign of renal dysfunction and occurs in many disorders such nephrotic syndromes, nephropathys, glomerular diseases, such as membranous glomerulonephritis, focal segmental glomerulonephritis, minimal change disease (lipoid nephrosis), Eeclampsia or Preclampsia (PE) and Pregnancy associated Proteinuria (PAP), Type II diabetes etc. Type II diabetes develops in obese/metabolic syndrome patients. These patients typically develop glomerulus damage (inflammation, hypertension, metabolic changes etc) to end up with a reduced GFR and proteinuria. Very typical for these patients is that the reduced GFR is preceded by a hyperfiltration phase.

Postoperative patients are prone to develop kidney related problems, mostly apparent as acute kidney injury (AKI). Further a significant percentage of these patients require haemodialysis or renal replacement therapy (RRT) in the days following surgery, this to attain solute clearance and fluid balance while waiting for kidney function to recover. Timely institution of RRT is fundamental to achieve this goal. When no supportive therapy is started timely, the kidneys may suffer permanent damage and not recover fully. Current indications for RRT include persistent hyperkalemia, severe acidosis and hypervolemia that are unresponsive to conservative measures. Early RRT is used to describe the initiation of dialysis therapy before nitrogenous waste products reach some arbitrarily predefined "critical" blood value, irrespective of clinical indications. A meta-analysis shows that early institution of RRT might be associated with improved outcomes (i.e. decreased mortality) in patients with AKI (Seabra et al., 2008; American Journal of Kidney diseases; Vol 52 (2), 272-284). Clearly, when a patients is put on RRT before the traditional creatinin or urea based time point survival is improved. While creatinin or urea levels are currently used for deciding upon starting RRT, there is currently no good criterion for early RRT intervention. There is no objective early measure for the need of early RRT initiation and a biomarker that can specifically identify those patients that will benefit from early RRT is warranted.

The present invention provides for a new biomarker, Perlecan, especially its endorepellin region, more in particular its LG3 region, for the early establishment as to whether a patient requires RRT.

Hence, the present diagnosis, prediction, prognosis and/or monitoring methods may be preferably employed preferably in the types of patients listed above.

Dyspnea (dyspnoea or shortness of breath) is known per se and may particularly refer to a common and distressing symptom experienced by subjects as unpleasant or uncomfortable respiratory sensations, that may be more particularly defined as a "subjective experience of breathing discomfort that consists of qualitatively distinct sensations that vary in intensity". Dyspnea may be connected to a range of underlying pathologies.

The terms "heart failure", "acute heart failure" and "chronic heart failure" as used herein carry their respective art-established meanings. By means of further guidance, the term "heart failure" as used herein broadly refers to pathological conditions characterised by an impaired diastolic or systolic blood flow rate and thus insufficient blood flow from the ventricle to peripheral organs.

"Acute heart failure" or also termed "acute decompensated heart failure" may be defined as the rapid onset of symptoms and signs secondary to abnormal cardiac function, resulting in the need for urgent therapy. AHF can present itself acute de novo (new onset of acute heart failure in a patient without previously known cardiac dysfunction) or as acute decompensation of CHF.

The cardiac dysfunction may be related to systolic or diastolic dysfunction, to abnormalities in cardiac rhythm, or to preload and afterload mismatch. It is often life threatening and requires urgent treatment. According to established classification, AHF includes several distinct clinical conditions of presenting patients: (I) acute decompensated congestive heart failure, (II) AHF with hypertension/hypertensive crisis, (III) AHF with pulmonary oedema, (IVa) cardiogenic shock/low output syndrome, (IVb) severe cardiogenic shock, (V) high output failure, and (VI) right-sided acute heart failure. For detailed clinical description, classification and diagnosis of AHF, and for summary of further AHF classification systems including the Killip classification, the Forrester classification and the 'clinical severity' classification, refer inter alia to Nieminen et al. 2005 ("Executive summary of the guidelines on the diagnosis and treatment of acute heart failure: the Task Force on Acute Heart Failure of the European Society of Cardiology". Eur Heart J 26: 384-416) and references therein.

The term "chronic heart failure" (CHF) generally refers to a case of heart failure that progresses so slowly that various compensatory mechanisms work to bring the disease into equilibrium. Common clinical symptoms of CHF include inter alia any one or more of breathlessness, diminishing exercise capacity, fatigue, lethargy and peripheral oedema. Other less common symptoms include any one or more of palpitations, memory or sleep disturbance and confusion, and usually co-occur with one or more of the above recited common symptoms.

Left ventricular hypertrophy (LVH) generally encompasses the thickening of the myocardium of the left ventricle of the heart. LVH may represent a pathological reaction to cardiovascular diseases that increase the afterload (e.g., aortic stenosis or aortic insufficiency) or high blood pressure. LVH may also represent primary hypertrophic cardiomyopathy. LVH diagnosis may be made inter alia using echocardiography, using criteria known per se such as the Sokolow-Lyon index, the Cornell voltage criteria, the Romhilt-Estes point score system or other voltage-based criteria.

Cardiac fibrosis generally encompasses abnormal thickening of the heart valves due to inappropriate proliferation of cardiac fibroblasts and the concomitant excessive production of matrix proteins.

By "preeclampsia" (PE or pre-eclampsia) is meant the multi-system disorder that is characterised by hypertension with proteinuria or oedema, or both, glomerular dysfunction, brain oedema, liver oedema, or coagulation abnormalities due to pregnancy or the influence of a recent pregnancy and all complications associated with the disorder. Pre-eclampsia generally occurs after the 20th week of gestation. Pre-eclampsia is generally defined as some combination of the following symptoms:
(1) a systolic blood pressure (BP)>140 mmHg and a diastolic BP>90 mmHg after 20 weeks gestation (generally measured on two occasions, 4-168 hours apart),
(2) new onset proteinuria (1+ by dipstick on urinanalysis, >300 mg of protein in a 24-hour urine collection, or a single random urine sample having a protein/creatinine ratio >0.3), and
(3) resolution of hypertension and proteinuria by 12 weeks postpartum.

Severe pre-eclampsia is generally defined as (1) a diastolic BP>110 mmHg (generally measured on two occasions, 4-168 hours apart) or (2) proteinuria characterised by a measurement of 3.5 g or more protein in a 24-hour urine collection or two random urine specimens with at least 3+protein by dipstick. In pre-eclampsia, hypertension and proteinuria generally occur within seven days of each other. In severe pre-eclampsia, severe hypertension, severe proteinuria and HELLP syndrome (haemolysis, elevated liver enzymes, low platelets) or eclampsia can occur simultaneously or only one symptom at a time. Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral oedema and cerebral haemorrhage). The aetiology of the seizures is thought to be secondary to the development of cerebral oedema and focal spasm of small blood vessels in the kidney. Preeclampsia is associated with foetal complications such as intrauterine growth retardation (IUGR) and small for gestational age (SGA). By "small for gestational age (SGA)" is meant a foetus whose birth weight is a weight less than 2,500 gm or below the 10th percentile for gestational age according to U.S.

tables of birth weight for gestational age by race, parity, and infant sex as defined by World Health Organization (WHO) (Zhang and Bowes 1995, Obstet Gynecol 86: 200-208).

The terms "predicting" or "prediction", "diagnosing" or "diagnosis" and "prognosticating" or "prognosis" are commonplace and well-understood in medical and clinical practice. It shall be understood that the phrase "a method for predicting, diagnosing and/or prognosticating" a given disease or condition may also be interchanged with phrases such as "a method for prediction, diagnosis and/or prognosis" of said disease or condition or "a method for making (or determining or establishing) a prediction, diagnosis and/or prognosis" of said disease or condition, or the like.

By means of further explanation and without limitation, "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

The terms "diagnosing" or "diagnosis" generally refer to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition). As used herein, "diagnosis of" the diseases or conditions as taught herein in a subject may particularly mean that the subject has such, hence, is diagnosed as having such. "Diagnosis of no" diseases or conditions as taught herein in a subject may particularly mean that the subject does not have such, hence, is diagnosed as not having such. A subject may be diagnosed as not having such despite displaying one or more conventional symptoms or signs reminiscent of such.

The terms "prognosticating" or "prognosis" generally refer to an anticipation on the progression of a disease or condition and the prospect (e.g., the probability, duration, and/or extent) of recovery.

A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period.

A poor prognosis of the diseases or conditions as taught herein may generally encompass anticipation of a substandard recovery and/or unsatisfactorily slow recovery, or to substantially no recovery or even further worsening of such.

The term "subject" or "patient" as used herein typically denotes humans, but may also encompass reference to non-human animals, preferably warm-blooded animals, more preferably mammals, such as, e.g., non-human primates, rodents, canines, felines, equines, ovines, porcines, and the like.

The terms "sample" or "biological sample" as used herein include any biological specimen obtained from a subject. Samples may include, without limitation, whole blood, plasma, serum, red blood cells, white blood cells (e.g., peripheral blood mononuclear cells), saliva, urine, stool (i.e., faeces), tears, sweat, sebum, nipple aspirate, ductal lavage, tumour exudates, synovial fluid, cerebrospinal fluid, lymph, fine needle aspirate, amniotic fluid, any other bodily fluid, cell lysates, cellular secretion products, inflammation fluid, semen and vaginal secretions. Preferred samples may include ones comprising PERLECAN protein in detectable quantities. In preferred embodiments, the sample may be whole blood or a fractional component thereof such as, e.g., plasma, serum, or a cell pellet. Preferably the sample is readily obtainable by minimally invasive methods, allowing to remove or isolate said sample from the subject. Samples may also include tissue samples and biopsies, tissue homogenates and the like. Preferably, the sample used to detect PERLECAN levels is blood plasma. Also preferably, the sample used to detect PERLECAN levels is urine. The term "plasma" defines the colorless watery fluid of the blood that contains no cells, but in which the blood cells (erythrocytes, leukocytes, thrombocytes, etc.) are suspended, containing nutrients, sugars, proteins, minerals, enzymes, etc.

A molecule or analyte such as a protein, polypeptide or peptide, or a group of two or more molecules or analytes such as two or more proteins, polypeptides or peptides, is "measured" in a sample when the presence or absence and/or quantity of said molecule or analyte or of said group of molecules or analytes is detected or determined in the sample, preferably substantially to the exclusion of other molecules and analytes.

The terms "quantity", "amount" and "level" are synonymous and generally well-understood in the art. The terms as used herein may particularly refer to an absolute quantification of a molecule or an analyte in a sample, or to a relative quantification of a molecule or analyte in a sample, i.e., relative to another value such as relative to a reference value as taught herein, or to a range of values indicating a base-line expression of the biomarker. These values or ranges can be obtained from a single patient or from a group of patients.

An absolute quantity of a molecule or analyte in a sample may be advantageously expressed as weight or as molar amount, or more commonly as a concentration, e.g., weight per volume or mol per volume.

A relative quantity of a molecule or analyte in a sample may be advantageously expressed as an increase or decrease or as a fold-increase or fold-decrease relative to said another value, such as relative to a reference value as taught herein. Performing a relative comparison between first and second parameters (e.g., first and second quantities) may but need not require to first determine the absolute values of said first and second parameters. For example, a measurement method can produce quantifiable readouts (such as, e.g., signal intensities) for said first and second parameters, wherein said readouts are a function of the value of said parameters, and wherein said readouts can be directly compared to produce a relative value for the first parameter vs. the second parameter, without the actual need to first convert the readouts to absolute values of the respective parameters.

As used herein, the term "PERLECAN" corresponds to the protein commonly known as PERLECAN (PLC), also known as heparan sulfate proteoglycan 2 (HSPG2), sometimes abbreviated as SJA, SJS, SJS1, or PRCAN, i.e. the proteins and polypeptides commonly known under these designations in the art. The terms encompass such proteins and polypeptides of any organism where found, and particularly of animals, preferably vertebrates, more preferably mammals, including humans and non-human mammals, even more preferably of humans. The terms particularly encompass such proteins and polypeptides with a native sequence, i.e., ones of which the primary sequence is the same as that of PERLECAN found in or derived from nature. A skilled person understands that native sequences of PERLECAN may differ between different species due to genetic divergence between such species. Moreover, the native sequences of PERLECAN may differ between or within different individuals of the same species due to normal genetic diversity (variation) within a given species. Also, the native sequences of PERLECAN may differ between or even within different individuals of the same species due to post-transcriptional or post-translational modifications. Accordingly, all PERLECAN sequences found in or derived from nature are considered "native". The terms encompass PERLECAN proteins and polypeptides when forming a part of a living organism, organ, tissue or cell, when forming a part of a biological sample, as well as when at least partly isolated from such sources. The terms also encompass proteins and polypeptides when produced by recombinant or synthetic means.

Exemplary PERLECAN includes, without limitation, human PERLECAN having primary amino acid sequence as annotated under NCBI Genbank (http://www.ncbi.nlm.nih.gov/) accession number NP_005520 (sequence version 4), comprising 4391 amino acids as reproduced in FIG. 1 (SEQ ID NO: 1). A skilled person can also appreciate that said sequences are of precursor of PERLECAN and may include parts which are processed away from mature PERLECAN. For example, in FIG. 1, the C-terminal endorepellin (SEQ ID NO.2) and LG3 (SEQ ID NO. 3) domains are also indicated. The term "PERLECAN" as used herein encompasses full-length PERLECAN as well as fragments thereof. Preferred examples of such fragments are endorepellin and/or LG3.

In an embodiment the circulating PERLECAN, e.g., secreted form circulating in the blood plasma, may be detected, as opposed to the cell-bound or cell-confined PERLECAN protein.

The reference herein to PERLECAN may thus also encompass fragments of PERLECAN. Hence, the reference herein to measuring PERLECAN, or to measuring the quantity of PERLECAN, may encompass measuring the PERLECAN protein or polypeptide, such as, e.g., measuring the mature and/or the processed soluble/secreted form (e.g. plasma circulating form) of PERLECAN and/or measuring one or more fragments thereof, such as endorepellin and/or LG3. For example, PERLECAN and/or one or more fragments thereof may be measured collectively, such that the measured quantity corresponds to the sum amounts of the collectively measured species, by for example using a binding molecule that binds at the C-terminal end of PERLECAN. In another example, PERLECAN and/or one or more fragments thereof such as Endorepellin and/or LG3 may be measured each individually. Preferably, said fragment of PERLECAN is a plasma circulating form of PERLECAN. The expression "plasma circulating form of PERLECAN" or shortly "circulating form" encompasses all PERLECAN proteins or fragments thereof that circulate in the plasma, i.e., are not cell- or membrane-bound. Without wanting to be bound by any theory, such circulating forms can be derived from the full-length PERLECAN protein through natural processing, or can be resulting from known degradation processes occurring in said sample. In certain situations, the circulating form can also be the full-length PERLECAN protein, which is found to be circulating in the plasma. Said "circulating form" can thus be any PERLECAN protein or any processed soluble form of PERLECAN or fragments of either one, that is circulating in the sample, i.e. which is not bound to a cell- or membrane fraction of said sample. Exemplary fragments may be the processed Endorepellin or LG-3 peptides. It has for example been reported that the LG3 domain is cleaved from the Endorepellin domain by Cathepsin-L, during the process of apoptosis of endothelial cells (Cailhier et al., 2008, JBC Vol. 283(40):27220-27229).

Endorepellin and especially its LG3 peptide is known to be an angiogenesis inhibitor (Mongiat et al., 2003, JBC Vol. 278(6):4238-4249). Perlecan has for example been shown to be situated in the basement membrane of e.g. human placenta and decidua, where it appears to be important in maintaining blood vessel and villous integrity or modelling thereof (Chen et al., 2008, Placenta 29:309-316).

In the literature however, PERLECAN levels in the blood of human subjects has not been used or suggested for having a diagnostic value towards renal dysfunction. Although there are two publications that detected a PERLECAN fragment in urine of end-stage renal patients (Oda et al., Clinica Chimica Alta 255(1996):119-132), or chronic allograft nephropathy caused by acute rejection of a renal inplant (O'Riordan et al., 2008 Proteomics Clin. Appl. 2:1025-1035), it could not be anticipated that PERLECAN levels in blood samples could be indicative of renal failure. The publication actually reports on a new method for purifying low molecular weight proteins from urine of patients with end-stage renal disease. No indication is given that said peptide could be a diagnostic marker.

The peptides detected in the samples of the subjects according to the methods and use of the present invention are situated in the C-terminal part of PERLECAN, more precisely in the endorepellin domain, even more precisely in the LG-3 domain (cf. FIG. 1). Without wanting to be bound by any theory, an elevated PERLECAN level measured in the samples can thus be linked to an increase in general PERLECAN protein expression and/or in an increased proteolysis or processing of the PERLECAN protein, which is generally situated in the extracellular matrix, wherein the cleaved forms (e.g. endorepellin and/or LG-3) are released from the full-length molecule.

As used herein, the terms "pro-B-type natriuretic peptide" (also abbreviated as "proBNP") and "amino terminal pro-B-type natriuretic peptide" (also abbreviated as "NTproBNP") and "B-type natriuretic peptide" (also abbreviated as "BNP") refer to peptides commonly known under these designations in the art. As further explanation and without limitation, in vivo proBNP, NTproBNP and BNP derive from natriuretic peptide precursor B preproprotein (preproBNP). In particular, proBNP peptide corresponds to the portion of preproBNP after removal of the N-terminal secretion signal (leader) sequence from preproBNP. NTproBNP corresponds to the N-terminal portion and BNP corresponds to the C-terminal portion of the proBNP peptide subsequent to cleavage of the latter C-terminally adjacent to amino acid 76 of proBNP.

The term "Cystatin C", also known as ARMD11; MGC117328, Cystatin-3 (CST3), refers to peptides commonly known under these designations in the art, as exemplarily annotated under Genbank accession number NP_000090 (sequence version 1).

As used herein, "neutrophil gelatinase-associated lipocalin" or "NGAL", also known as oncogenic lipocalin 24P3, uterocalin or lipocalin 2 (LCN2), refers to peptides commonly known under these designations in the art, as exemplarily annotated under Genbank accession number NP_005555 (sequence version 2).

The term "C-reactive protein", also known as CRP or PTX1, refers to peptides commonly known under these designations in the art, as exemplarily annotated under Genbank accession number NP_000558 (sequence version 2).

The term "beta-trace protein", also known as inter alia prostaglandin-H2 D-isomerase, prostaglandin-D2 synthase, cerebrin-28 and PTGDS, refers to peptides commonly known under these designations in the art, as exemplarily annotated under Genbank accession number NP_000945 (sequence version 3).

The term "kidney injury molecule 1" or KIM-1 refers to peptides commonly known under these designations in the art, as exemplarily disclosed in Ichimura et al. 2004 (Am J Physiol Renal Physiol 286(3): F552-63) and Ichimura et al. 1998 (J Biol Chem 273: 4135-4142).

The term "interleukin-18" refers to peptides commonly known under this designation in the art, as exemplarily annotated under Genbank accession number NP_001553 (sequence version 1).

Unless otherwise apparent from the context, reference herein to any protein, polypeptide or peptide encompasses such from any organism where found, and particularly preferably from animals, preferably vertebrates, more preferably mammals, including humans and non-human mammals, even more preferably from humans.

Further, unless otherwise apparent from the context, reference herein to any protein, polypeptide or peptide and fragments thereof may generally also encompass modified forms of said protein, polypeptide or peptide and fragments such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

In an embodiment, PERLECAN and fragments thereof, or other biomarkers as employed herein and fragments thereof, may be human, i.e., their primary sequence may be the same as a corresponding primary sequence of or present in a naturally occurring human peptides, polypeptides or proteins. Hence, the qualifier "human" in this connection relates to the primary sequence of the respective proteins, polypeptides, peptides or fragments, rather than to their origin or source. For example, such proteins, polypeptides, peptides or fragments may be present in or isolated from samples of human subjects or may be obtained by other means (e.g., by recombinant expression, cell-free translation or non-biological peptide synthesis).

The term "fragment" of a protein, polypeptide or peptide generally refers to N-terminally and/or C-terminally deleted or truncated forms of said protein, polypeptide or peptide. The term encompasses fragments arising by any mechanism, such as, without limitation, by alternative translation, exo- and/or endo-proteolysis and/or degradation of said protein or polypeptide, such as, for example, in vivo or in vitro, such as, for example, by physical, chemical and/or enzymatic proteolysis. Without limitation, a fragment of a protein, polypeptide or peptide may represent at least about 5%, or at least about 10%, e.g., ≧20%, ≧30% or ≦40%, such as ≧50%, e.g., ≧60%, ≧70% or ≧80%, or even ≧90% or ≧95% of the amino acid sequence of said protein, polypeptide or peptide.

For example, a fragment may include a sequence of 5 consecutive amino acids, or 10 consecutive amino acids, or ≧20 consecutive amino acids, or ≧30 consecutive amino acids, e.g., ≧40 consecutive amino acids, such as for example ≧50 consecutive amino acids, e.g., ≧60, ≧70, ≧80, ≧90, ≧100, ≧200, ≧300, ≧400, ≧500 or ≧600 consecutive amino acids of the corresponding full length protein.

In an embodiment, a fragment may be N-terminally and/or C-terminally truncated by between 1 and about 20 amino acids, such as, e.g., by between 1 and about 15 amino acids, or by between 1 and about 10 amino acids, or by between 1 and about 5 amino acids, compared to the corresponding mature, full-length protein or its soluble or plasma circulating form. By means of example, proBNP, NTproBNP and BNP fragments useful as biomarkers are disclosed in WO 2004/094460.

In an embodiment, fragments of a given protein, polypeptide or peptide may be achieved by in vitro proteolysis of said protein, polypeptide or peptide to obtain advantageously detectable peptide(s) from a sample. For example, such proteolysis may be effected by suitable physical, chemical and/or enzymatic agents, e.g., proteinases, preferably endoproteinases, i.e., protease cleaving internally within a protein, polypeptide or peptide chain. A non-limiting list of suitable endoproteinases includes serine proteinases (EC 3.4.21), threonine proteinases (EC 3.4.25), cysteine proteinases (EC 3.4.22), aspartic acid proteinases (EC 3.4.23), metalloproteinases (EC 3.4.24) and glutamic acid proteinases. Exemplary non-limiting endoproteinases include trypsin, chymotrypsin, elastase, *Lysobacter enzymogenes* endoproteinase Lys-C, *Staphylococcus aureus* endoproteinase Glu-C (endopeptidase V8) or *Clostridium histolyticum* endoproteinase Arg-C (clostripain). Further known or yet to be identified enzymes may be used; a skilled person can choose suitable protease(s) on the basis of their cleavage specificity and frequency to achieve desired peptide forms. Preferably, the proteolysis may be effected by endopeptidases of the trypsin type (EC 3.4.21.4), preferably trypsin, such as, without limitation, preparations of trypsin from bovine pancreas, human pancreas, porcine pancreas, recombinant trypsin, Lys-acetylated trypsin, trypsin in solution, trypsin immobilised to a solid support, etc. Trypsin is particularly useful, inter alia due to high specificity and efficiency of cleavage. The invention also contemplates the use of any trypsin-like protease, i.e., with a similar specificity to that of trypsin. Otherwise, chemical reagents may be used for proteolysis. For example, CNBr can cleave at Met; BNPS-skatole can cleave at Trp. The conditions for treatment, e.g., protein concentration, enzyme or chemical reagent concentration, pH, buffer, temperature, time, can be determined by the skilled person depending on the enzyme or chemical reagent employed.

Also provided is thus an isolated fragment of PERLECAN as defined here above. Such fragments may give useful information about the presence and quantity of PERLECAN in biological samples, whereby the detection of said fragments is of interest. Hence, the herein disclosed fragments of PERLECAN are useful biomarkers. A preferred PERLECAN fragment may comprise, consist essentially of or consist of the sequence as set forth in SEQ ID NO: 2.

The term "isolated" with reference to a particular component (such as for instance, a protein, polypeptide, peptide or fragment thereof) generally denotes that such component exists in separation from—for example, has been separated from or prepared in separation from—one or more other components of its natural environment. For instance, an isolated human or animal protein, polypeptide, peptide or fragment exists in separation from a human or animal body where it occurs naturally.

The term "isolated" as used herein may preferably also encompass the qualifier "purified". As used herein, the term "purified" with reference to protein(s), polypeptide(s), peptide(s) and/or fragment(s) thereof does not require absolute purity. Instead, it denotes that such protein(s), polypeptide(s), peptide(s) and/or fragment(s) is (are) in a discrete environment in which their abundance (conveniently expressed in terms of mass or weight or concentration) relative to other proteins is greater than in a biological sample. A discrete environment denotes a single medium, such as for example a single solution, gel, precipitate, lyophilisate, etc. Purified peptides, polypeptides or fragments may be obtained by known methods including, for example, laboratory or recombinant synthesis, chromatography, preparative electrophoresis, centrifugation, precipitation, affinity purification, etc.

Purified protein(s), polypeptide(s), peptide(s) and/or fragment(s) may preferably constitute by weight ≧10%, more preferably ≧50%, such as ≧60%, yet more preferably ≧70%, such as ≧80%, and still more preferably ≧90%, such as ≧95%, ≧96%, ≧97%, ≧98%, ≧99% or even 100%, of the protein content of the discrete environment. Protein content may be determined, e.g., by the Lowry method (Lowry et al. 1951. J Biol Chem 193: 265), optionally as described by Hartree 1972 (Anal Biochem 48: 422-427). Also, purity of peptides or polypeptides may be determined by SDS-PAGE under reducing or non-reducing conditions using Coomassie blue or, preferably, silver stain.

Further disclosed are isolated PERLECAN or fragments thereof as taught herein comprising a detectable label. This facilitates ready detection of such fragments. The term "label" as used throughout this specification refers to any atom, molecule, moiety or biomolecule that can be used to provide a detectable and preferably quantifiable read-out or property, and that can be attached to or made part of an entity of interest, such as a peptide or polypeptide or a specific-binding agent. Labels may be suitably detectable by mass spectrometric, spectroscopic, optical, colorimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horse-radish phosphatise or alkaline phosphatise as commonly used in immunoassays); binding moieties such as biotin-streptavidin; haptens such as digoxigenin; luminogenic, phosphorescent or fluorogenic moieties; mass tags; and fluorescent dyes alone or in combination with moieties that can suppress or shift emission spectra by fluorescence resonance energy transfer (FRET).

For example, the label may be a mass-altering label. Preferably, a mass-altering label may involve the presence of a distinct stable isotope in one or more amino acids of the peptide vis-à-vis its corresponding non-labelled peptide. Mass-labelled peptides are particularly useful as positive controls, standards and calibrators in mass spectrometry applications. In particular, peptides including one or more distinct isotopes are chemically alike, separate chromatographically and electrophoretically in the same manner and also ionise and fragment in the same way. However, in a suitable mass analyser such peptides and optionally select fragmentation ions thereof will display distinguishable m/z ratios and can thus be discriminated. Examples of pairs of distinguishable stable isotopes include H and D, $^{12}$C and $^{13}$C, $^{14}$N and $^{15}$N or $^{16}$O and $^{18}$O. Usually, peptides and proteins of biological samples analysed in the present invention may substantially only contain common isotopes having high prevalence in nature, such as for example H, $^{12}$C, $^{14}$N and $^{16}$O. In such case, the mass-labelled peptide may be labelled with one or more uncommon isotopes having low prevalence in nature, such as for instance D, $^{13}$C, $^{15}$N and/or $^{18}$O. It is also conceivable that in cases where the peptides or proteins of a biological sample would include one or more uncommon isotopes, the mass-labelled peptide may comprise the respective common isotope(s).

Isotopically-labelled synthetic peptides may be obtained inter alia by synthesising or recombinantly producing such peptides using one or more isotopically-labelled amino acid substrates, or by chemically or enzymatically modifying unlabelled peptides to introduce thereto one or more distinct isotopes. By means of example and not limitation, D-labelled peptides may be synthesised or recombinantly produced in the presence of commercially available deuterated L-methionine $CH_3$—S—$CD_2CD_2$—$CH(NH_2)$—COOH or deuterated arginine $H_2NC(=NH)$—NH—$(CD_2)_3$—$CD(NH_2)$—COOH. It shall be appreciated that any amino acid of which deuterated or $^{15}$N- or $^{13}$C-containing forms exist may be considered for synthesis or recombinant production of labelled peptides. In another non-limiting example, a peptide may be treated with trypsin in $H_2^{16}O$ or $H_2^{18}O$, leading to incorporation of two oxygens ($^{16}O$ or $^{18}O$, respectively) at the COOH-termini of said peptide (e.g., US 2006/105415).

Accordingly, also contemplated is the use of PERLECAN and isolated fragments thereof as taught herein, optionally comprising a detectable label, as (positive) controls, standards or calibrators in qualitative or quantitative detection assays (measurement methods) of PERLECAN, and particularly in such methods for predicting, diagnosing, prognosticating and/or monitoring the diseases or conditions as taught herein in subjects. The proteins, polypeptides or peptides may be supplied in any form, inter alia as precipitate, vacuum-dried, lyophilisate, in solution as liquid or frozen, or covalently or non-covalently immobilised on solid phase, such as for example, on solid chromatographic matrix or on glass or plastic or other suitable surfaces (e.g., as a part of peptide arrays and microarrays). The peptides may be readily prepared, for example, isolated from natural sources, or prepared recombinantly or synthetically.

Further disclosed are binding agents capable of specifically binding to any one or more of the isolated fragments of PERLECAN as taught herein. Also disclosed are binding agents capable of specifically binding to only one of isolated fragments of PERLECAN as taught herein. Binding agents as intended throughout this specification may include inter alia an antibody, aptamer, photoaptamer, protein, peptide, peptidomimetic or a small molecule.

A binding agent may be capable of binding both the plasma circulating form and the cell-bound or retained from of PERLECAN. Preferably, a binding agent may be capable of specifically binding or detecting the plasma circulating form of PERLECAN.

The term "specifically bind" as used throughout this specification means that an agent (denoted herein also as "specific-binding agent") binds to one or more desired molecules or analytes, such as to one or more proteins, polypeptides or peptides of interest or fragments thereof substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to protein(s) polypeptide(s), peptide(s) and/or fragment(s) thereof of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold or more greater, than its affinity for a non-target molecule.

Preferably, the agent may bind to its intended target(s) with affinity constant ($K_A$) of such binding $K_A \geq 1 \times 10^6$ M$^{-1}$, more preferably $K_A \geq 1 \times 10^7$ M$^{-1}$, yet more preferably $K_A \geq 1 \times 10^{8}$ $^{-1}$, even more preferably $K_A \geq 1 \times 10^9$ M$^{-1}$, and still more preferably $K_A \geq 1 \times 10^{10}$ M$^{-1}$ or $K_A 24\ 1 \times 10^{11}$ M$^{-1}$, wherein $K_A = [SBA\_T]/[SBA][T]$, SBA denotes the specific-binding agent, T denotes the intended target. Determination of $K_A$ can be carried out by methods known in the art, such as for example, using equilibrium dialysis and Scatchard plot analysis.

Specific binding agents as used throughout this specification may include inter alia an antibody, aptamer, photoaptamer, protein, peptide, peptidomimetic or a small molecule.

As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments; diabodies; linear antibodies; single-chain antibody molecules; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromaderius*), llama (e.g., *Lama paccos, Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

The term "aptamer" refers to single-stranded or double-stranded oligo-DNA, oligo-RNA or oligo-DNA/RNA or any analogue thereof, that can specifically bind to a target molecule such as a peptide. Advantageously, aptamers can display fairly high specificity and affinity (e.g., $K_A$ in the order $1 \times 10^9$ $M^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Norwell 1995 (Trends Biotechnol 13: 132-134).

The term "small molecule" refers to compounds, preferably organic compounds, with a size comparable to those organic molecules generally used in pharmaceuticals. The term excludes biological macromolecules (e.g., proteins, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

Hence, also disclosed are methods for immunising animals, e.g., non-human animals such as laboratory or farm, animals using (i.e., using as the immunising antigen) the herein taught fragments of PERLECAN, optionally attached to a presenting carrier. Immunisation and preparation of antibody reagents from immune sera is well-known per se and described in documents referred to elsewhere in this specification. The animals to be immunised may include any animal species, preferably warm-blooded species, more preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel, llama or horse. The term "presenting carrier" or "carrier" generally denotes an immunogenic molecule which, when bound to a second molecule, augments immune responses to the latter, usually through the provision of additional T cell epitopes. The presenting carrier may be a (poly)peptidic structure or a non-peptidic structure, such as inter alia glycans, polyethylene glycols, peptide mimetics, synthetic polymers, etc. Exemplary non-limiting carriers include human Hepatitis B virus core protein, multiple C3d domains, tetanus toxin fragment C or yeast Ty particles.

Immune sera obtained or obtainable by immunisation as taught herein may be particularly useful for generating antibody reagents that specifically bind to one or more of the herein disclosed fragments of PERLECAN.

Further disclosed are methods for selecting specific-binding agents which bind (a) one or more of the PERLECAN fragments taught herein, substantially to the exclusion of (b) PERLECAN and/or other fragments thereof. Conveniently, such methods may be based on subtracting or removing binding agents which cross-react or cross-bind the non-desired PERLECAN molecules under (b). Such subtraction may be readily performed as known in the art by a variety of affinity separation methods, such as affinity chromatography, affinity solid phase extraction, affinity magnetic extraction, etc.

Any existing, available or conventional separation, detection and quantification methods can be used herein to measure the presence or absence (e.g., readout being present vs. absent; or detectable amount vs. undetectable amount) and/or quantity (e.g., readout being an absolute or relative quantity, such as, for example, absolute or relative concentration) of PERLECAN and/or fragments thereof and optionally of the one or more other biomarkers or fragments thereof in samples (any molecules or analytes of interest to be so-measured in samples, including PERLECAN and fragments thereof, may be herein below referred to collectively as biomarkers).

For example, such methods may include immunoassay methods, mass spectrometry analysis methods, or chromatography methods, or combinations thereof.

The term "immunoassay" generally refers to methods known as such for detecting one or more molecules or analytes of interest in a sample, wherein specificity of an immunoassay for the molecule(s) or analyte(s) of interest is conferred by specific binding between a specific-binding agent, commonly an antibody, and the molecule(s) or analyte(s) of interest. Immunoassay technologies include without limitation direct ELISA (enzyme-linked immunosorbent assay), indirect ELISA, sandwich ELISA, competitive ELISA, multiplex ELISA, radioimmunoassay (RIA), ELISPOT technologies, and other similar techniques known in the art. Principles of these immunoassay methods are known in the art, for example John R. Crowther, "The ELISA Guidebook", 1st ed., Humana Press 2000, ISBN 0896037282.

By means of further explanation and not limitation, direct ELISA employs a labelled primary antibody to bind to and thereby quantify target antigen in a sample immobilised on a solid support such as a microwell plate. Indirect ELISA uses a non-labelled primary antibody which binds to the target antigen and a secondary labelled antibody that recognises and allows to quantify the antigen-bound primary antibody. In sandwich ELISA the target antigen is captured from a sample using an immobilised 'capture' antibody which binds to one antigenic site within the antigen, and subsequent to removal of non-bound analytes the so-captured antigen is detected using a 'detection' antibody which binds to another antigenic site within said antigen, where the detection antibody may be directly labelled or indirectly detectable as above. Competitive ELISA uses a labelled 'competitor' that may either be the primary antibody or the target antigen. In an example, non-labelled immobilised primary antibody is incubated with a sample, this reaction is allowed to reach equilibrium, and then labelled target antigen is added. The latter will bind to the primary antibody wherever its binding sites are not yet occupied by non-labelled target antigen from the sample. Thus, the detected amount of bound labelled antigen inversely correlates with the amount of non-labelled antigen in the sample. Multiplex ELISA allows simultaneous detection of two or more analytes within a single compartment (e.g., microplate well) usually at a plurality of array addresses (see, for example, Nielsen & Geierstanger 2004. J Immunol Methods 290: 107-20 and Ling et al. 2007. Expert Rev Mol Diagn 7: 87-98 for further guidance). As appreciated, labelling in ELISA technologies is usually by enzyme (such as, e.g., horse-radish peroxidase) conjugation and the end-point is typically colorimetric, chemiluminescent or fluorescent, magnetic, piezo electric, pyroelectric and other.

Radioimmunoassay (RIA) is a competition-based technique and involves mixing known quantities of radioactively-labelled (e.g., $^{125}$I- or $^{131}$I-labelled) target antigen with antibody to said antigen, then adding non-labelled or 'cold' antigen from a sample and measuring the amount of labelled antigen displaced (see, e.g., "An Introduction to Radioimmunoassay and Related Techniques", by Chard T, ed., Elsevier Science 1995, ISBN 0444821198 for guidance).

Generally, any mass spectrometric (MS) techniques that can obtain precise information on the mass of peptides, and preferably also on fragmentation and/or (partial) amino acid sequence of selected peptides (e.g., in tandem mass spectrometry, MS/MS; or in post source decay, TOF MS), are useful herein. Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/ TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$^n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)$^n$; atmospheric pressure photoionization mass spectrometry (APPI-MS); APPI-MS/MS; and APPI-(MS)$^n$. Peptide ion fragmentation in tandem MS (MS/MS) arrangements may be achieved using manners established in the art, such as, e.g., collision induced dissociation (CID). Detection and quantification of biomarkers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods described herein below.

Chromatography can also be used for measuring biomarkers. As used herein, the term "chromatography" encompasses methods for separating chemical substances, referred to as such and vastly available in the art. In a preferred approach, chromatography refers to a process in which a mixture of chemical substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography is also widely applicable for the separation of chemical compounds of biological origin, such as, e.g., amino acids, proteins, fragments of proteins or peptides, etc.

Chromatography as used herein may be preferably columnar (i.e., wherein the stationary phase is deposited or packed in a column), preferably liquid chromatography, and yet more preferably HPLC. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immuno-affinity, immobilised metal affinity chromatography, and the like.

Chromatography, including single-, two- or more-dimensional chromatography, may be used as a peptide fractionation method in conjunction with a further peptide analysis method, such as for example, with a downstream mass spectrometry analysis as described elsewhere in this specification.

Further peptide or polypeptide separation, identification or quantification methods may be used, optionally in conjunction with any of the above described analysis methods, for measuring biomarkers in the present disclosure. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

The various aspects and embodiments taught herein may further rely on comparing the quantity of PERLECAN, as defined herein, measured in samples with reference values of the quantity of PERLECAN, wherein said reference values represent known predictions, diagnoses and/or prognoses of diseases or conditions as taught herein.

For example, distinct reference values may represent the prediction of a risk (e.g., an abnormally elevated risk) of having a given disease or condition as taught herein vs. the prediction of no or normal risk of having said disease or condition. In another example, distinct reference values may represent predictions of differing degrees of risk of having such disease or condition.

In a further example, distinct reference values can represent the diagnosis of a given disease or condition as taught herein vs. the diagnosis of no such disease or condition (such as, e.g., the diagnosis of healthy, or recovered from said disease or condition, etc.). In another example, distinct reference values may represent the diagnosis of such disease or condition of varying severity.

In yet another example, distinct reference values may represent a good prognosis for a given disease or condition as taught herein vs. a poor prognosis for said disease or condition. In a further example, distinct reference values may represent varyingly favourable or unfavourable prognoses for such disease or condition.

Such comparison may generally include any means to determine the presence or absence of at least one difference and optionally of the size of such different between values or profiles being compared. A comparison may include a visual inspection, an arithmetical or statistical comparison of measurements. Such statistical comparisons include, but are not limited to, applying a rule. If the values or biomarker profiles comprise at least one standard, the comparison to determine a difference in said values or biomarker profiles may also include measurements of these standards, such that measurements of the biomarker are correlated to measurements of the internal standards.

Reference values for the quantity of PERLECAN may be established according to known procedures previously employed for other biomarkers.

For example, a reference value of the quantity of PERLECAN for a particular prediction, diagnosis and/or prognosis of given disease or condition as taught herein may be established by determining the quantity of PERLECAN in sample(s) from one individual or from a population of individuals characterised by said particular prediction, diagnosis and/or prognosis of said disease or condition (i.e., for whom said prediction, diagnosis and/or prognosis of renal dysfunction holds true). Such population may comprise without limitation $\geq 2$, $\geq 10$, $\geq 100$, or even several hundreds or more individuals.

Hence, by means of an illustrative example, reference values of the quantity of PERLECAN for the diagnoses of a given disease or condition as taught herein vs. no such disease or condition may be established by determining the quantity of PERLECAN in sample(s) from one individual or from a population of individuals diagnosed (e.g., based on other adequately conclusive means, such as, for example, clinical signs and symptoms, imaging, ECG, etc.) as, respectively, having or not having said disease or condition.

In an embodiment, reference value(s) as intended herein may convey absolute quantities of PERLECAN. In another embodiment, the quantity of PERLECAN in a sample from a tested subject may be determined directly relative to the reference value (e.g., in terms of increase or decrease, or fold-increase or fold-decrease). Advantageously, this may allow to compare the quantity of PERLECAN in the sample from the subject with the reference value (in other words to measure the relative quantity of PERLECAN in the sample from the subject vis-à-vis the reference value) without the need to first determine the respective absolute quantities of PERLECAN.

The expression level or presence of a biomarker in a sample of a patient may sometimes fluctuate, i.e. increase or decrease significantly without change (appearance of, worsening or improving of) symptoms. In such an event, the marker change precedes the change in symptoms and becomes a more sensitive measure than symptom change. Therapeutic intervention can be initiated earlier and be more effective than waiting for deteriorating symptoms. Early intervention at a more benign status may be carried out safely at home, which is a major improvement from treating seriously deteriorated patients in the emergency room.

Measuring the PERLECAN level of the same patient at different time points can in such a case thus enable the continuous monitoring of the status of the patient and can lead to prediction of worsening or improvement of the patient's condition with regard to a given disease or condition as taught herein. A home or clinical test kit or device as indicated herein can be used for this continuous monitoring. One or more reference values or ranges of PERLECAN levels linked to a certain disease state (e.g. renal dysfunction or no renal dysfunction) for such a test can e.g. be determined beforehand or during the monitoring process over a certain period of time in said subject. Alternatively, these reference values or ranges can be established through data sets of several patients with highly similar disease phenotypes, e.g. from healthy subjects or subjects not having the disease or condition of interest. A sudden deviation of the PERLECAN levels from said reference value or range can predict the worsening of the condition of the patient (e.g. at home or in the clinic) before the (often severe) symptoms actually can be felt or observed.

Also disclosed is thus a method or algorithm for determining a significant change in the level of the PERLECAN marker in a certain patient, which is indicative for change (worsening or improving) in clinical status. In addition, the invention allows establishing the diagnosis that the subject is recovering or has recovered from a given disease or condition as taught herein.

In an embodiment the present methods may include a step of establishing such reference value(s). In an embodiment, the present kits and devices may include means for establishing a reference value of the quantity of PERLECAN for a particular prediction, diagnosis and/or prognosis of a given disease or condition as taught herein. Such means may for example comprise one or more samples (e.g., separate or pooled samples) from one or more individuals characterised by said particular prediction, diagnosis and/or prognosis of said disease or condition.

The various aspects and embodiments taught herein may further entail finding a deviation or no deviation between the quantity of PERLECAN measured in a sample from a subject and a given reference value.

A "deviation" of a first value from a second value may generally encompass any direction (e.g., increase: first value >second value; or decrease: first value <second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., $\pm 1 \times SD$ or $\pm 2 \times SD$, or $\pm 1 \times SE$ or $\pm 2 \times SE$). Deviation may also refer to a value falling outside of a reference range defined by values in a given population (for example, outside of a range which comprises $\geq 40\%$, $\geq 50\%$, $\geq 60\%$, $\geq 70\%$, $\geq 75\%$ or $\geq 80\%$ or $\geq 85\%$ or $\geq 90\%$ or $\geq 95\%$ or even $\geq 100\%$ of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction, diagnosis and/or prognosis methods, e.g., sensitivity and/or specificity of at least 50%, or at least 60%, or at least 70%, or at least 80%, or at least 85%, or at least 90%, or at least 95%.

For example, in an embodiment, an elevated quantity of PERLECAN in the sample from the subject—preferably at least about 1.1-fold elevated, or at least about 1.2-fold elevated, more preferably at least about 1.3-fold elevated, even more preferably at least about 1.4-fold elevated, yet more preferably at least about 1.5-fold elevated, such as between about 1.1-fold and 3-fold elevated or between about 1.5-fold and 2-fold elevated—compared to a reference value representing the prediction or diagnosis of no given disease or condition as taught herein or representing a good prognosis for said disease or condition indicates that the subject has or is at risk of having said disease or condition or indicates a poor prognosis for the disease or condition in the subject.

When a deviation is found between the quantity of PERLECAN in a sample from a subject and a reference value representing a certain prediction, diagnosis and/or prognosis of a given disease or condition as taught herein, said deviation is indicative of or may be attributed to the conclusion that the prediction, diagnosis and/or prognosis of said disease or condition in said subject is different from that represented by the reference value.

When no deviation is found between the quantity of PERLECAN in a sample from a subject and a reference value representing a certain prediction, diagnosis and/or prognosis of a given disease or condition as taught herein, the absence of such deviation is indicative of or may be attributed to the conclusion that the prediction, diagnosis and/or prognosis of said disease or condition in said subject is substantially the same as that represented by the reference value.

The above considerations apply analogously to biomarker profiles.

When two or more different biomarkers are determined in a subject, their respective presence, absence and/or quantity may be together represented as a biomarker profile, the values for each measured biomarker making a part of said profile. As used herein, the term "profile" includes any set of data that represents the distinctive features or characteristics associated with a condition of interest, such as with a particular prediction, diagnosis and/or prognosis of a given disease or condition as taught herein. The term generally encompasses inter alia nucleic acid profiles, such as for example genotypic profiles (sets of genotypic data that represents the genotype of one or more genes associated with a condition of interest), gene copy number profiles (sets of gene copy number data that represents the amplification or deletion of one or more genes associated with a condition of interest), gene expression profiles (sets of gene expression data that represents the mRNA levels of one or more genes associated with a condition of interest), DNA methylation profiles (sets of methylation data that represents the DNA methylation levels of one or more genes associated with a condition of interest), as well as protein, polypeptide or peptide profiles, such as for example protein expression profiles (sets of protein expression data that represents the levels of one or more proteins associated with a condition of interest), protein activation profiles (sets of data that represents the activation or inactivation of one or more proteins associated with a condition of interest), protein modification profiles (sets of data that represents the modification of one or more proteins associated with a condition of interest), protein cleavage profiles (sets of data that represent the proteolytic cleavage of one or more proteins associated with a condition of interest), as well as any combinations thereof.

Biomarker profiles may be created in a number of ways and may be the combination of measurable biomarkers or aspects of biomarkers using methods such as ratios, or other more complex association methods or algorithms (e.g., rule-based methods). A biomarker profile comprises at least two measurements, where the measurements can correspond to the same or different biomarkers. A biomarker profile may also comprise at least three, four, five, 10, 20, 30 or more measurements. In one embodiment, a biomarker profile comprises hundreds, or even thousands, of measurements.

Hence, for example, distinct reference profiles may represent the prediction of a risk (e.g., an abnormally elevated risk) of having a given disease or condition vs. the prediction of no or normal risk of having said disease or condition. In another example, distinct reference profiles may represent predictions of differing degrees of risk of having said disease or condition.

In a further example, distinct reference profiles can represent the diagnosis of a given disease or condition as taught herein vs. the diagnosis no such disease or condition (such as, e.g., the diagnosis of healthy, recovered from said disease or condition, etc.). In another example, distinct reference profiles may represent the diagnosis of said disease or condition of varying severity.

In a yet another example, distinct reference profiles may represent a good prognosis for a disease or condition as taught herein vs. a poor prognosis for said disease or condition. In a further example, distinct reference profiles may represent varyingly favourable or unfavourable prognoses for such disease or condition.

Reference profiles used herein may be established according to known procedures previously employed for other biomarkers.

For example, a reference profile of the quantity of PERLECAN and the presence or absence and/or quantity of one or more other biomarkers for a particular prediction, diagnosis and/or prognosis of a given disease or condition as taught herein may be established by determining the profile in sample(s) from one individual or from a population of individuals characterised by said particular prediction, diagnosis and/or prognosis of said disease or condition (i.e., for whom said prediction, diagnosis and/or prognosis of said disease or condition holds true). Such population may comprise without limitation $\geq 2$, $\geq 10$, $\geq 100$, or even several hundreds or more individuals.

Hence, by means of an illustrative example, reference profiles for the diagnoses of a given disease or condition as taught herein vs. no such disease or condition may be established by determining the biomarker profiles in sample(s) from one individual or from a population of individuals diagnosed as, respectively, having or not having said disease or condition.

In an embodiment the present methods may include a step of establishing such reference profile(s). In an embodiment, the present kits and devices may include means for establishing a reference profile for a particular prediction, diagnosis and/or prognosis of a given disease or condition as taught herein. Such means may for example comprise one or more samples (e.g., separate or pooled samples) from one or more individuals characterised by said particular prediction, diagnosis and/or prognosis of said disease or condition.

Further, art-known multi-parameter analyses may be employed *mutatis mutandis* to determine deviations between groups of values and profiles generated there from (e.g., between sample and reference biomarker profiles).

When a deviation is found between the sample profile and a reference profile representing a certain prediction, diagnosis and/or prognosis of a given disease or condition as taught herein, said deviation is indicative of or may be attributed to the conclusion that the prediction, diagnosis and/or prognosis of said disease or condition in said subject is different from that represented by the reference profile.

When no deviation is found between the sample profile and a reference profile representing a certain prediction, diagnosis and/or prognosis of a given disease or condition as taught herein, the absence of such deviation is indicative of or may be attributed to the conclusion that the prediction, diagnosis and/or prognosis of said disease or condition in said subject is substantially the same as that represented by the reference profile.

The present invention further provides kits or devices for the diagnosis, prediction, prognosis and/or monitoring of any one disease or condition as taught herein comprising means for detecting the level of any one or more biomarkers in a sample of the patient. In a more preferred embodiment, such a kit or kits of the invention can be used in clinical settings or at home. The kit according to the invention can be used for diagnosing said disease or condition, for monitoring the effectiveness of treatment of a subject suffering from said disease or condition with an agent, or for preventive screening of subjects for the occurrence of said disease or condition in said subject.

In a clinical setting, the kit or device can be in the form of a bed-side device or in an emergency team setting, e.g. as part of the equipment of an ambulance or other moving emergency vehicle or team equipment or as part of a first-aid kit. The diagnostic kit or device can assist a medical practitioner, a first aid helper, or nurse to decide whether the patient under observation is developing a disease or condition as taught herein, after which appropriate action or treatment can be performed.

A home-test kit gives the patient a readout which he can communicate to a medicinal practitioner, a first aid helper or to the emergency department of a hospital, after which appropriate action can be taken. Such a home-test device is of particular interest for people having either a history of, or are at risk of suffering from any one disease or condition as taught herein.

Typical kits or devices according to the invention comprise the following elements:
a) a means for obtaining a sample from the subject
b) a means or device for measuring the amount of any one or more markers as taught herein in said sample and visualizing whether the amount of the one or more markers in said sample is below or above a certain threshold level or value, indicating whether the subject is suffering from a given disease or condition as taught herein or not.

In any of the embodiments of the invention, the kits or devices can additionally comprise c) means for communicating directly with a medical practitioner, an emergency department of the hospital or a first aid post, indicating that a person is suffering from said disease or condition or not.

The term "threshold level or value" or "reference value" is used interchangeably as a synonym and is as defined herein. It can also be a range of base-line (e.g. "dry weight") values determined in an individual patient or in a group of patients with highly similar disease conditions, taken at about the same time of gestation.

Without wanting to be bound by any theory, the inventors saw that the PERLECAN level is increased in case of renal dysfunction, both at the protein and mRNA level. In the PE patients tested, the PERLECAN level is higher than that of healthy subjects.

The threshold value indicated in the present invention is therefore more to be seen as a value in a reference, i.e. non-PE pregnant subject, taken at about the same stage of gestation and not so much as the value of the PE-subject before or after pregnancy.

Any of kits as defined herein can be used as a bed-side device for use by the subject himself or by a clinical practitioner.

Non-limiting examples are: systems comprising specific binding molecules for said one or more markers attached to a solid phase, e.g. lateral flow strips or dipstick devices and the like well known in the art. One non-limiting example to perform a biochemical assay is to use a test-strip and labelled antibodies which combination does not require any washing of the membrane. The test strip is well known, for example, in the field of pregnancy testing kits where an anti-hCG antibody is present on the support, and is carried complexed with hCG by the flow of urine onto an immobilised second antibody that permits visualisation. Other non-limiting examples of such home test devices, systems or kits can be found for example in the following U.S. Pat. Nos. 6,107,045, 6,974,706, 5,108,889, 6,027,944, 6,482,156, 6,511,814, 5,824,268, 5,726,010, 6,001,658 or U.S. patent applications: 2008/0090305 or 2003/0109067. In a preferred embodiment, the invention provides a lateral flow device or dipstick. Such dipstick comprises a test strip allowing migration of a sample by capillary flow from one end of the strip where the sample is applied to the other end of such strip where presence of an analyte in said sample is measured. In another embodiment, the invention provides a device comprising a reagent strip. Such reagent strip comprises one or more test pads which when wetted with the sample, provide a colour change in the presence of an analyte and/or indicate the concentration of the protein in said sample.

In order to obtain a semi-quantitative test strip in which only a signal is formed once the level of any one or more markers in the sample is higher than a certain predetermined threshold level or value, a predetermined amount of fixed capture antibodies for PERLECAN can be present on the test strip. This enables the capture of a certain amount of PERLECAN present in the sample, corresponding to the threshold level or value as predetermined. The remaining amount of PERLECAN (if any) bound by e.g. a conjugated or labelled binding molecules can then be allowed to migrate to a detection zone which subsequently only produces a signal if the level of said one or more biomarkers in the sample is higher than the predetermined threshold level or value.

Another possibility to determine whether the amount of any one or more markers in the sample is below or above a certain threshold level or value, is to use a primary capturing antibody capturing all said one or more markers protein present in the sample, in combination with a labelled secondary antibody, developing a certain signal or colour when bound to the solid phase. The intensity of the colour or signal can then either be compared to a reference colour or signal chart indicating that when the intensity of the signal is above a certain threshold signal, the test is positive. Alternatively, the amount or intensity of the colour or signal can be measured with an electronic device comprising e.g. a light absorbance sensor or light emission meter, resulting in a numerical value of signal intensity or colour absorbance formed, which can then be displayed to the subject in the form of a negative result if said numerical value is below the threshold value or a positive result if said numerical value is above the threshold value. This embodiment is of particular relevance in monitoring the level of said one or more markers in a patient over a period of time.

The reference value or range can e.g. be determined using the home device in a period wherein the subject is free of a given disease or condition, giving the patient an indication of his base-line level of any one or more markers. Regularly using the home test device will thus enable the subject to notice a sudden change in levels of said one or more markers as compared to the base-line level, which can enable him to contact a medical practitioner.

Alternatively, the reference value can be determined in the subject suffering from a given disease or condition as taught herein, which then indicates his personal "risk level" for any one or more markers, i.e. the level of said one or more markers which indicates he is or will soon be exposed to said disease or condition. This risk level is interesting for monitoring the disease progression or for evaluating the effect of the treatment.

Furthermore, the reference value or level can be established through combined measurement results in subjects with highly similar disease states or phenotypes (e.g. all having no disease or condition as taught herein or having said disease or condition).

Non-limiting examples of semi-quantitative tests known in the art, the principle of which could be used for the home test device according to the present invention are the HIV/AIDS test or Prostate Cancer tests sold by Sanitoets. The home prostate test is a rapid test intended as an initial semi-quantitative test to detect PSA blood levels higher than 4 ng/ml in whole blood. The typical home self-test kit comprises the following components: a test device to which the blood sample is to be administered and which results in a signal when the protein level is above a certain threshold level, an amount of diluent e.g. in dropper pipette to help the transfer of the analytes (i.e. the protein of interest) from the sample application zone to the signal detection zone, optionally an empty pipette for blood specimen collection, a finger pricking device, optionally a sterile swab to clean the area of pricking and instructions of use of the kit.

Similar tests are also known for e.g. breast cancer detection and CRP-protein level detection in view of cardiac risk home tests. The latter test encompasses the sending of the test result to a laboratory, where the result is interpreted by a technical or medical expert. Such telephone or Internet based diagnosis of the patient's condition is of course possible and advisable with most of the kits, since interpretation of the test result is often more important than conducting the test. When using an electronic device as mentioned above which gives a numerical value of the level of protein present in the sample, this value can of course easily be communicated through telephone, mobile telephone, satellite phone, E-mail, internet or other communication means, warning a hospital, a medicinal practitioner or a first aid team that a person is, or may be at risk of, suffering from the disease or condition as taught herein. A non-limiting example of such a system is disclosed in U.S. Pat. No. 6,482,156.

The presence and/or concentration of PERLECAN in a sample can be measured by surface plasmon resonance (SPR) using a chip having PERLECAN binding molecule immobilized thereon, fluorescence resonance energy transfer (FRET), bioluminescence resonance energy transfer (BRET), fluorescence quenching, fluorescence polarization measurement or other means known in the art. Any of the binding assays described can be used to determine the presence and/or concentration of PERLECAN in a sample. To do so, PERLECAN binding molecule is reacted with a sample, and the concentration of PERLECAN is measured as appropriate for the binding assay being used. To validate and calibrate an assay, control reactions using different concentrations of standard PERLECAN and/or PERLECAN binding molecule can be performed. Where solid phase assays are employed, after incubation, a washing step is performed to remove unbound PERLECAN. Bound, PERLECAN is measured as appropriate for the given label (e.g., scintillation counting, fluorescence, antibody-dye etc.). If a qualitative result is desired, controls and different concentrations may not be necessary. Of course, the roles of PERLECAN and PERLECAN binding molecule may be switched; the skilled person may adapt the method so PERLECAN binding molecule is applied to sample, at various concentrations of sample.

A PERLECAN binding molecule according to the invention is any substance that binds specifically to PERLECAN. Examples of a PERLECAN binding molecule useful according to the present invention, includes, but is not limited to an antibody, a polypeptide, a peptide, a lipid, a carbohydrate, a nucleic acid, peptide-nucleic acid, small molecule, small organic molecule, or other drug candidate. A PERLECAN binding molecule can be natural or synthetic compound, including, for example, synthetic small molecule, compound contained in extracts of animal, plant, bacterial or fungal cells, as well as conditioned medium from such cells. Alternatively, PERLECAN binding molecule can be an engineered protein having binding sites for PERLECAN. According to an aspect of the invention, a PERLECAN binding molecule binds specifically to PERLECAN with an affinity better than $10^{-6}$ M. A suitable PERLECAN binding molecule e can be determined from its binding with a standard sample of PERLECAN. Methods for determining the binding between PERLECAN binding molecule and PERLECAN are known in the art. As used herein, the term antibody includes, but is not limited to, polyclonal antibodies, monoclonal antibodies, humanised or chimeric antibodies, engineered antibodies, and biologically functional antibody fragments (e.g. scFv, nanobodies, Fv, etc) sufficient for binding of the antibody fragment to the protein. Such antibody may be commercially available antibody against PERLECAN, such as, for example, a mouse, rat, human or humanised monoclonal antibody.

In a preferred embodiment, the binding molecule or agent is capable of binding both the mature membrane- or cell-bound PERLECAN protein or fragment. In a more preferred embodiment, the binding agent or molecule is specifically binding or detecting the soluble form, preferably the plasma circulating form of PERLECAN, as defined herein.

According to one aspect of the invention, the PERLECAN binding molecule is labelled with a tag that permits detection with another agent (e.g. with a probe binding partner). Such tags can be, for example, biotin, streptavidin, his-tag, myc tag, maltose, maltose binding protein or any other kind of tag known in the art that has a binding partner. Example of associations which can be utilised in the probe:binding partner arrangement may be any, and includes, for example biotin: streptavidin, his-tag:metal ion (e.g. $Ni^{2+}$), maltose:maltose binding protein.

The specific-binding agents, peptides, polypeptides, proteins, biomarkers etc. in the present kits may be in various forms, e.g., lyophilised, free in solution or immobilised on a solid phase.

They may be, e.g., provided in a multi-well plate or as an array or microarray, or they may be packaged separately and/or individually. The may be suitably labelled as taught herein. Said kits may be particularly suitable for performing the assay methods of the invention, such as, e.g., immunoassays, ELISA assays, mass spectrometry assays, and the like.

The term "modulate" generally denotes a qualitative or quantitative alteration, change or variation specifically encompassing both increase (e.g., activation) or decrease (e.g., inhibition), of that which is being modulated. The term encompasses any extent of such modulation.

For example, where modulation effects a determinable or measurable variable, then modulation may encompass an increase in the value of said variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of said variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation.

Preferably, modulation of the activity and/or level of intended target(s) (e.g., PERLECAN gene or protein) may be specific or selective, i.e., the activity and/or level of intended target(s) may be modulated without substantially altering the activity and/or level of random, unrelated (unintended, undesired) targets.

Reference to the "activity" of a target such as PERLECAN protein may generally encompass any one or more aspects of the biological activity of the target, such as without limitation any one or more aspects of its biochemical activity, enzymatic activity, signalling activity and/or structural activity, e.g., within a cell, tissue, organ or an organism.

In the context of therapeutic or prophylactic targeting of a target, the reference to the "level" of a target such PERLECAN gene or protein may preferably encompass the quantity and/or the availability (e.g., availability for performing its biological activity) of the target, e.g., within a cell, tissue, organ or an organism.

For example, the level of a target may be modulated by modulating the target's expression and/or modulating the expressed target. Modulation of the target's expression may be achieved or observed, e.g., at the level of heterogeneous nuclear RNA (hnRNA), precursor mRNA (pre-mRNA), mRNA or cDNA encoding the target. By means of example and not limitation, decreasing the expression of a target may be achieved by methods known in the art, such as, e.g., by transfecting (e.g., by electroporation, lipofection, etc.) or transducing (e.g., using a viral vector) a cell, tissue, organ or organism with an antisense agent, such as, e.g., antisense DNA or RNA oligonucleotide, a construct encoding the antisense agent, or an RNA interference agent, such as siRNA or shRNA, or a ribozyme or vectors encoding such, etc. By means of example and not limitation, increasing the expression of a target may be achieved by methods known in the art, such as, e.g., by transfecting (e.g., by electroporation, lipofection, etc.) or transducing (e.g., using a viral vector) a cell, tissue, organ or organism with a recombinant nucleic acid which encodes said target under the control of regulatory sequences effecting suitable expression level in said cell, tissue, organ or organism. By means of example and not limitation, the level of the target may be modulated via alteration of the formation of the target (such as, e.g., folding, or interactions leading to formation of a complex), and/or the stability (e.g., the propensity of complex constituents to associate to a complex or disassociate from a complex), degradation or cellular localisation, etc. of the target.

In a preferred embodiment, said modulation leads to a decrease in PERLECAN activity, either by inactivating or blocking its function it at the protein level or by preventing transcription and translation of the coding sequence of PERLECAN into its protein, i.e. at the mRNA or gene level. Since it is clear that the PERLECAN level is increased in subjects suffering form renal dysfunction as defined herein, decreasing the activity of PERLECAN intends to normalise and/o improve the condition of the subject.

The term "antisense" generally refers to a molecule designed to interfere with gene expression and capable of specifically binding to an intended target nucleic acid sequence. Antisense agents typically encompass an oligonucleotide or oligonucleotide analogue capable of specifically hybridising to the target sequence, and may typically comprise, consist essentially of or consist of a nucleic acid sequence that is complementary or substantially complementary to a sequence within genomic DNA, hnRNA, mRNA or cDNA, preferably mRNA or cDNA corresponding to the target nucleic acid. Antisense agents suitable herein may typically be capable of hybridising to their respective target at high stringency conditions, and may hybridise specifically to the target under physiological conditions.

The term "ribozyme" generally refers to a nucleic acid molecule, preferably an oligonucleotide or oligonucleotide analogue, capable of catalytically cleaving a polynucleotide. Preferably, a "ribozyme" may be capable of cleaving mRNA of a given target protein, thereby reducing translation thereof. Exemplary ribozymes contemplated herein include, without limitation, hammer head type ribozymes, ribozymes of the hairpin type, delta type ribozymes, etc. For teaching on ribozymes and design thereof, see, e.g., U.S. Pat. Nos. 5,354, 855, 5,591,610, Pierce et al. 1998 (Nucleic Acids Res 26:

5093-5101), Lieber et al. 1995 (Mol Cell Biol 15: 540-551), and Benseler et al. 1993 (J Am Chem Soc 115: 8483-8484).

"RNA interference" or "RNAi" technology is routine in the art, and suitable RNAi agents intended herein may include inter alia short interfering nucleic acids (siNA), short interfering RNA (siRNA), double-stranded RNA (dsRNA), micro-RNA (miRNA), and short hairpin RNA (shRNA) molecules as known in the art. For teaching on RNAi molecules and design thereof, see inter alia Elbashir et al. 2001 (Nature 411: 494-501), Reynolds et al. 2004 (Nat Biotechnol 22: 326-30), http://rnaidesigner.invitrogen.com/rnaiexpress, Wang & Mu 2004 (Bioinformatics 20: 1818-20), Yuan et al. 2004 (Nucleic Acids Res 32(Web Server issue): W130-4), by M Sohail 2004 ("Gene Silencing by RNA Interference: Technology and Application", $1^{st}$ ed., CRC, ISBN 0849321417), U Schepers 2005 ("RNA Interference in Practice: Principles, Basics, and Methods for Gene Silencing in *C. elegans, Drosophila*, and Mammals", $1^{st}$ ed., Wiley-VCH, ISBN 3527310207), and D R Engelke & J J Rossi 2005 ("Methods in Enzymology, Volume 392: RNA Interference", $1^{st}$ ed., Academic Press, ISBN 0121827976).

The term "pharmaceutically acceptable" as used herein is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, antioxidants, tonicity controlling agents, absorption delaying agents, and the like. The use of such media and agents for pharmaceutical active substances is well known in the art. Except insofar as any conventional media or agent is incompatible with the active substance, its use in the therapeutic compositions may be contemplated.

The present active substances (agents) may be used alone or in combination with any therapies known in the art for the disease and conditions as taught herein ("combination therapy"). Combination therapies as contemplated herein may comprise the administration of at least one active substance of the present invention and at least one other pharmaceutically or biologically active ingredient. Said present active substance(s) and said pharmaceutically or biologically active ingredient(s) may be administered in either the same or different pharmaceutical formulation(s), simultaneously or sequentially in any order.

The dosage or amount of the present active substances (agents) used, optionally in combination with one or more other active compound to be administered, depends on the individual case and is, as is customary, to be adapted to the individual circumstances to achieve an optimum effect. Thus, it depends on the nature and the severity of the disorder to be treated, and also on the sex, age, body weight, general health, diet, mode and time of administration, and individual responsiveness of the human or animal to be treated, on the route of administration, efficacy, metabolic stability and duration of action of the compounds used, on whether the therapy is acute or chronic or prophylactic, or on whether other active compounds are administered in addition to the agent(s) of the invention.

Without limitation, depending on the type and severity of the disease, a typical daily dosage might range from about 1 µg/kg to 100 mg/kg of body weight or more, depending on the factors mentioned above. For repeated administrations over several days or longer, depending on the condition, the treatment is sustained until a desired suppression of disease symptoms occurs. A preferred dosage of the active substance of the invention may be in the range from about 0.05 mg/kg to about 10 mg/kg of body weight. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every two or three weeks.

As used herein, a phrase such as "a subject in need of treatment" includes subjects that would benefit from treatment of a given disease or condition as taught herein. Such subjects may include, without limitation, those that have been diagnosed with said condition, those prone to contract or develop said condition and/or those in whom said condition is to be prevented.

The terms "treat" or "treatment" encompass both the therapeutic treatment of an already developed disease or condition, as well as prophylactic or preventative measures, wherein the aim is to prevent or lessen the chances of incidence of an undesired affliction, such as to prevent the chances of contraction and progression of a disease or condition as taught herein. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

The term "prophylactically effective amount" refers to an amount of an active compound or pharmaceutical agent that inhibits or delays in a subject the onset of a disorder as being sought by a researcher, veterinarian, medical doctor or other clinician. The term "therapeutically effective amount" as used herein, refers to an amount of active compound or pharmaceutical agent that elicits the biological or medicinal response in a subject that is being sought by a researcher, veterinarian, medical doctor or other clinician, which may include inter alia alleviation of the symptoms of the disease or condition being treated. Methods are known in the art for determining therapeutically and prophylactically effective doses for the present compounds.

The above aspects and embodiments are further supported by the following non-limiting examples.

EXAMPLES

Example 1

MASSterclass Targeted Protein Quantitation for Early Validation of Candidate Markers Derived from Discovery MASSTERCLASS Experimental Setup MASSterclass assays use targeted tandem mass spectrometry with stable isotope dilution as an end-stage peptide quantitation system (also called Multiple Reaction Monitoring (MRM) and Single Reaction Monitoring (SRM). The targeted peptide is specific (i.e., proteotypic) for the specific protein of interest. i.e., the amount of peptide measured is directly related to the amount of protein in the original sample. To reach the specificity and sensitivity needed for biomarker quantitation in complex samples, peptide fractionations precede the end-stage quantitation step.

A suitable MASSTERCLASS assay may include the following steps:

Plasma/serum sample

Depletion of human albumin and IgG (complexity reduction on protein level) using affinity capture with anti-albumin and anti-IgG antibodies using ProteoPrep spin columns (Sigma Aldrich)

Spiking of known amounts of isotopically labelled peptides. This peptide has the same amino acid sequence as the proteotypic peptide of interest, typically with one isotopically labelled amino acid built in to generate a mass difference. During the entire process, the labelled peptide has identical chemical and chromatographic behaviour as the endogenous peptide, except during the end-stage quantitation step which is based on molecular mass.

Tryptic digest. The proteins in the depleted serum/plasma sample are digested into peptides using trypsin. This enzyme cleaves proteins C-terminally from lysine and argninine, except when a proline is present C-terminally of the lysine or arginine. Before digestion, proteins are denatured by boiling, which renders the protein molecule more accessible for the trypsin activity during the 16h incubation at 37° C.

First peptide-based fractionation: Free Flow Electrophoresis (FFE; BD Diagnostic) is a gel-free, fluid separation technique in which charged molecules moving in a continuous laminar flow are separated through an electrical field perpendicular to the flow. The electrical field causes the charged molecules to separate in the pH gradient according to their isoelectric point (pI). Only those fractions containing the monitored peptides are selected for further fractionation and LC-MS/MS analysis. Each peptide of interest elutes from the FFE chamber at a specific fraction number, which is determined during protein assay development using the synthetic peptide homologue. Specific fractions or fraction pools (multiplexing) proceed to the next level of fractionation.

Second peptide-based fractionation: Phenyl HPLC (XBridge Phenyl; Waters) separates peptides according to hydrophobicity and aromatic nature of amino acids present in the peptide sequence. Orthogonality with the back-end C18 separation is achieved by operating the column at an increased pH value (pH 10). As demonstrated by Gilar et al. 2005, *J Sep Sci* 28(14): 1694-1703), pH is by far the most drastic parameter to alter peptide selectivity in RP-HPLC. Each peptide of interest elutes from the Phenyl column at a specific retention time, which is determined during protein assay development using the synthetic peptide homologue. The use of an external control system, in which a mixture of 9 standard peptides is separated upfront a batch of sample separations, allows adjusting the fraction collection in order to correct for retention time shifts. The extent of fractionation is dependent on the concentration of the protein in the sample and the complexity of that sample.

LC-MS/MS based quantitation, including further separation on reversed phase (C18) nanoLC (PepMap C18; Dionex) and MS/MS: tandem mass spectrometry using MRM (4000 QTRAP; ABI)/SRM (Vantage TSQ; Thermo Scientific) mode. The LC column is connected to an electrospray needle connected to the source head of the mass spectrometer. As material elutes from the column, molecules are ionized and enter the mass spectrometer in the gas phase. The peptide that is monitored is specifically selected to pass the first quadrupole (Q1), based on its mass to charge ratio (m/z). The selected peptide is then fragmented in a second quadrupole (Q2) which is used as a collision cell. The resulting fragments then enter the third quadrupole (Q3). Depending on the instrument settings (determined during the assay development phase) only a specific peptide fragment or specific peptide fragments (or so called transitions) are selected for detection.

The combination of the m/z of the monitored peptide and the m/z of the monitored fragment of this peptide is called a transition. This process can be performed for multiple transitions during one experiment. Both the endogenous peptide (analyte) and its corresponding isotopically labelled synthetic peptide (internal standard) elute at the same retention time, and are measured in the same LC-MS/MS experiment.

The MASSterclass readout is defined by the ratio between the area under the peak specific for the analyte and the area under the peak specific for the synthetic isotopically labelled analogue (internal standard). MASSterclass readouts are directly related to the original concentration of the protein in the sample. MASSterclass readouts can therefore be compared between different samples and groups of samples.

A typical MASSTERCLASS protocol followed in the present study is given here below:

25 µL of plasma is subjected to a depletion of human albumin and IgG (ProteoPrep spin columns; Sigma Aldrich) according to the manufacturer's protocol, except that 20 mM $NH_4HCO_3$ was used as the binding/equilibration buffer.

The depleted sample (225 µL) is denatured for 15 min at 95° C. and immediately cooled on ice 500 fmol of the isotopically labelled peptide (custom made 'Heavy AQUA' peptide; Thermo Scientific) is spiked in the sample 20 µg trypsin is added to the sample and digestion is allowed for 16 h at 37° C.

The digested sample was first diluted ⅛ in solvent A (0.1% formic acid) and then 1/20 in the same solvent containing 250 amol/µL of all isotopically labelled peptides (custom made 'Heavy AQUA' peptide; Thermo Scientific) of interest.

20 µL of the final dilution was separated using reverse-phase NanoLC with on-line MS/MS in MRM/SRM mode:

Column: PepMap C18, 75 µm I.D.×25 cm L, 100 Å pore diameter, 5 µm particle size

Solvent A: 0.1% formic acid

Solvent B: 80% acetonitrile, 0.1% formic acid

Gradient: 30 min; 2%-55% Solvent B

MS/MS in MRM mode: method contains the transitions for the analyte as well as for the synthetic, labelled peptide.

The used transitions were experimentally determined and selected during protein assay development Each of the transitions of interest was measured for a period starting 3 minutes before and ending 3 minutes after the determined retention time of the peptide of interest, making sure that each peak had at least 15 datapoints.

The raw data was analysed and quantified using the LCQuan software (Thermo Scientific): the area under the analyte (=the PERLECAN peptide) peak and under the internal standard (the labelled, synthetic PERLE- CAN peptide) peak at the same C18 retention time was determined by automatic peak detection. These were cross-checked manually.

The MASSterclass readout was defined by the ratio of the analyte peak area and the internal standard peak area MASSTERCLASS Output The measured ratios are differential quantitations of peptides. In other words a ratio is the normalised concentration of a peptide. The concentration of a peptide is proportional to the ratio measured in the mass spectrometer.

Example 2

Screening of Acute Dyspnea Samples for PERLECAN

In this example the clinical utility of PERLECAN measurement for the evaluation of dyspneic patients was assessed.

The 299 clinical samples used in this study are part of the BASEL V cohort, a prospective study on consecutive patients presenting themselves to the ED of the university Hospital of BASEL with dyspnea as the most prominent symptom (part of this cohort is described in Potocki et al., Journal of Internal Medicine 2010 Jan;267(1):119-29). The gold standard for the diagnosis of acute heart failure was based interpretation of two independent cardiologists of all medical records pertaining to the patient including 90 day follow up data and BNP levels. Based on this, 56% (n=168) of patients were adjudicated to have an acute heart failure event, others were classified as dyspnea non-heart failure. A wide range of clinical and marker variables was collected (for summary see Table 1) including patient demographics, medical history, chronic medication, renal function parameters, echo parameters, established cardiac and inflammatory marker levels. Glomerular filtration rate was calculated using the Modification of Diet in Renal Disease (MDRD) formula (Stevens et al., New England Journal of Medicine 2006; 354:2473-83). Patients were followed up for at least 1 year post admission to the hospital and all-cause-mortality was recorded.

PERLECAN and Cystatin C levels were measured using MASSterclass™ assays as described in example 1. BNP, NT-proBNP and CRP levels were measured using commercially available immunoassays as described in Potocki et al (2010).

The diagnostic accuracy of a specific protein was determined by measuring the area under the Receiver-Operating-Characteristics (ROC) curves (AUC) as in Sullivan Pepe M (The statistical evaluation of medical tests for classification and prediction. 1993 Oxford University Press New York). The estimated and confidence intervals for AUCs were also computed using a non-parametric approach, namely bootstrapping (Efron B, Tibshirani R J. Nonparametric confidence intervals. An introduction to the bootstrap. Monographs on statistics and applied probability. 1993; 57:75-90 Chapman & Hall New York).

Associations of PERLECAN, Cystatin C, BNP, NT-proBNP and CRP levels with all available clinical parameters were computed using univariate statistical tests. Spearman's ranked test was used to compute correlation coefficients and Wilcoxon rank sum test for assessing whether two independent samples of observation originate from the same population.

TABLE 1

Summary of patient characteristics included in the study.

| Characteristic | all patients (n = 299) |
|---|---|
| age (yr) | 77 |
| gender (% male) | 52 |
| BMI | 26 |
| History (%) | |
| hypertension | 68 |
| heart failure | 24 |
| CAD | 28 |
| diabetes | 18 |
| COPD | 34 |
| chronic kidney disease | 28 |
| physical/ECG | |
| heart rate | 93 ± 23 |
| systolic bp | 138 ± 26 |
| diastolic bp | 83 ± 16 |
| LVEF | 24 (20-28) |
| lab s | |
| creatinin (umol/L) | 85 (66-120) |
| eGFR (mL/min/1.73 m2) | 67 (44-89) |
| BNP (pg/mL) | 350 (90-1120) |
| Nt-proBNP (pg/mL) | 1656 (314-6105) |
| diagnosis (%) | |
| ADHF | 56% |
| Pneumonia | 10% |
| Pulmonary embolism | 3% |
| COPD/Asthma | 16% |
| hyperventilation | 3% |
| other | 12% |
| outcome | |
| survival at 1 yr | 73% |

Example 3

PERLECAN Associates with Kidney Function Parameters

Figure 2B:
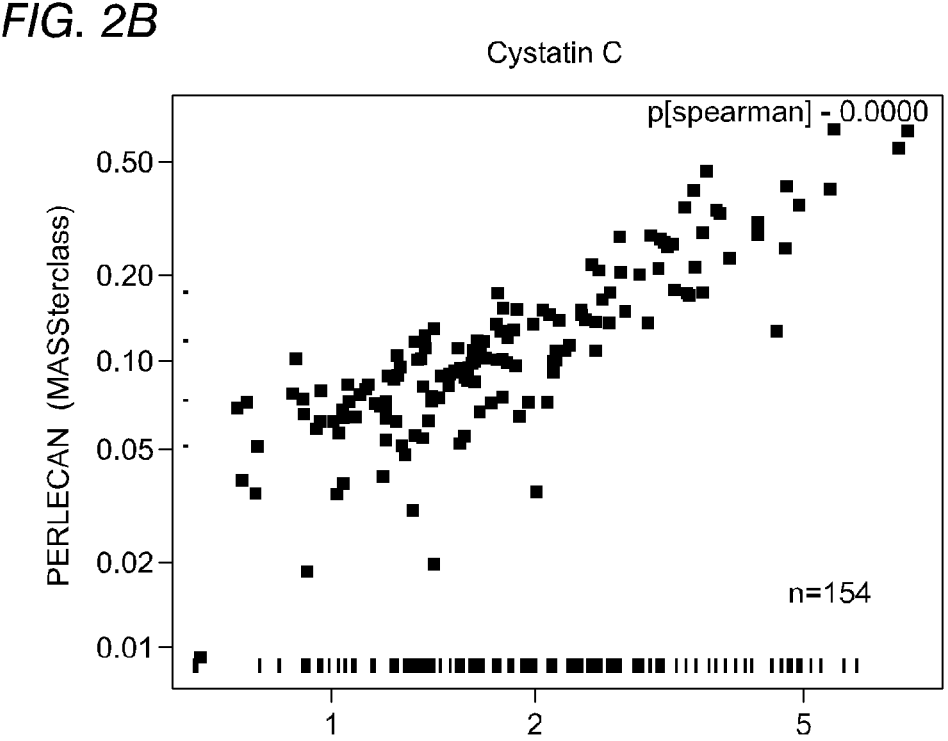

Screening acute dyspnea patients (example 2) for PERLECAN levels showed a clear association of PERLECAN level with all available clinical parameters related to kidney function as indicated by the low p-values for Spearman rank correlation with estimated glomerular filtration rate (eGfr), creatinin levels and blood urea nitrogen (BUN) levels and the low Wilcoxon p-values for presence/absence of history of kidney failure (summarized in Table 2). FIG. 2A illustrates the correlation of PERLECAN with eGfr, indicating PERLECAN is a good indicator of glomerular filtration. The correlation of PERLECAN with filtration is further corroborated by correlation with Cystatin C as shown in FIG. 2B, a known good marker for Gfr. Cystatin C was also measured in these samples using MASSterclass technology. The correlation of PERLECAN with Cystatin C and eGfr remains valid after correcting for presence of acute decompensated heart failure (Table 2).

TABLE 2

Summary statistics on univariate associations for Cystatin C and PERLECAN. Values mentioned for Spearman ranked test are correlation coefficients between 2 continuous variables, Wilcoxon test returns p-values which show significance of association between continuous marker levels and 2 discrete populations.

| Cohort | Population 1 | Population 2 | PERLECAN |
|---|---|---|---|
| BASEL | AHF (n = 85) | Dyspnea non AHF (n = 69) | 0.76 (0.68-0.83) |
| BASEL | Kidney failure (n = 40) | No kidney failure (n = 115) | 0.91 (0.83-0.97) |

| | population | PERLECAN |
|---|---|---|
| history__kidney.failure | AHF | 1.16E−07 |
| history__kidney.failure | dyspnea non AHF | 0.004415 |
| lab__creatinine | AHF | 4.78E−12 |
| lab__creatinine | dyspnea non AHF | 3.94E−08 |
| lab__creatinine.bin.150 | AHF | 3.77E−08 |
| lab__creatinine.bin.150 | dyspnea non AHF | 0.005128 |
| lab__creatinine.bin.250 | AHF | |
| lab__creatinine.bin.250 | dyspnea non AHF | |
| lab__gfr | AHF | 1.34E−11 |
| lab__gfr | dyspnea non AHF | 3.70E−08 |
| lab__urea.bin.7.5 | AHF | 2.16E−8 |
| lab__urea.bin.7.5 | dyspnea non AHF | 0.000257 |
| Cystatin C__MC089__B | AHF | 0 |
| Cystatin C__MC089__B | dyspnea non AHF | 1.27E−08 |
| medication.on.admission__diuretic | AHF | 5.04E−06 |
| medication.on.admission__diuretic | dyspnea non AHF | |

Example 4

PERLECAN as a Marker of Renal Dysfunction

Estimated glomerular filtration rate is a good indicator of how well the kidneys are functioning. Patients with eGfr below 60 for a minimum of 3 months are considered to have chronic kidney disease (CKD). The acute dyspnea population under study has 107 patients with reduced eGfr vs 192 patients with more normal glomerular filtration rates.

Figure 3A:
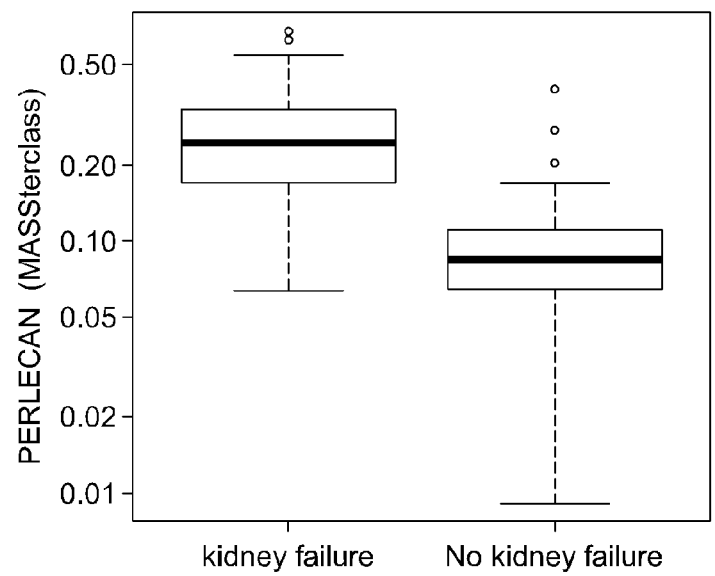
FIGS. 3A and 3B.
Figure 3B:
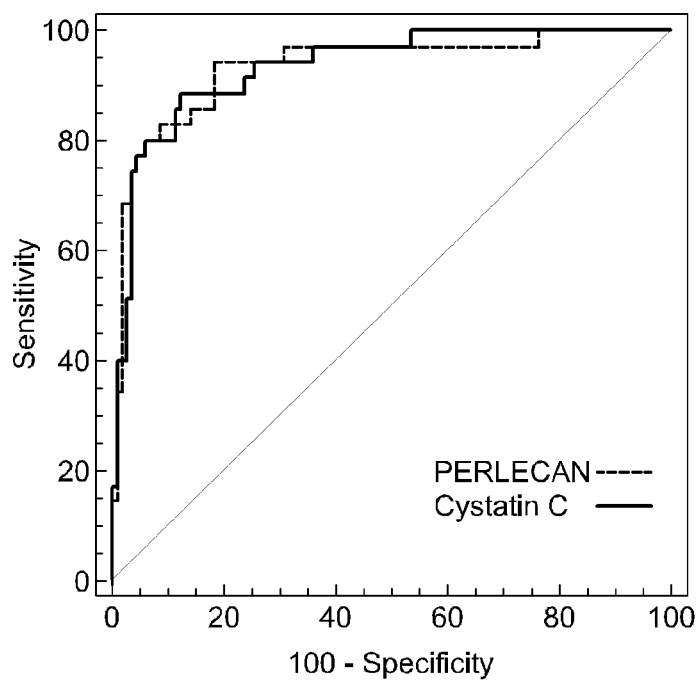

Receiver-operating characteristics (ROC) analysis demonstrated PERLECAN to be highly sensitive and specific for diagnosing kidney dysfunction in this population of dyspneic patients, as indicated by an overall median AUC of 0.9 with 95% CI 0.85-0.93 (FIGS. 3A and 3B). This diagnostic performance is equivalent to Cystatin C, the best available biomarker for chronic kidney disease.

Figure 4:
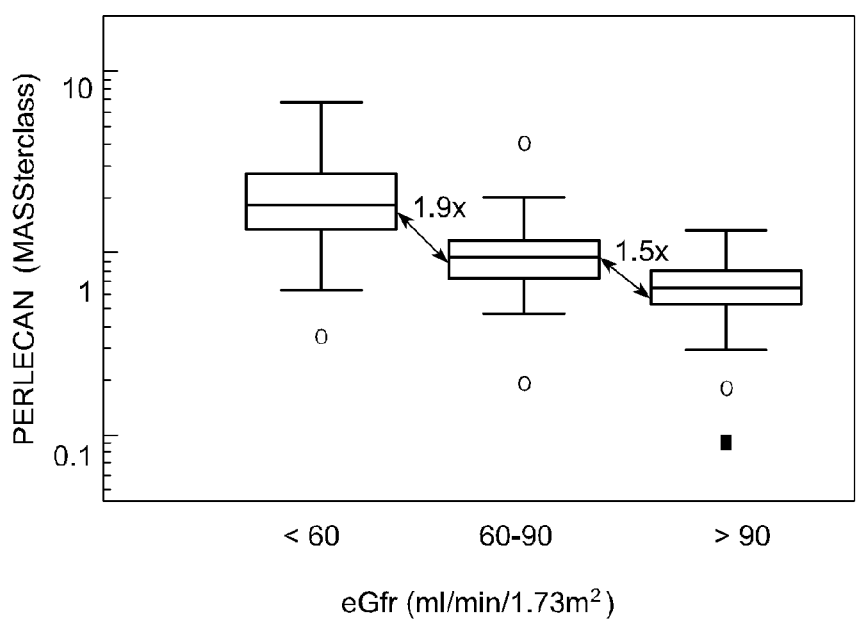
FIG. 4 shows box and whisker plots for PERLECAN in patients with reduced (<60) and normal (>90) and intermediate eGFR (60-90).

FIG. 4 illustrates relative levels of PERLECAN as measured by MASSterclass in patients with reduced (<60), intermediate (60-90) and normal (>90) estimated glomerular filtration rates. Median PERLECAN levels among patients with patients with reduced eGfr were 4,7 fold higher than patients with normal eGfr (>90). PERLECAN levels are also elevated in patients with slightly reduced kidney function (eGfr between 60 and 90).

Example 5

PERLECAN as a Marker for Acute Changes in Renal Function

The correlation of PERLECAN with Cystatin C and eGfr remains valid after correcting for presence of acute decompensated heart failure. The correlation in AHF patients hints to the fact that PERLECAN can detect acute changes in eGfr due to the acute decompensation of the heart (i.e., reduced cardiac output).

After restoring cardiac output and renal function by therapeutic intervention PERLECAN levels also return to baseline levels.

Example 6

PERLECAN as Predictive Marker for Mortality

In the cohort of acute dyspnea patients under study patients were followed up for at least one year post admission. At 1 year post admission, 82/299 subjects (27%) had died (all-cause mortality). The relation of PERLECAN and other clinical and marker variables to mortality was studied using different methods. Receiver-operator characteristic analysis with death at 1 year as the reference standard were performed and median area under the curve was calculated. Distributions of marker levels in "alive" and "death" patients were compared using the Wilcoxon rank-sum test. Kaplan Meier curves compared mortality rates across the follow-up period after presentation in groups divided as a function of PERLECAN levels.

Concentrations of PERLECAN at presentation in patients with acute dyspnea were significantly higher among patients who died by 1 year (n=82; 27%) compared with patients who were alive ($p=2e^{-11}$). This pattern of higher PERLECAN concentrations in decedents remained when subjects were considered as a function of the presence ($p=3.5e^{-08}$) or absence of acute heart failure (p=0.01) and when the population was divided based on renal function (eGfr<60; p=8.8e-05 vs eGfr>60; p=0.0003). This illustrates PERLECAN has the potential to predict bad outcome in a general dyspneic population as well as in an acute heart failure population and a chronic kidney disease population.

Figure 5:
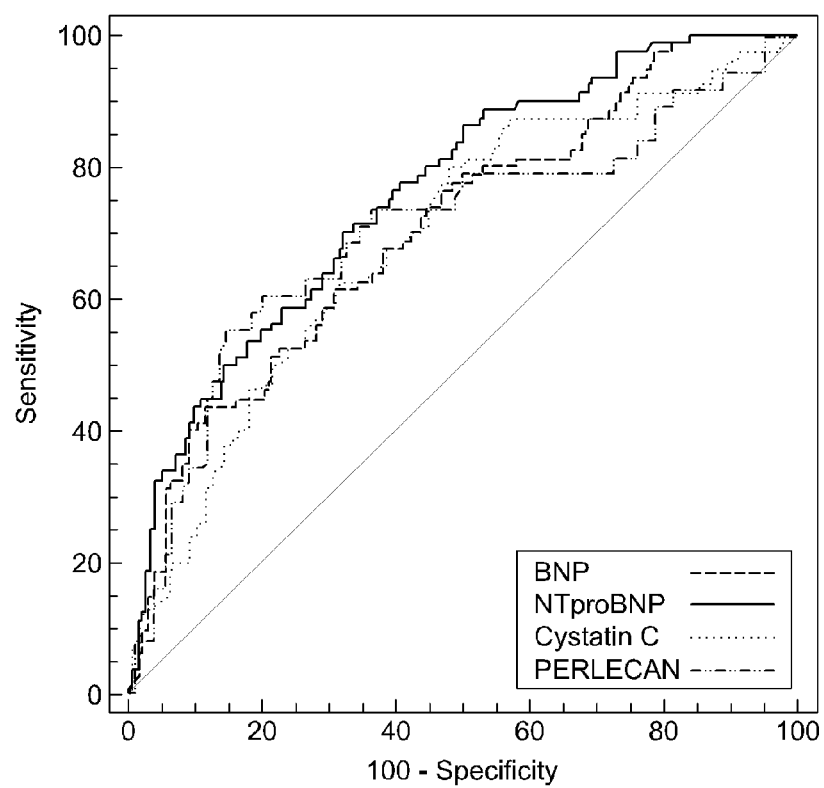
FIG. 5 shows a graph of the one year mortality prediction of the Basel V cohort, correlated with the levels of different renal failure markers. From the graph it is clear that PERLECAN is correlated to mortality in a similar manner as the BNP, NT-pro-BNP and Cystatin-C markers.

In addition decile analysis of PERLECAN concentrations examined as a function of mortality rates at 1 year revealed that there was a graded increase in mortality with rising concentrations of the marker. ROC analysis performed for predicting death at 1 year in all acute dyspnea patients demonstrated an AUC of 0.74 for PERLECAN (95% CI: 0.64-0.83), similar to NT-proBNP (AUC=0.77, but higher than BNP, Cystatin C and CRP protein markers (FIG. 5).

Example 7

PERLECAN Predicts Renal Replacement Therapy Requirement in Postoperative Patients PERLECAN levels were further studied in a cohort of cardiac surgery patients (n=100), both pre and 24 h post surgery. Patients were selected to include 50 patients who did develop AKI during follow-up matched with 50 controls. Of the 100 patients, 12% required renal replacement therapy (RRT) during follow-up. Table 3 summarizes the patient characteristics included in this study. The peptides detected are represented by SEQ ID Nos 4 and 6.

TABLE 3

Overview of patient characteristics that underwent cardiac surgery

| Variables | No RRT (n = 88) | RRT (n = 12) | P-value |
|---|---|---|---|
| Age (yrs) | 69.5 | 73.5 | p = 0.04 |
| Age >70 yrs | 53% (n = 47) | 69% (n = 8) | p = 0.22 |
| Gender (% male) | 76% (n = 67) | 69% (n = 8) | p = 0.72 |

TABLE 3-continued

Overview of patient characteristics that underwent cardiac surgery

| Variables | No RRT (n = 88) | RRT (n = 12) | P-value |
|---|---|---|---|
| Type of surgery | | | |
| CABG | 55% (n = 48) | 33% (n = 4) | p = 0.2 |
| Valve repair/replacement | 72% (n = 63) | 67% (n = 8) | p = 0.7 |
| concomitant | 30% (n = 26) | 25% (n = 3) | p = 1 |
| Pre-op kidney function | | | |
| eGfr | 63.8 (54-77) | 47.5 (41-67) | p = 0.07 |
| Serum creatinin | 88.4 | 122.4 | p = 0.06 |
| Serum creatinin >120 umol/L | | 50% (n = 6) | |
| Medical history | | | |
| NYHA III or IV | 26% (n = 23) | 0 | p = 1 |
| LVEF | 52.5 (39.25-60) | 50 (45-60) | p = 0.97 |
| COPD | 17% (n = 15) | 33% (n = 4) | P = 0.25 |
| IDDM | 6% (n = 5) | 0 | P = 0.61 |
| Outcome | | | |
| AKI | 44% | 91% (n = 10) | 0.004 |

Figure 6:
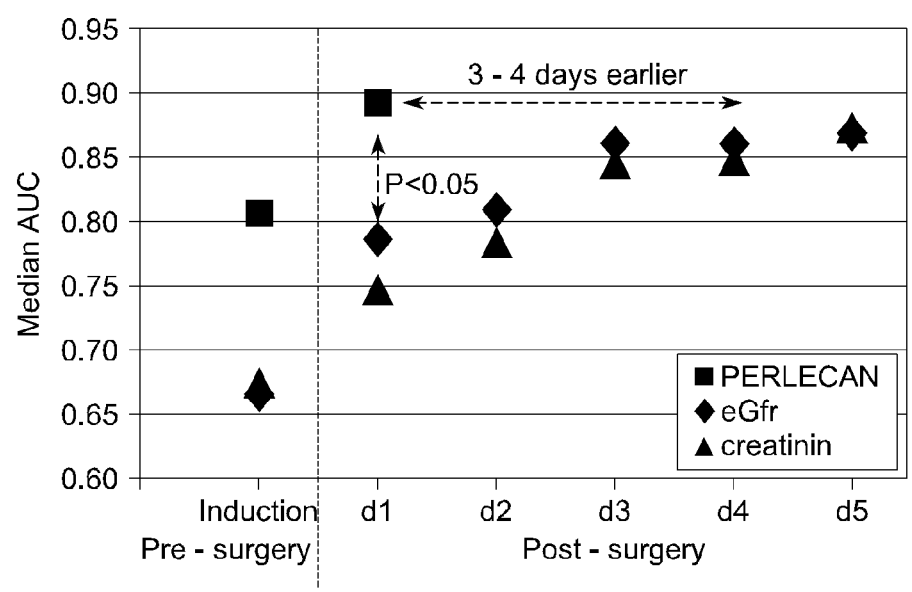
FIG. 6 illustrates the performance of PERLECAN as predictive and early diagnostic marker for renal replacement therapy requirement in comparison to creatinin based measures. From the graph it is clear that PERLECAN is a better and earlier predictor than creatinin and eGfr.

PERLECAN, Cystatin C, lactate, NGAL (plasma and urine) and serum creatinin levels were measured pre-surgery (at induction) and 24 hrs post surgery. Perlecan and Cystatin C were measured using MASSterclass, urine NGAL was measured on the ABBOTT Architect (ABBOTT diagnostics, Germany), plasma NGAL was measured using the Bioporto NGAL assay (Bioporto diagnostics, Denmark). The performances of the different markers to predict RRT requirement was calculated and are summarized in table 4. FIG. 6 illustrates the performance of PERLECAN compared to creatinin based prediction at different timepoints pre and post surgery. PERLECAN measured at 24 h post surgery is a good predictor of RRT requirement and is at this timepoint 3-4 days earlier to do so than creatinin based predictions. At the 24 h timepoint PERLECAN has significantly better performance than creatinin, or eGfr. Also pre-surgery already PERLECAN shows a better performance to predict RRT requirement.

TABLE 4

Performance of the different markers to predict RRT requirement both before and 24 h after surgery.

| timepoint | protein/marker | AUC (95% CI) |
|---|---|---|
| before | Ngal (plasma) | 0.69 (0.50-0.84) |
| before | Ngal (urine) | 0.52 (0.30-0.74) |
| before | lactate | 0.58 (0.43-0.72) |
| before | Cystatin C | 0.76 (0.61-0.88) |
| before | PERLECAN | 0.77 (0.62-0.88) |
| 24 h_post | Ngal (plasma) | 0.73 (0.55-0.88) |
| 24 h_post | Ngal (urine) | 0.58 (0.38-0.78) |
| 24 h_post | lactate | 0.68 (0.48-0.85) |
| 24 h_post | creatinin | 0.75 (0.59-0.88) |
| 24 h_post | Cystatin C | 0.87 (0.78-0.94) |
| 24 h_post | PERLECAN | 0.89 (0.81-0.95) |

Example 8

Figure 7B:
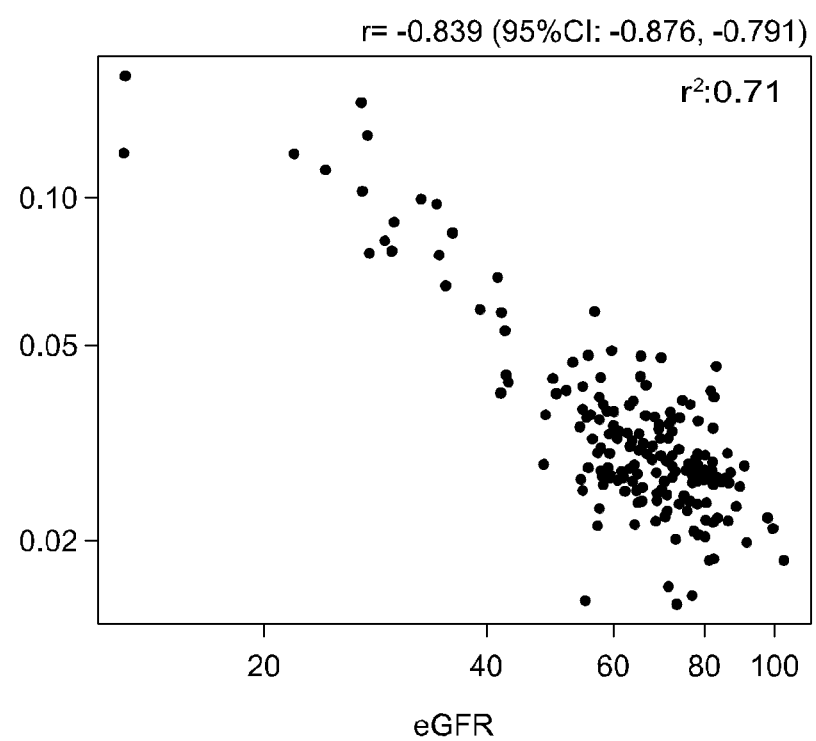

Different PERLECAN Peptides may Show Different Relation to Kidney Filtration Function Different MASSterclass assays were built that will quantify different domains/chains of the perlecan molecule (see table 5 and FIG. 7). The assay based on Seq ID no 7 is specific for the large perlecan molecule while the assays based on Seq IDs 4 and 6 will target the LG3 peptide, a reported biologically active fragment of perlecan. The assays targeted towards LG3 peptide are however not specific for this peptide and will also quantify endorepellin and the entire perlecan molecule as well.

The different assays were used to measure kidney filtration function in a cohort of type I diabetes patients. These patients have a good spread of eGfr, ranging from normal to severely impaired kidney function with eGfr below 40 ml/min /1.72 m2. The levels as measured with the LG3 assay correlate again nicely with eGfr (see FIG. 7) and this is true for both LG3 assays. In this particular experiment, the perlecan specific assay shows comparatively poorer correlation with eGfr and other filtration function related markers such as Cystatin C and beta-trace. Therefore the observed filtration function may probably stem from the LG3 peptide (and/or endorepellin molecule) and not from the entire perlecan molecule.

TABLE 5

| Sequence | Location Chain | SEQ ID NO |
|---|---|---|
| GSIQVDGEELVSGR | 4305-4318 LG3 domain | 4 |
| SLPEVPETIELEVR | 4222-4235 LG3 domain | 6 |
| LEGDTLIIPR | 3258-3267 Perlecan domain | 7 |

The results are depicted in FIG. 7 and in table 6 below.

TABLE 6

| Correlation coefficient $r^2$ | Perlecan assay | LG3/endorepellin assay |
|---|---|---|
| Cystatin C | 0.216 | 0.923 |
| LG3/endorepellin | 0.214 | 0.937 |
| Beta trace | 0.162 | 0.897 |

What is claimed is:

1. A method for treating renal dysfunction in a subject, wherein the method comprises:
   a) identifying the subject as in need of treatment for renal dysfunction by a method comprising:
      (i) contacting an antibody or aptamer capable of specifically detecting the LG3 domain of Perlecan with a blood sample from the subject;
      (ii) measuring the quantity of the LG3 domain of Perlecan in the blood sample by determination of the binding of the antibody or aptamer to the LG3 domain of Perlecan;
      (iii) comparing the quantity of the LG3 domain of Perlecan measured in (i) with a reference value of the quantity of the LG3 domain of Perlecan, said reference value representing a known diagnosis, prediction and/or prognosis of renal dysfunction or normal renal function, and finding a deviation of the quantity of the LG3 domain of Perlecan measured in (i) from said reference value so as to identify the subject as in need of the treatment; and
   b) treating the subject having the deviation, with a treatment or therapy selected from the group consisting of low-potassium and/or low phosphorus diet, phosphorus-lowering medications, iron supplements, blood pressure medications, vitamin supplements, haemodialysis, ultrafiltration, peritoneal dialysis, and kidney transplantation, wherein an elevated quantity of LG3 domain of Perlecan in the sample from the subject compared to the reference value identifies the subject as in need of treatment for renal dysfunction.

2. The method according to claim 1, wherein the renal dysfunction is characterised by reduced glomerular filtration rate (GFR) or estimated glomerular filtration rate (eGFR), wherein a threshold between normal and reduced GFR or eGFR is set at a value between about 50 and about 70 ml/min/1.73 m$^2$, wherein a value above said threshold denotes normal GFR or eGFR and a value below said threshold denotes reduced GFR or eGFR.

3. The method according to claim 1, wherein the renal dysfunction is characterised by proteinuria, is chronic allograft nephropathy, is type II diabetes, is acute renal failure, is chronic renal failure, or is associated or caused by renal fibrosis.

4. The method according to claim 1, wherein the therapy to treat renal dysfunction is haemodialysis, ultrafiltration or peritoneal dialysis in postoperative and/or critically ill patients.

5. The method according to claim 1, wherein the timing or scheduling of dialysis in a chronic dialysis patient is determined by alterations in the quantity of the LG3 domain Perlecan measured in said patient over time.

6. The method according to claim 1, wherein the renal dysfunction is proteinuria.

7. The method according to claim 1, wherein the quantity of the LG3 domain of Perlecan is measured using an immunoassay technology.

8. A kit for performing the method according to claim 1, the kit comprising (i) an antibody or aptamer specifically binding to the LG3 domain of Perlecan, for measuring the quantity of the LG3 domain of Perlecan in a sample from the subject, and further comprising (ii) a reference value of the quantity of the LG3 domain of Perlecan or means for establishing said reference value, wherein said reference value represents a known diagnosis, prediction and/or prognosis of the renal dysfunction.

\* \* \* \* \*

UNITED STATES PATENT AND TRADEMARK OFFICE
CERTIFICATE OF CORRECTION

PATENT NO. : 8,501,418 B2
APPLICATION NO. : 13/204443
DATED : August 6, 2013
INVENTOR(S) : Kas et al.

It is certified that error appears in the above-identified patent and that said Letters Patent is hereby corrected as shown below:

In the Specification:

In column 5 at line 26, Change "and for" to --and/or--.

In column 5 at line 34, Change "hematocrite," to --hematocrit,--.

In column 6 at line 16, Change "creatinin" to --creatinine--.

In column 6 at line 21, Change "darbepoietin)," to --darbepoetin),--.

In column 19 at line 25, Change "creatinin" to --creatinine--.

In column 19 at line 27, Change "creatinin" to --creatinine--.

In column 21 at line 40, Change "myoloma)" to --myeloma)--.

In column 21 at lines 63-64 (approx.), Change "Eeclampsia or Preclampsia" to --Eclampsia or Preeclampsia--.

In column 22 at line 23, Change "creatinin" to --creatinine--.

In column 22 at line 24, Change "creatinin" to --creatinine--.

In column 23 at line 46, Change "urinanalysis," to --urinalysis,--.

In column 24 at lines 10-13 (approx.), Delete "tables of birth.........200-208)." and insert the same on Col. 24, Line 9, after "U.S." as continuation of the same paragraph.

In column 27 at line 43, Change "Alta" to --Acta--.

In column 27 at line 44, Change "inplant" to --implant--.

In column 32 at line 22, Change "$K_A 24\ 1\times 10^{11}$" to --$K_A \geq 1\times 10^{11}$--.

In column 33 at line 17, Change "dromaderius)," to --dromedarius),--.

In column 33 at line 17, Change "paccos," to --pacos,--.

In column 44 at line 8, Change "Internet" to --internet--.

In column 46 at line 41, Change "form" to --from--.

In column 49 at line 20, Change "argninine," to --arginine,--.

Signed and Sealed this
Eighteenth Day of February, 2014

Michelle K. Lee
*Deputy Director of the United States Patent and Trademark Office*

CERTIFICATE OF CORRECTION (continued)
U.S. Pat. No. 8,501,418 B2

In column 52 at line 25 (approx.), Change "creatinin" to --creatinine--.

In column 52 at line 55 (approx.), Change "creatinin" to --creatinine--.

In column 55 at line 12 (approx.), Change "creatinin" to --creatinine--.

In column 55 at line 13 (approx.), Change "creatinin" to --creatinine--.

In column 55 at line 25 (approx.), Change "creatinin" to --creatinine--.

In column 55 at line 33 (approx.), Change "creatinin" to --creatinine--.

In column 55 at line 37 (approx.), Change "creatinin" to --creatinine--.

In column 55 at line 55 (approx.), Change "creatinin" to --creatinine--.

In the Claims:

In column 84 at line 67 (approx.), In Claim 1, after "of" insert --the--.

In column 86 at line 3, In Claim 5, after "domain" insert --of--.